United States Patent
Cole et al.

(10) Patent No.: US 10,729,417 B2
(45) Date of Patent: Aug. 4, 2020

(54) KNEE FLEXION AND EXTENSION GAP TENSIONING AND MEASURING METHOD

(71) Applicant: Little Engine, LLC, Belmont, NC (US)

(72) Inventors: J. Dean Cole, Orlando, FL (US); Franz W. Kellar, Gastonia, NC (US); Michael D. Bissette, Belmont, NC (US); Franz Austen Kellar, Gastonia, NC (US)

(73) Assignee: Little Engine, LLC, Belmont, NC (US)

( * ) Notice: Subject to any disclaimer, the term of this patent is extended or adjusted under 35 U.S.C. 154(b) by 0 days.

(21) Appl. No.: 16/670,662

(22) Filed: Oct. 31, 2019

(65) Prior Publication Data
US 2020/0155135 A1 May 21, 2020

Related U.S. Application Data

(60) Provisional application No. 62/767,687, filed on Nov. 15, 2018.

(51) Int. Cl.
| | | |
|---|---|---|
| *A61B 17/02* | (2006.01) | |
| *A61B 17/88* | (2006.01) | |
| (Continued) | | |

(52) U.S. Cl.
CPC ........ *A61B 17/025* (2013.01); *A61B 17/1764* (2013.01); *A61B 17/8869* (2013.01);
(Continued)

(58) Field of Classification Search
CPC ............ A61B 5/4585; A61B 2090/064; A61B 2090/067; A61B 2017/0268; A61B 34/20
See application file for complete search history.

(56) References Cited

U.S. PATENT DOCUMENTS

| | | |
|---|---|---|
| 5,713,897 A | 2/1998 | Goble et al. |
| 5,935,129 A | 8/1999 | McDevitt et al. |
| (Continued) | | |

FOREIGN PATENT DOCUMENTS

| | | |
|---|---|---|
| WO | 2014188184 | 11/2014 |
| WO | 2017195046 | 11/2017 |

OTHER PUBLICATIONS

U.S. Appl. No. 16/192,300, filed Nov. 15, 2018.
(Continued)

*Primary Examiner* — David W Bates
(74) *Attorney, Agent, or Firm* — Trego, Hines & Ladenheim, PLLC

(57) ABSTRACT

A method for imparting tension across a human knee joint which includes a femur bone, a tibia bone, a patella bone, a patellar tendon, and ligaments, wherein the ligaments and patellar tendon are under anatomical tension to connect the femur and tibia together, creating a load-bearing articulating joint. The method includes: providing a tensioning device, including: a baseplate; a top plate; and a linkage interconnecting the baseplate and the top plate and operable to move the tensioning device between retracted and extended positions, wherein the top plate is pivotally connected to the linkage so as to be able to freely pivot about a pivot axis; positioning the tensioning device between the femur and the tibia; applying an actuating force to the linkage to move the tensioning device towards the extended position, so as to impart a controlled separating force driving the femur and tibia apart to extend the ligaments.

17 Claims, 44 Drawing Sheets

(51) Int. Cl.
    *A61B 17/17*     (2006.01)
    *A61B 90/00*     (2016.01)
    *A61B 17/56*     (2006.01)
    *A61B 17/16*     (2006.01)
    *A61B 17/00*     (2006.01)
    *A61B 17/68*     (2006.01)
    *A61B 17/15*     (2006.01)

(52) U.S. Cl.
    CPC ......... *A61B 17/154* (2013.01); *A61B 17/1675* (2013.01); *A61B 2017/00845* (2013.01); *A61B 2017/0268* (2013.01); *A61B 2017/564* (2013.01); *A61B 2017/565* (2013.01); *A61B 2017/681* (2013.01); *A61B 2090/067* (2016.02)

(56) References Cited

U.S. PATENT DOCUMENTS

| | | | |
|---|---|---|---|
| 6,022,377 A * | 2/2000 | Nuelle | A61B 17/025 606/102 |
| 6,162,234 A | 12/2000 | Freedland et al. | |
| 10,405,849 B1 | 9/2019 | Cole et al. | |
| 2001/0008971 A1 | 7/2001 | Schwartz et al. | |
| 2003/0032983 A1 | 2/2003 | Bonutti et al. | |
| 2005/0222488 A1 | 10/2005 | Chang et al. | |
| 2008/0288060 A1 | 11/2008 | Kaye et al. | |
| 2013/0102929 A1 * | 4/2013 | Haight | A61F 2/4657 600/587 |
| 2014/0094715 A1 * | 4/2014 | Stein | A61B 5/0031 600/587 |
| 2014/0194907 A1 | 7/2014 | Bonutti et al. | |
| 2016/0007909 A1 * | 1/2016 | Singh | A61F 2/4657 606/102 |
| 2016/0030156 A1 * | 2/2016 | Cole | A61F 2/4657 623/13.12 |
| 2016/0106409 A1 * | 4/2016 | Moholkar | A61B 17/025 606/90 |
| 2016/0278944 A1 | 9/2016 | D'Lima et al. | |
| 2017/0065438 A1 | 3/2017 | Burnikel | |
| 2017/0312099 A1 * | 11/2017 | Paszicsnyek | A61B 34/10 |
| 2018/0177612 A1 * | 6/2018 | Trabish | A61F 2/4684 |
| 2019/0076273 A1 * | 3/2019 | Goodchild | A61B 5/4851 |
| 2019/0167447 A1 * | 6/2019 | Angibaud | A61B 5/4585 |

OTHER PUBLICATIONS

U.S. Appl. No. 16/523,712, filed Jul. 26, 2019.
Attune Knee System, CAS Surgical Technique, Published 2014, accessed at "http://synthes.vo.llnwd.net/o16/LLNWMB8/US%20Mobile/Synthes%20North%20America/Product%20Support%20Materials/Technique%20Guides/DSUS-JRC-0514-0141%20ATTUNE_CAS_ST.pdf".
Bathis et al., "Flexion Gap Configuration in Total Knee Arthroplasty Following Hight Tibial Osteotomy", published online Sep. 30, 2004, International Orthopaedics (SICOT) 28: 366-369.
M. J. Winemaker, MD, FRCS (C), "Perfect Balance in Total Knee Arthroplasty, The Elusive Compromise", The Journal of Arthroplasty vol. 17. No. 1 2002, 2002, Churchill Livingstone, Canada.
International Search Report and Written Opinion from the International Searching Authority for related International Patent Application No. PCT/US2019/061668 dated Jan. 14, 2020.

* cited by examiner

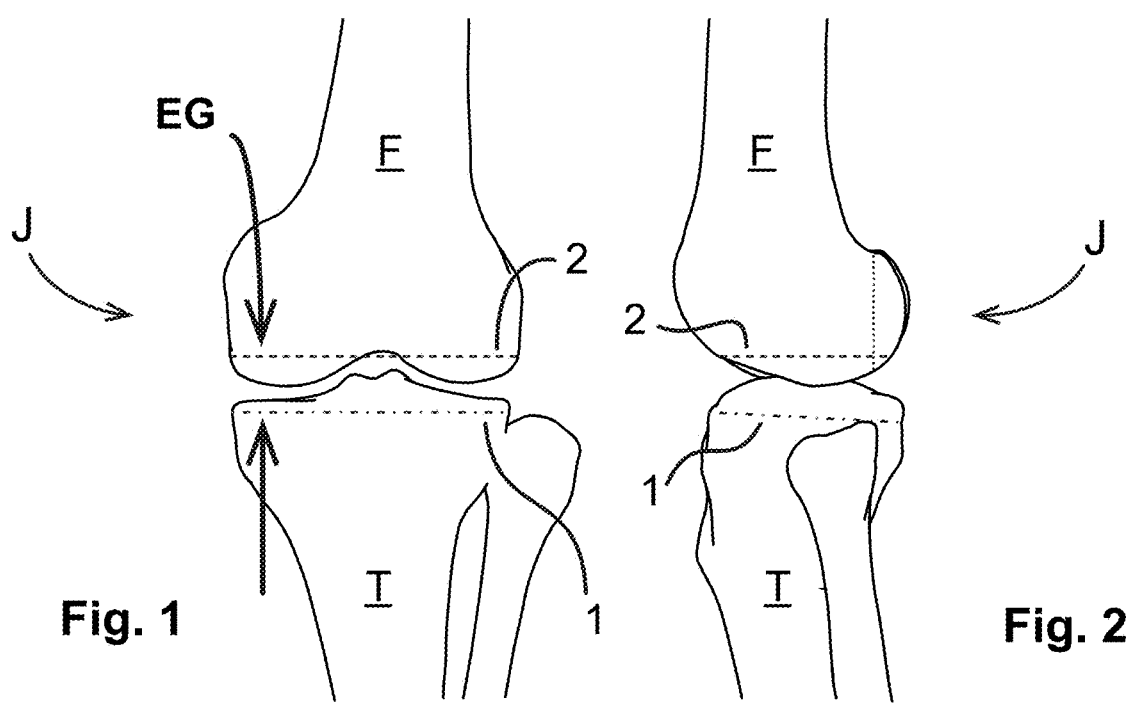
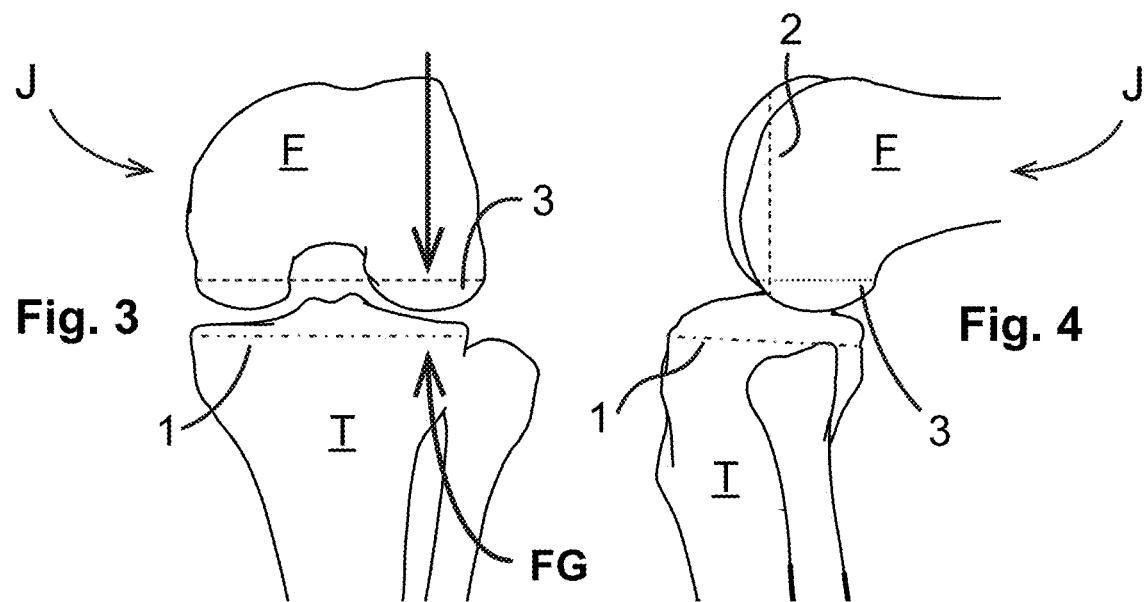

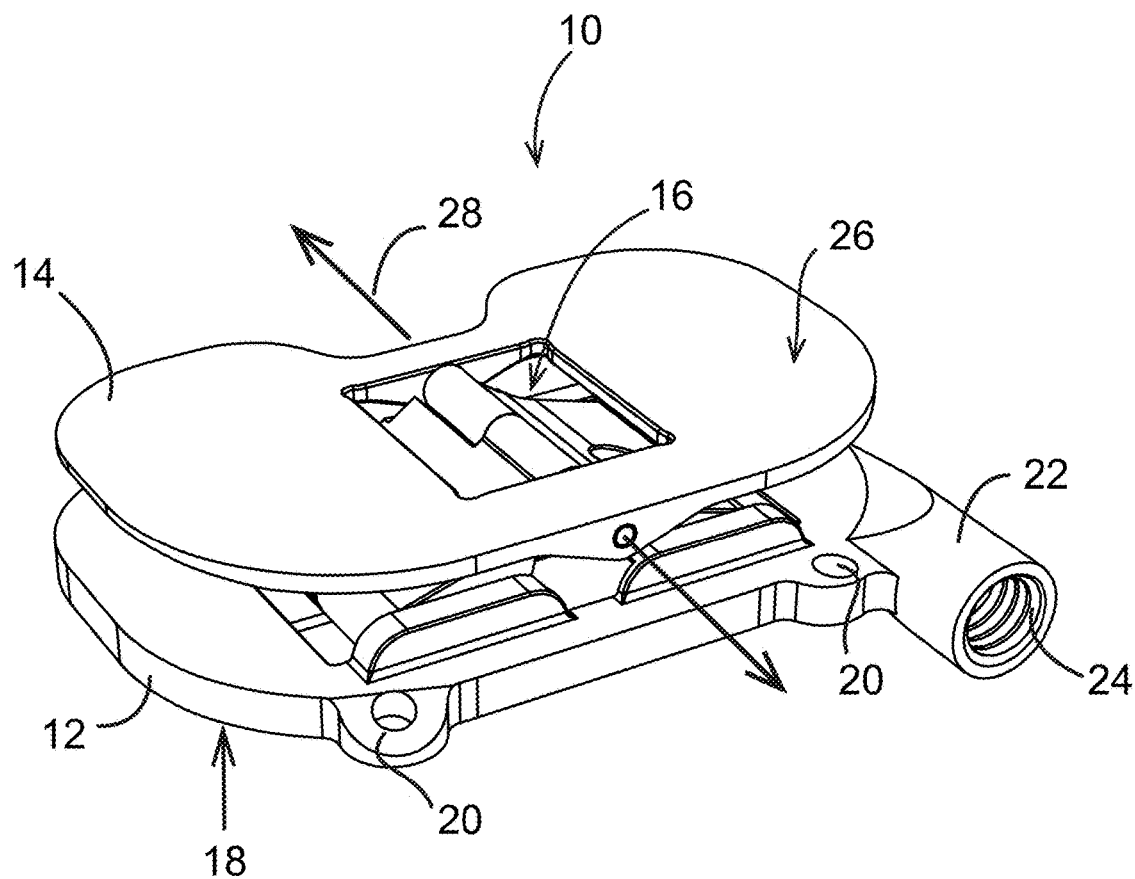
Fig. 5
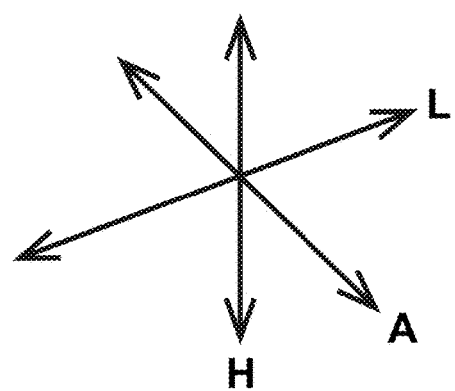

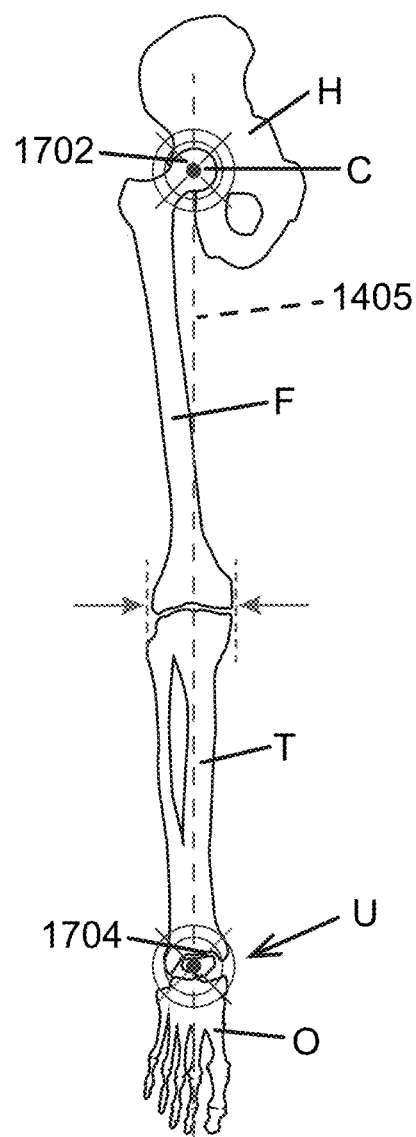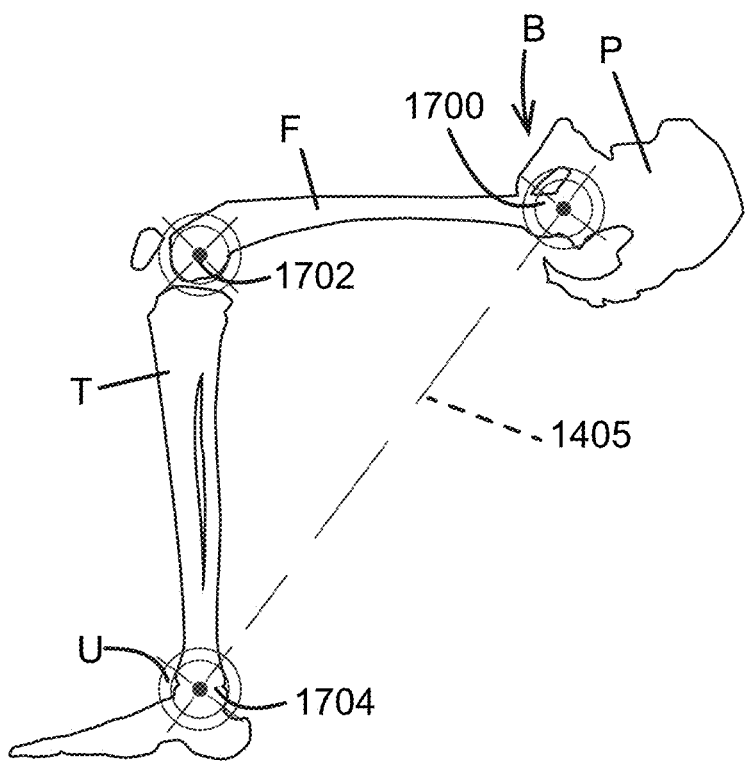
FIG. 78
FIG. 79

KNEE FLEXION AND EXTENSION GAP TENSIONING AND MEASURING METHOD

This invention relates generally to medical devices and instruments, and more particularly to a method for applying tension along or across a human knee joint to take measurements to repair, augment, or replace it.

BACKGROUND

Total knee arthroplasty ("TKA") is a procedure for treating an injured, diseased, or worn human knee joint. In a TKA, an endoprosthetic joint is implanted, replacing the bearing surfaces of the joint with artificial members. Proper alignment of the joint and substantially equal tension in the soft tissues surrounding the joint are important factors in producing a good surgical outcome.

A human knee joint "J" is shown in FIG. 1-4. The joint J is prepared for implantation by cutting away portions of the femur "F" and the tibia "T". FIGS. 1 and 2 show the joint in extension, with cutting planes for a tibial cut 1 and a distal femoral cut 2. The tibial cut 1 and the distal formal cut 2 cooperate to define an extension gap "EG". FIGS. 3 and 4 show the joint J in flexion, with cutting plane 3 for a posterior cut. The tibial cut 1 and the posterior cut 3 cooperate to define a flexion gap "FG".

A goal of total knee arthroplasty is to obtain symmetric and balanced flexion and extension gaps FG, EG (in other words, two congruent rectangles). These gaps are generally measured in millimeters of separation, are further characterized by a varus or valgus angle measured in degrees, and are measured after the tibia cut, distal femoral cut, and posterior femoral cut have been done (to create flat surfaces from which to measure). It follows that, to achieve this balance, the ligament tension in the lateral and medial ligaments would be substantially equal on each side, and in each position; it also follows that the varus/valgus angle in flexion and extension would be 0°.

Some surgeons favor the use of a measured resection technique in which bone landmarks, such as the transepicondylar, the anterior-posterior, or the posterior condylar axes are used to determine proper femoral component rotation and subsequent gap balance. Others favor a "gap balancing technique" in which the femoral component is positioned parallel to the resected proximal tibia with each collateral ligament substantially equally tensioned to obtain a rectangular flexion gap.

One problem with prior art balancing techniques is that it is difficult and complex to achieve the proper balance. Current state-of-the-art gap balancing devices do not enable balancing with the patella in-place and are large, overly-complicated devices that work only with their respective knee systems.

BRIEF SUMMARY OF THE INVENTION

This problem is addressed by a using gap tensioner operable to apply a load to a gap between the bones of a joint and measure the resulting gap distance and angle between the bones.

According to one aspect of the invention, a method is provided for imparting tension across a human knee joint which includes a femur bone, a tibia bone, a patella bone, a patellar tendon, and ligaments, wherein the ligaments and patellar tendon are under anatomical tension to connect the femur and tibia together, creating a load-bearing articulating joint. The method includes: providing a tensioning device, including: a baseplate; a top plate; and a linkage interconnecting the baseplate and the top plate and operable to move the tensioning device between retracted and extended positions, wherein the top plate is pivotally connected to the linkage so as to be able to freely pivot about a pivot axis; positioning the tensioning device between the femur and the tibia; applying an actuating force to the linkage to move the tensioning device towards the extended position, so as to impart a controlled separating force driving the femur and tibia apart to extend the ligaments.

According to another aspect of the invention, a method for balancing extension and flexion gaps between the tibia and the femur of a knee joint, including: making a tibial cut along the first cutting plane to cut away a proximal portion of the tibia, and making a distal femoral cut along a second cutting plane to cut away a distal portion of the femur, such that an extension gap is defined between the first and second cutting planes; positioning the knee joint in extension and inserting a gap tensioner into the extension gap, the gap tensioner including: a baseplate; a top plate; a linkage interconnecting the baseplate and the top plate and operable to move the gap tensioner between retracted and extended positions; and wherein the top plate is pivotally connected to the linkage so as to be able to freely pivot about a pivot axis; actuating the linkage to move the gap tensioner towards the extended position, so as to urge the tibia and the femur apart and apply tension to the medial and lateral collateral ligaments of the knee joint; and determining an adjustment required to bring the first and second cutting planes into a desired angular orientation relative to each other; positioning the knee joint in flexion, thereby defining a flexion gap between the femur and the tibia; positioning the gap tensioner into the flexion gap and actuating the linkage to move the gap tensioner towards the extended position, so as to urge the tibia and the femur apart and apply tension to the medial and lateral collateral ligaments of the knee joint; and determining a third cutting plane to be used for a posterior cut on the femur which will result in the first and third cutting planes being substantially parallel in at least one axis; removing the gap tensioner; and making the posterior cut along the third cutting plane.

According to another aspect of the invention, a method is provided for measuring alignment of a human knee joint which includes a femur bone, a tibia bone, a patella bone, a patellar tendon, and ligaments, wherein the ligaments and patellar tendon are under anatomical tension to connect the femur and tibia together, creating a load-bearing articulating join. The method includes: providing a gap tensioning apparatus including: a gap tensioner including: a baseplate; a top plate; a linkage interconnecting the baseplate and the top plate and operable to move the gap tensioner between retracted and extended positions; and wherein the top plate is pivotally connected to the linkage so as to be able to freely pivot about a pivot axis; inserting the gap tensioner between the tibia and the femur, with the gap tensioner in the retracted position; actuating the linkage to move the gap tensioner towards the extended position, so as to urge the tibia and the femur apart and apply tension to the medial and lateral collateral ligaments of the knee joint; associating at least two tracking markers with the knee joint; providing an electronic receiving device, wherein the receiving device is operable in combination with the tracking markers to determine a position and orientation of each of the tracking markers relative to the electronic receiving device; moving the knee joint through at least a portion of its range of motion; while moving the knee joint, collecting position data from the tracking markers; and processing the collected position data to compute an origin of motion of the knee joint.

BRIEF DESCRIPTION OF THE DRAWINGS

The invention may be best understood by reference to the following description taken in conjunction with the accompanying drawing figures in which:

FIG. 1 is a view of the anterior aspect of the human knee joint in extension showing cutting planes for a total knee arthroscopy;

FIG. 2 is a view of the lateral aspect of the human knee joint of FIG. 1;

FIG. 3 is a view of the anterior aspect of the human knee joint in flexion showing cutting planes for a total knee arthroscopy;

FIG. 4 is a view of the lateral aspect of the human knee joint of FIG. 3;

FIG. 5 is a perspective view of an exemplary gap tensioner;

FIG. 78 is a view of an anterior aspect of the human leg in extension, with tracking markers superimposed thereon;

FIG. 79 is a view of a medial aspect of the human leg of FIG. 78 in flexion;

DETAILED DESCRIPTION OF THE INVENTION

Figure 6:
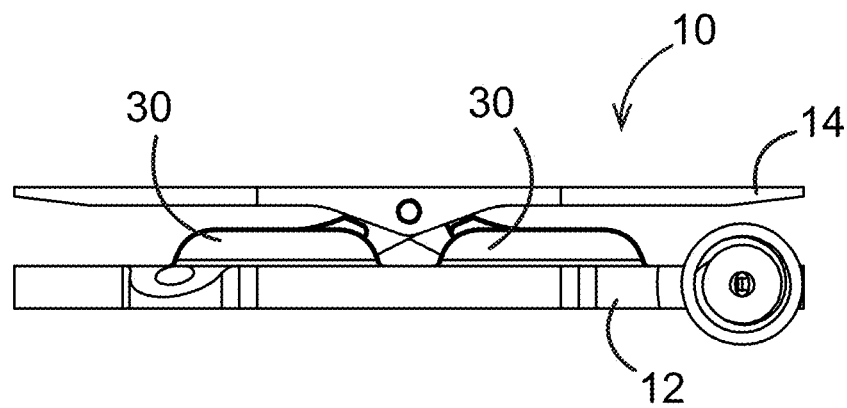
FIG. 6 is a front elevation view of the gap tensioner of FIG. 5, in a retracted position.

Referring to the drawings wherein identical reference numerals denote the same elements throughout the various views, FIG. 5 depicts an exemplary gap tensioner 10 (alternatively referred to as a "jack") which is useful for balancing a gap a human knee joint as part of a total knee arthroscopy. In one aspect, the gap tensioner 10 may be described as having the ability to constrain or fix four degrees of freedom of a knee joint while permitting controlled movement of two degrees of freedom.

The gap tensioner 10 comprises a baseplate 12 and a top plate 14 interconnected by a linkage 16. The linkage 16 and the gap tensioner 10 are movable between a retracted position in which the top plate 14 lies close to or against the baseplate 12, and an extended position in which the top plate 14 is spaced away from the baseplate 12. As described in more detail below, a mechanism is provided to actuate the linkage 16 in response to an actuating force in order to separate the baseplate 12 and the top plate 14 in a controllable manner.

Solely for purposes of convenient description, the gap tensioner 10 may be described as having a length extending along a lateral direction "L", a width extending along an axial direction "A", and a height extending along a vertical direction "H", wherein the lateral direction, the axial direction, and the vertical direction are three mutually perpendicular directions.

The baseplate 12 includes a generally planar tibia interface surface 18. The baseplate 12 may include pin holes 20 for the purpose of receiving alignment pins (not shown) which would be driven into bone during a surgical procedure. The baseplate 12 includes a gap tensioner coupler 22 having a first interface 24. In the illustrated example, the first interface 24 is configured as a threaded socket.

The top plate 14 includes a generally planar femur interface surface 26. The top plate 14 is mounted to the linkage 16 in such a manner that it can freely pivot about pivot axis 28. The pivot axis 28 is parallel to the tibia interface surface 18 and the femur interface surface 26, and in the illustrated orientation is parallel to the axial direction A. The gap tensioner 10 may be configured to permit use with the patella in place. This may be achieved by a careful selection of its dimensions and physical configuration. More specifically, an overall width of the gap tensioner 10 parallel to direction A in FIG. 5 may be selected to fit between a patella and either the medial collateral ligament or the lateral collateral ligament so the device can be inserted into the knee joint. Additionally, the gap tensioner coupler is positioned at or near the distal end of the baseplate 12 and is oriented so that it extends along and protrudes in the axial direction "A".

Figure 8:
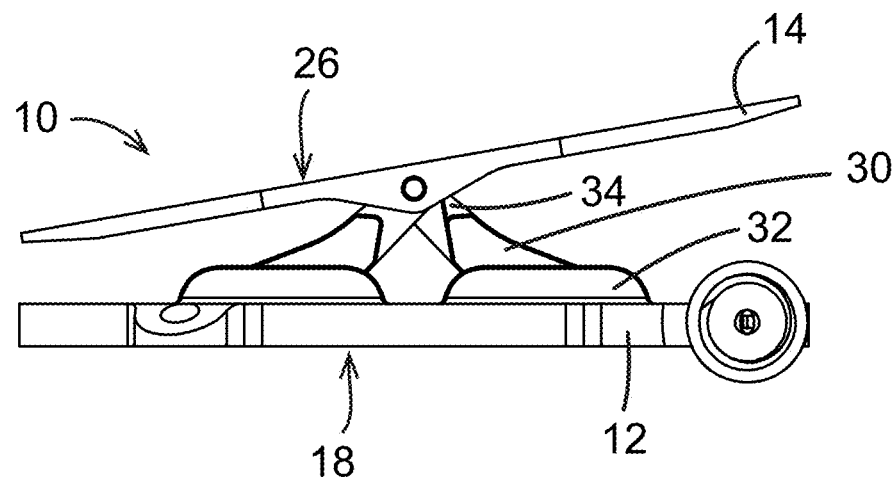
FIG. 8 is a front elevation view of the gap tensioner in FIG. 5, in an extended and tilted position.
Figure 7:
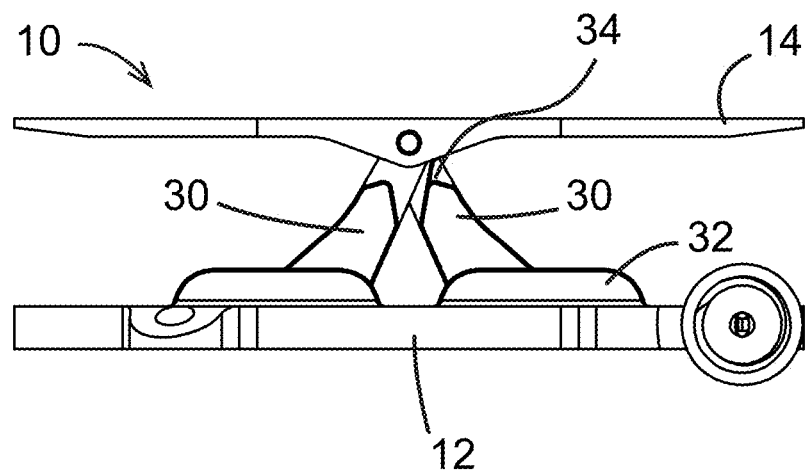
FIG. 7 is a front elevation view of the gap tensioner of FIG. 5, in an extended position.

FIGS. 6-8 illustrate the construction and operation of the gap tensioner 10 in more detail. In this embodiment, the linkage 16 is configured as a pair of links 30 each having a lower end 32 and an upper end 34. The upper ends 34 are joined together such that they can pivot about the pivot axis 28, thus forming a "X" or "V" configuration. The lower ends 32 are mounted to the baseplate 12 such that they can slide in the lateral direction. Thus assembled, movement of the lower ends 32 away from each other retracts or lowers the height of the gap tensioner 10, and movement of the lower ends 32 towards each other extends or raises the height of the gap tensioner 10. Accordingly, in use, an actuating force may be applied to the lower ends 32 to move them towards each other, thus extending the top plate 14 away from the baseplate 12. The linkage 16 has predetermined kinematic properties, or stated another way, the ratio of displacement of the top plate 14 to input displacement is known and can be plotted a graph, for the entire range of motion.

FIG. 6 illustrates the gap tensioner 10 in the retracted position, and FIG. 7 illustrates the gap tensioner in the extended position. In all positions, the top plate 14 is free to pivot about the pivot axis 28. FIG. 8 shows an example of the top plate 14 in a "tilted" position, or stated another way, with the femur interface surface 26 not parallel to the tibia interface surface 18.

Figure 9:
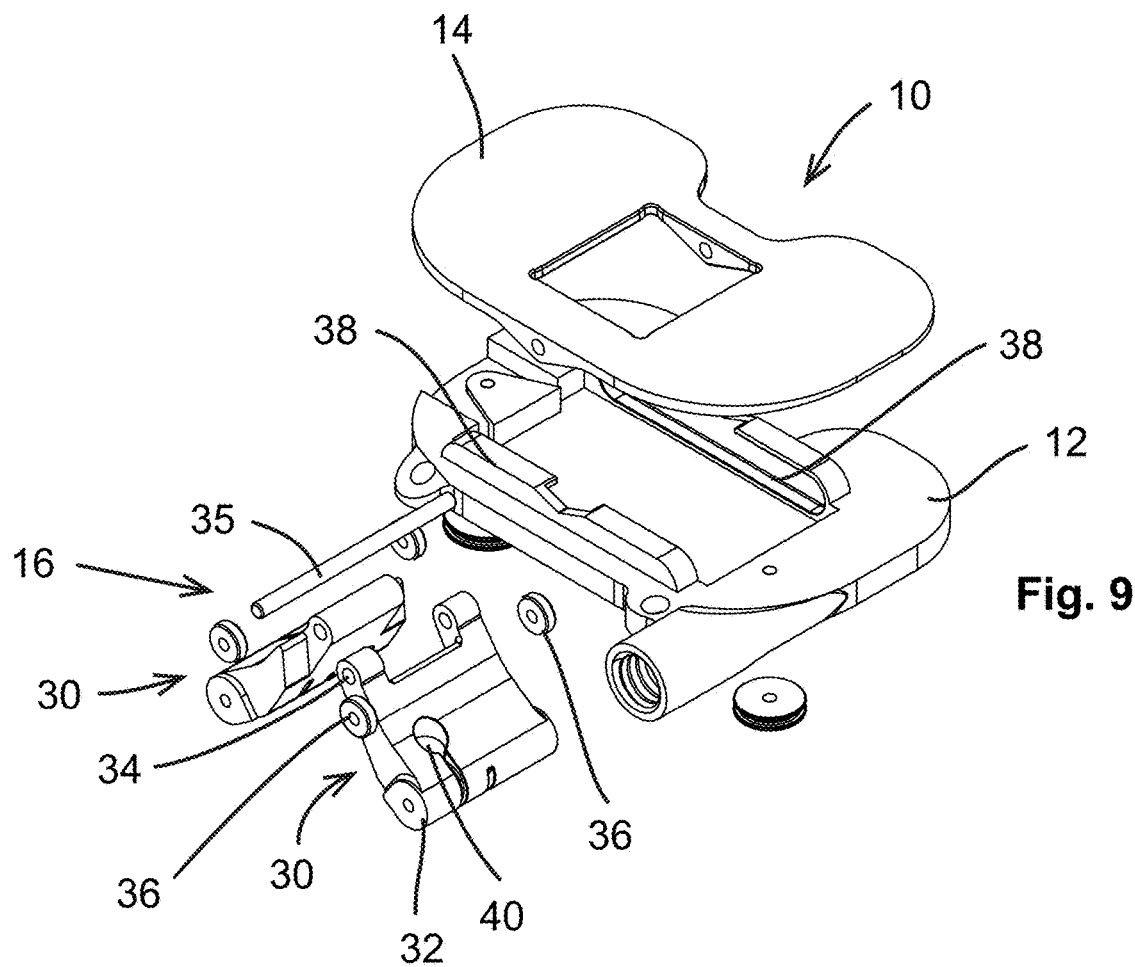
FIG. 9 is an exploded perspective view of the gap tensioner of FIG. 5.

FIG. 9 illustrates a structure of the linkage 16 in more detail. In particular it shows the links 30 as well as a pivot pin 35 which serves to connect the upper ends 34 of the links 30 as well as to join the links 30 in a pivoting connection to the top plate 14.

In this embodiment, the lower end 32 of each link 30 has a roller 36 mounted thereto. The rollers are received in tracks 38 formed in the baseplate 12. This permits low-friction operation of the linkage 16.

Figure 10:
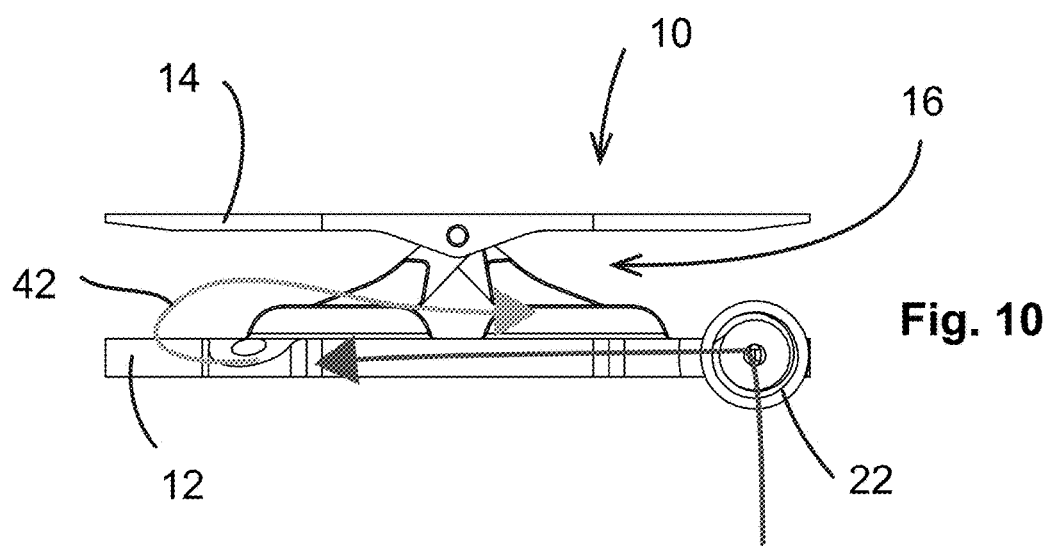
FIG. 10 is a front elevation view of the gap tensioner of FIG. 5 showing an internal cable routing path.

Various means are possible for applying an actuating force to the linkage 16. In the example shown in FIGS. 9 and 10, the linkage 16 is cable-actuated. One of the links 30 incorporates a cable anchor recess 40 which receives a first end of the cable (not seen in FIG. 9). The cable 42 is routed through the interior of the baseplate 12, exiting the gap tensioner coupler 22, as seen in FIG. 10. Thus, routed and assembled, a tensile actuating force applied to the cable 42 will move the lower ends 32 of the links 30 closer together.

Figure 11:
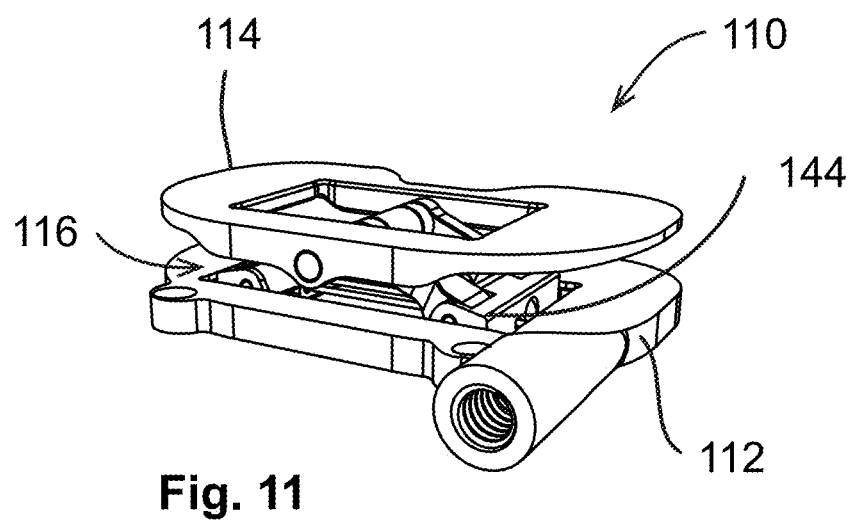
FIG. 11 is a perspective view of an alternative embodiment of a gap tensioner.
Figure 12:
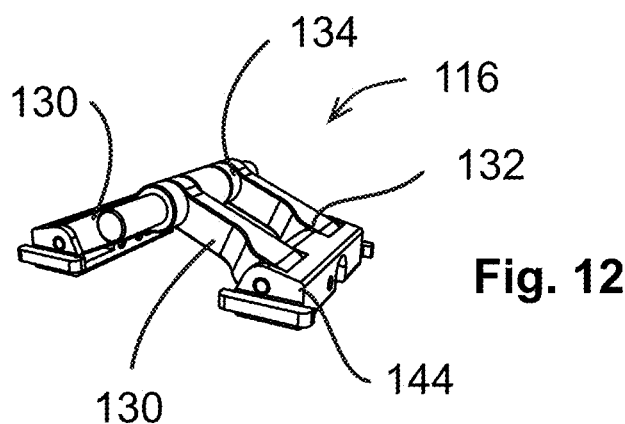
FIG. 12 is a perspective view of a linkage of the gap tensioner shown in FIG. 11.
Figure 13:
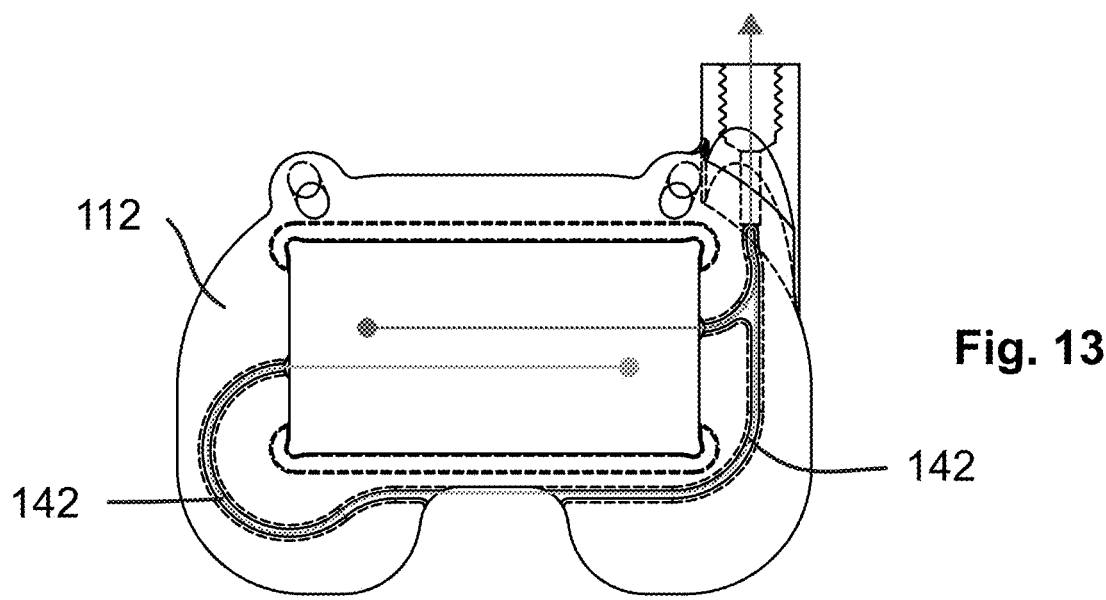
FIG. 13 is a schematic top plan view of the gap tensioner of FIG. 11, showing an internal cable routing thereof.

FIGS. 11-13 illustrate another exemplary gap tensioner 110. The gap tensioner 110 is similar in overall construction to the gap tensioner 10 described above. Elements of the gap tensioner 110 not explicitly described may be considered to be identical to corresponding elements of the gap tensioner 10.

The gap tensioner 110 includes a baseplate 112, top plate 114, and a linkage 116. In this embodiment, the linkage 116 is configured as a pair of links 130 each having a lower end 132 and an upper end 134. The lower ends 132 are mounted to the baseplate 112 such that they can slide in the lateral direction. The lower ends 132 of the links 130 are received in sliders 144 which are in turn received in slots or tracks (not visible) and the baseplate 112.

FIG. 13 illustrates cable routing within the baseplate 112. In this example, two separate cables 142 are provided, one cable being terminated in each of the sliders 144.

Figure 14:
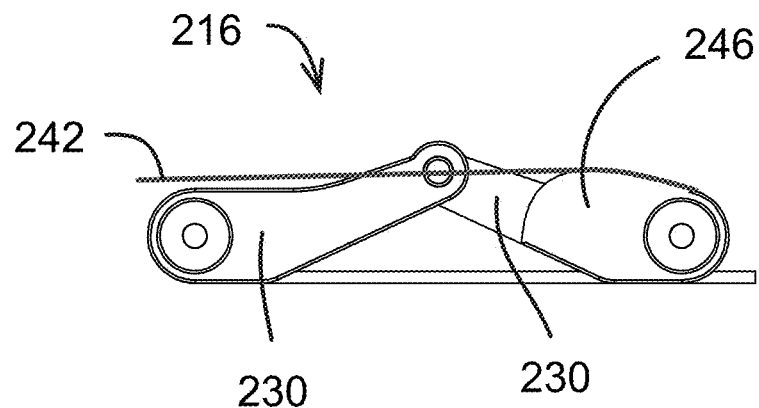
FIG. 14 is a front elevation view of an alternative gap tensioner linkage in a retracted position.
Figure 15:
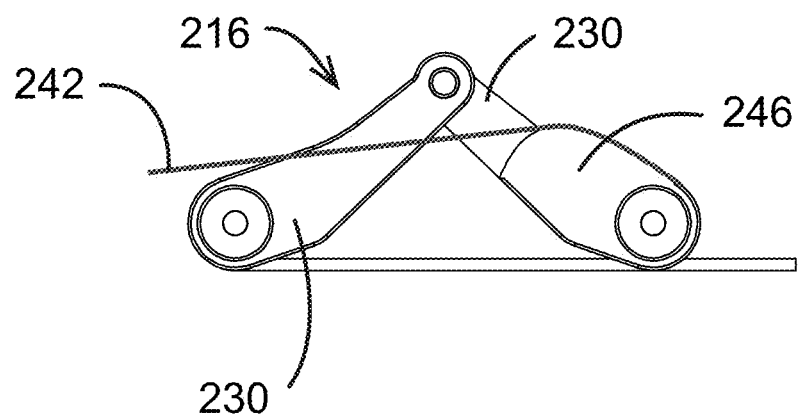
FIG. 15 is a front elevation view of the alternative gap tensioner linkage of FIG. 14, in a partially extended position.
Figure 16:
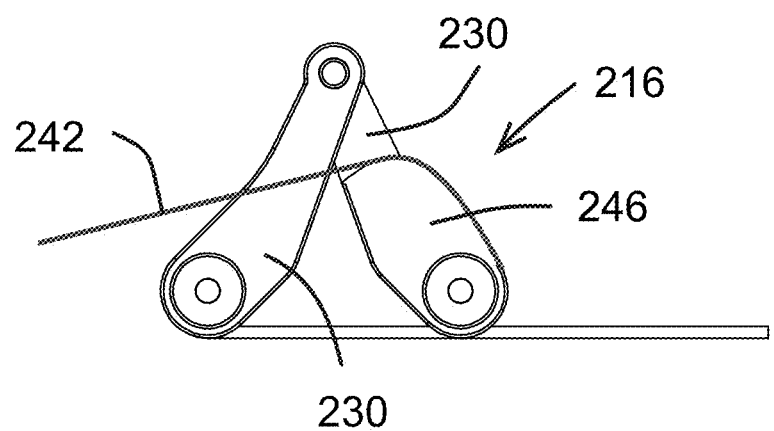
FIG. 16 is a front elevation view of the alternative gap tensioner linkage of FIG. 14, in an extended position.

FIGS. 14-16 illustrate an alternative linkage 216 comprising links 230, which may be substituted for the linkages described above. In this linkage 216, one of the links 230 includes a cam 246 around which a cable 242 is wrapped. The cam 246 is shaped such that as the linkage moves from a retracted position (FIG. 14) towards an extended position (FIG. 16), the force-versus-displacement characteristics of the linkage 216 change. Stated another way, the effective leverage of the cable 242 changes as the linkage 216 moves through its range of motion. For example, the cam may be shaped such that a greater force is required to provide a given deflection as the device moves towards extended position.

Figure 17:
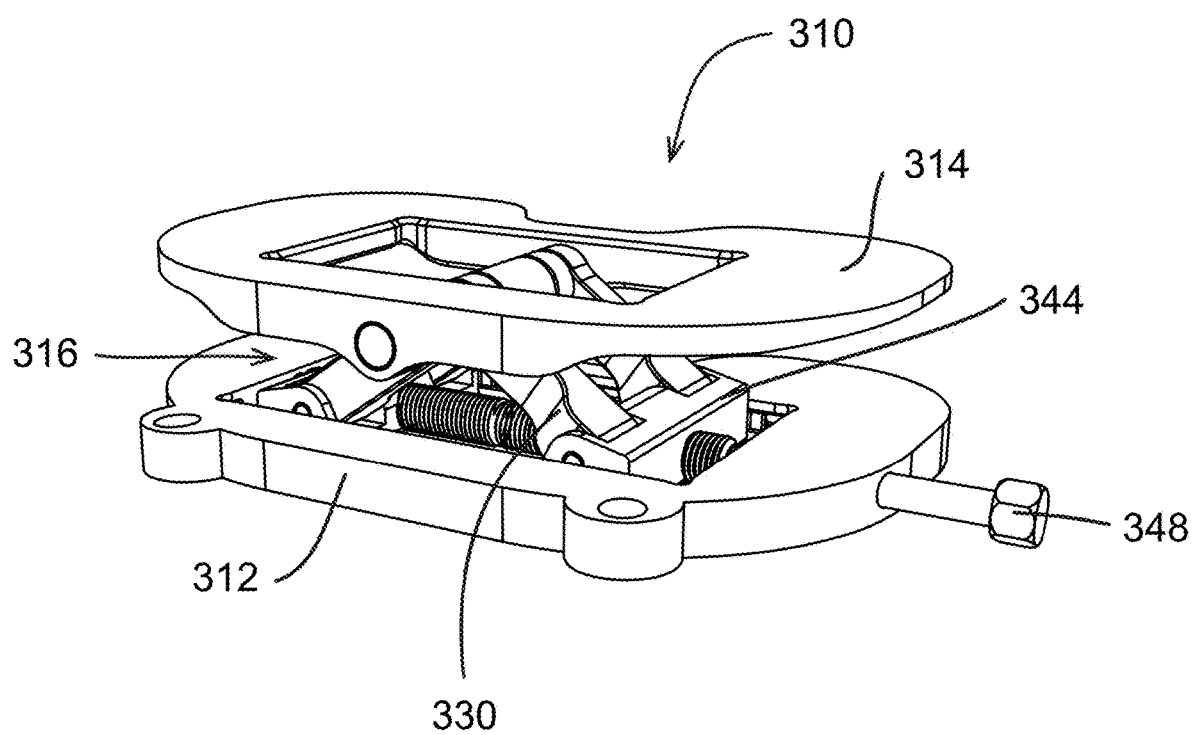
FIG. 17 is a schematic perspective view of an exemplary gap tensioner actuated by a mechanical screw.

FIG. 17 illustrates another example of a gap tensioner 310. The gap tensioner 310 is similar in overall construction to the gap tensioner 110 described above. Elements of the gap tensioner 310 not explicitly described may be considered to be identical to corresponding elements of the gap tensioner 110.

The gap tensioner 310 includes a baseplate 312, top plate 314, and a linkage 316. In this example, the linkage 316 is configured as a pair of links 330 each having a lower end received in a slider 344 which is in turn mounted for sliding movement in the baseplate 312. A linear actuating element 348 such as the illustrated threaded shaft is mounted in the baseplate configured such that rotating movement of the actuating element 348 causes lateral sliding of the sliders 344, in turn actuating the linkage 316.

Figure 18:
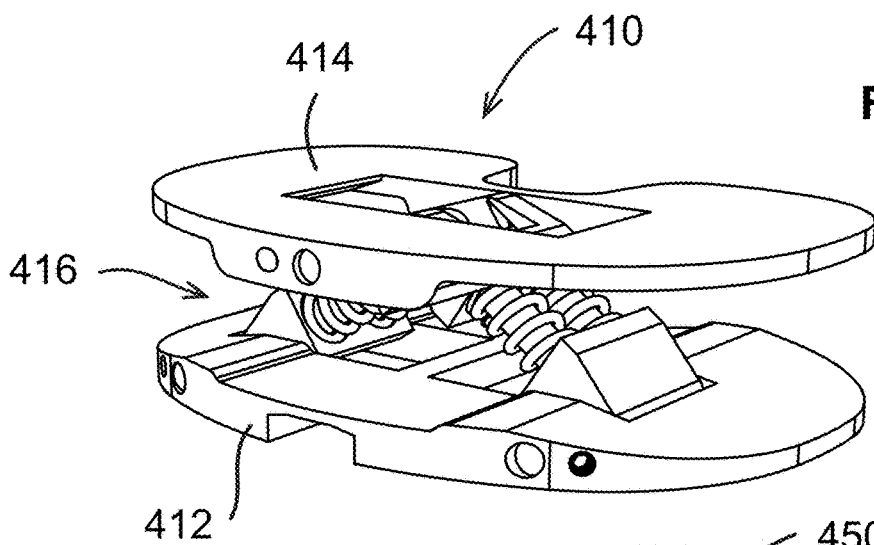
FIG. 18 is a schematic perspective view of an exemplary gap tensioner having a linkage incorporating variable-rate springs.
Figure 19:
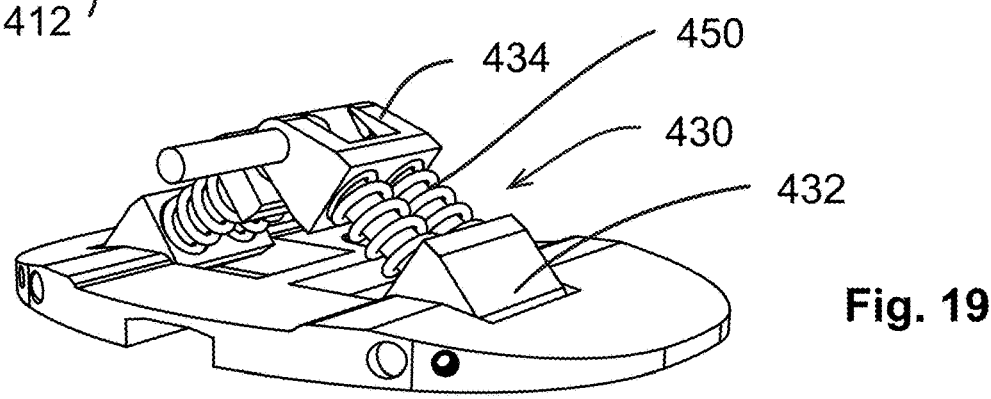
FIG. 19 is a schematic perspective view of the gap tensioner of FIG. 18 with a portion removed to show the linkage in more detail.

FIGS. 18 and 19 illustrate another exemplary gap tensioner 410. The gap tensioner 410 is similar in overall construction to the gap tensioner 10 described above. Elements of the gap tensioner 410 not explicitly described may be considered to be identical to corresponding elements of the gap tensioner 10.

The gap tensioner 410 includes a baseplate 412, top plate 414, and a linkage 416. The linkage 416 is configured as a pair of links 430 each having a lower end 432 pivotally connected to the baseplate 412. Upper ends 434 of the links 430 are pivoted to each other and to the top plate 414. Each of the links 430 is a telescoping assembly and is provided with one or more springs 450 which are arranged so as to urge the linkage 416 towards an extended position. The springs 450 may be configured to have a variable rate. In one example, the springs 450 and/or the geometry of the associated link 430 may be arranged to have a constant force-displacement characteristic. Stated another way, a force acting in the extension direction may be constant or substantially constant regardless of the position of the top plate 414. In this example, no actuating force is required to operate the device. To the contrary, the device may be compressed, placed in the working position, and then released to apply a working force.

Figure 20:
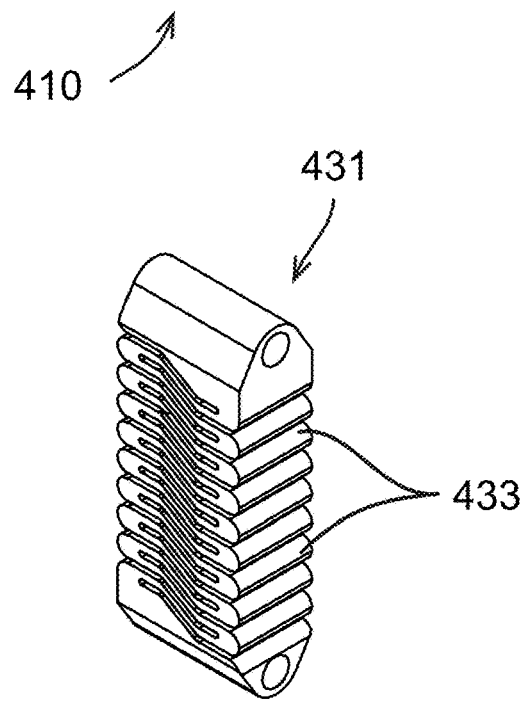
FIG. 20 is schematic perspective view of an alternative spring for use with the gap tensioner of FIG. 18.

FIG. 20 illustrates an alternative link 431 which may be substituted for the links 430. This link 431 has a plurality of spring members 433 formed therein and is a single integral, monolithic, or unitary element which serves as both a telescoping link and a spring.

Figure 21:
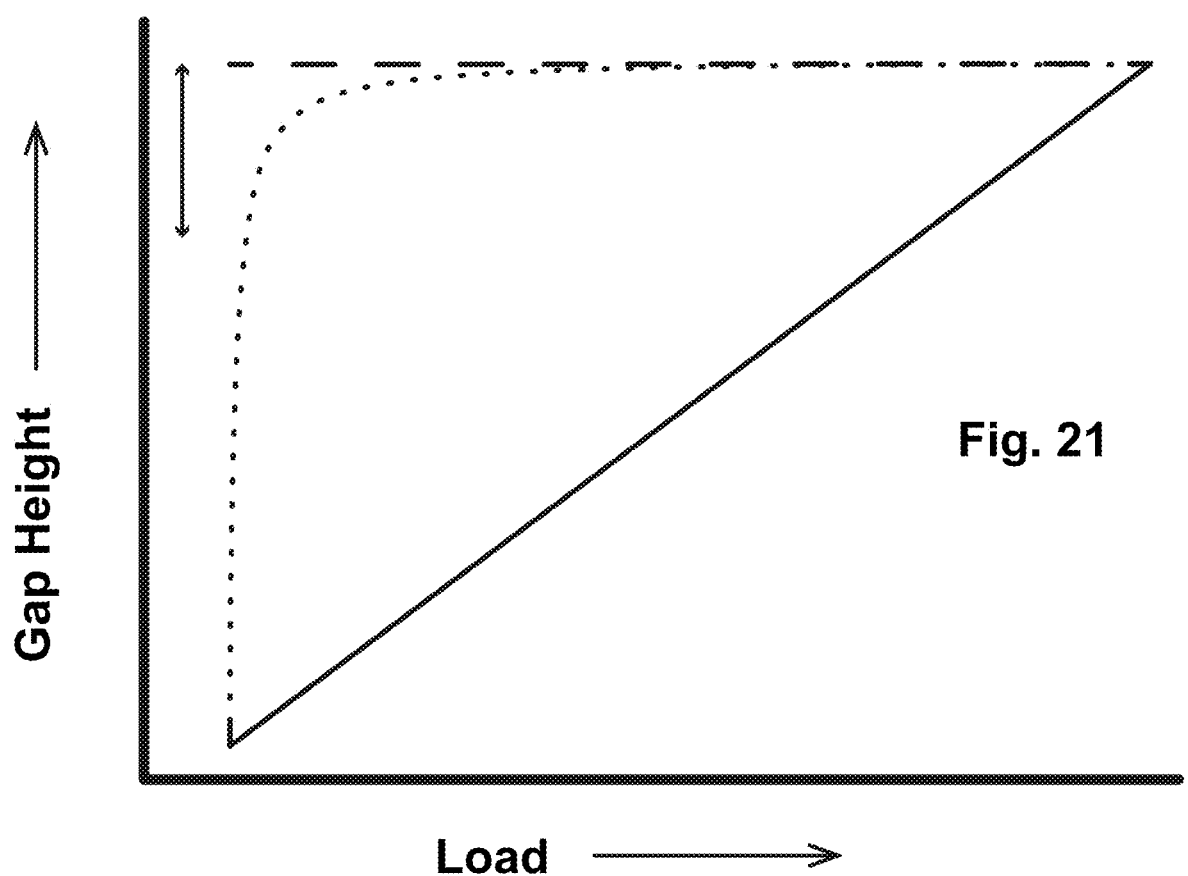
FIG. 21 is a graph illustrating the stress-strain properties of the ligaments in a human knee joint.
Figure 22:
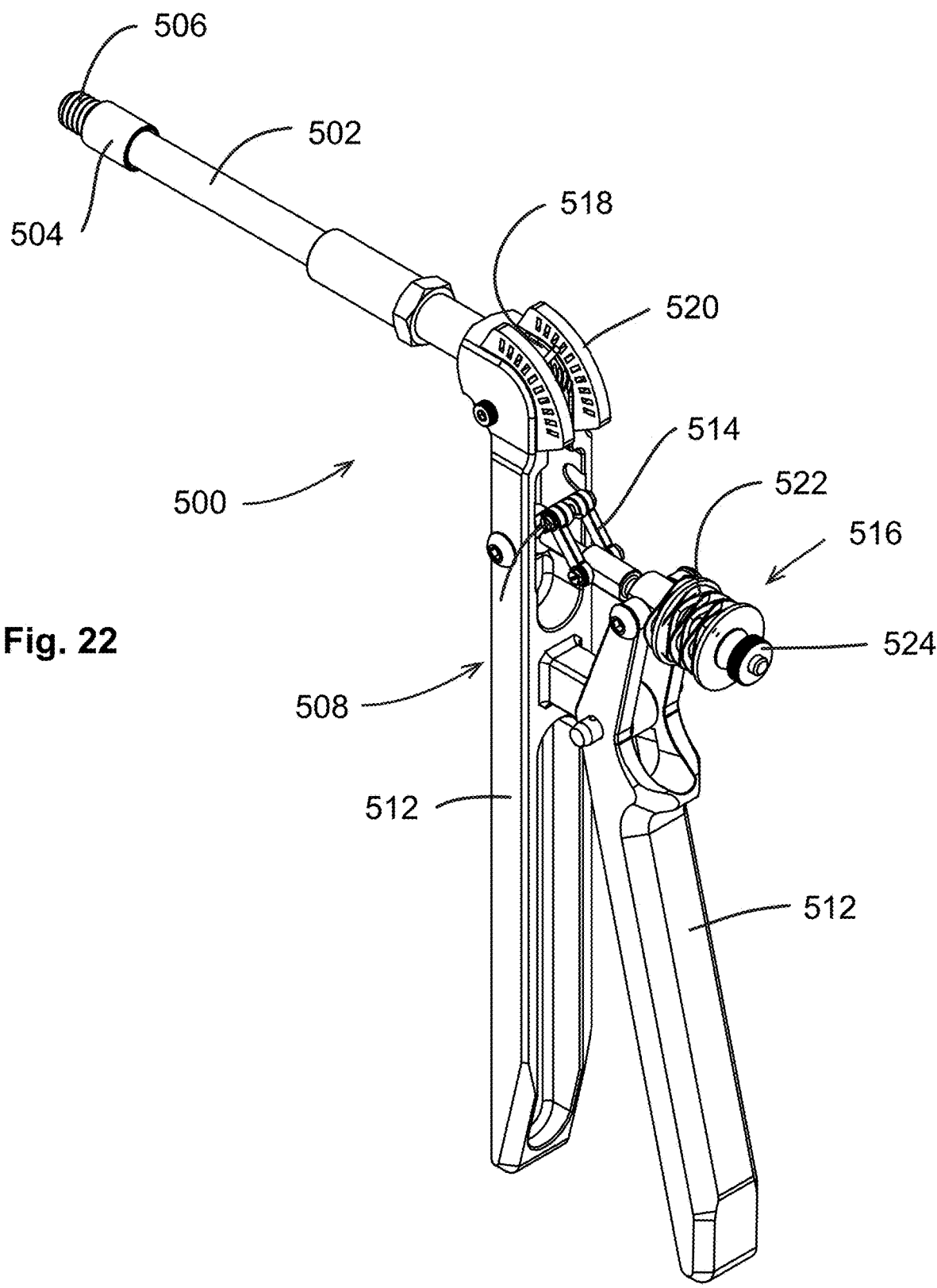
FIG. 22 is a perspective view of an exemplary actuating instrument.
Figure 23:
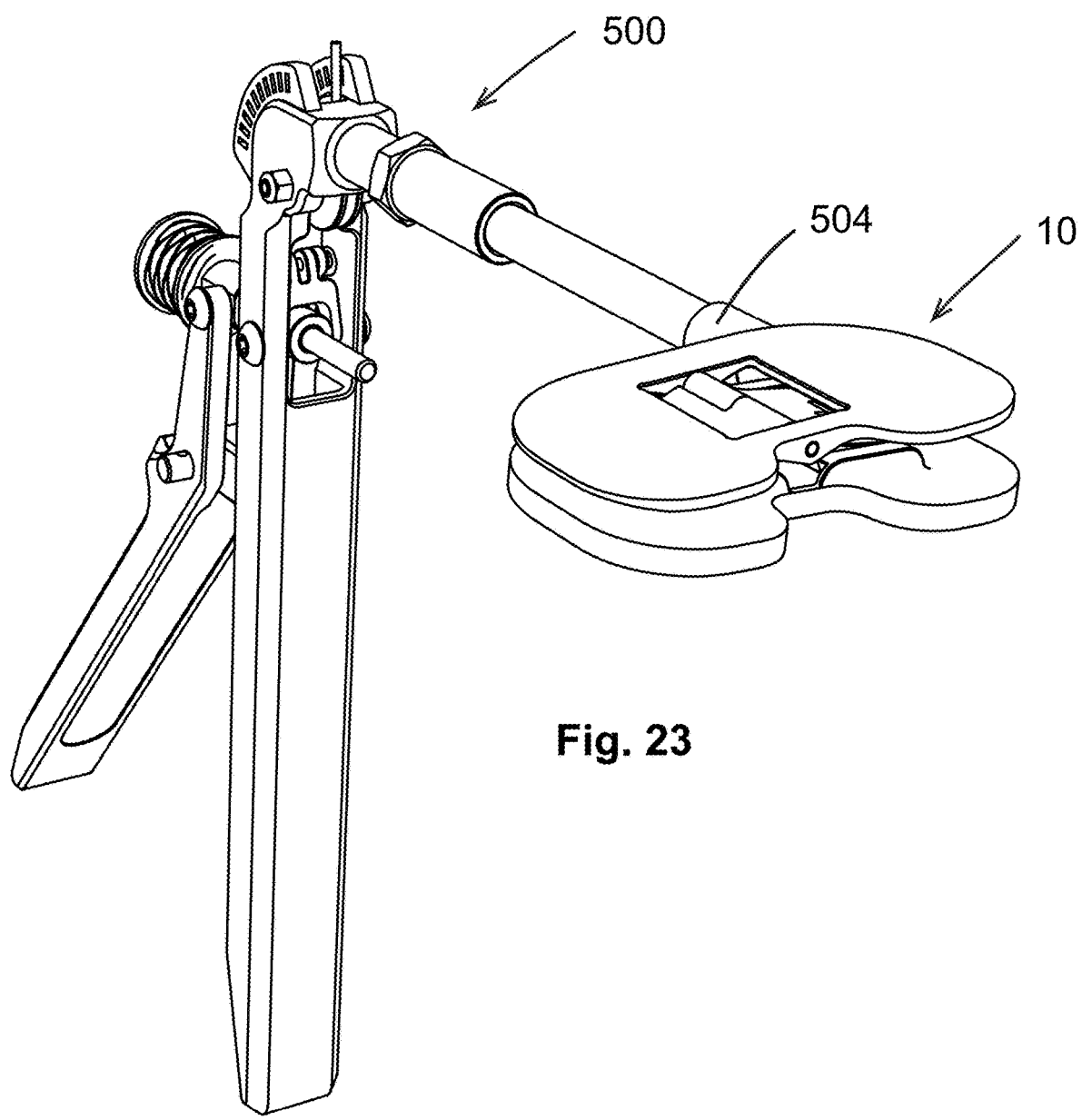
FIG. 23 is a perspective view of a gap tensioner coupled to the actuating instrument of FIG. 22.

As noted above, the gap tensioner 10 is useful for balancing the gap in a human knee joint when performing a total knee arthroscopy. The use of the gap tensioner 10 may be better understood by considering the characteristics of the human knee joint, particularly of the soft tissue (e.g. ligaments). FIG. 21 is a representative diagram of knee joint gap height versus applied extension load, similar to a stress-strain plot. In FIG. 21, the solid line is representative of properties of a perfectly elastic member (e.g. a rubber band). The dashed line is representative of the properties of a hypothetical infinitely rigid member. The dotted line is representative of the properties of a human knee joint ligament. It can be seen that the ligament is quite stiff and exhibits a low elongation to failure. The vertical portion of the dotted line indicates the range of motion where a minimal applied load will take up all available slack in the ligament. The slope of the gap height/load curve then rapidly transitions through the arcuate corner in the dotted line, to a very rigid characteristic. Given these properties, it will be apparent that the application of a relatively small load will ensure that the ligament is at full extension. In one example, an extension load of about 300 N or less may be applied. It will be understood that the chart in FIG. 21 is general in nature, and that specific ligaments in specific joints may have different magnitudes of slack available, or stated another way, the length of the vertical segment of the dotted line will vary from joint to joint and ligament to ligament. For example, in one patient's knee joint, all slack may be taken up at a relatively small gap height such as 9.5 mm. In another patient's knee joint, all slack may be taken up at a relatively larger height such as 20 mm.

Numerous instruments may be provided which are suitable for applying actuation loads of this magnitude to the gap tensioner 10, as well as indicating, measuring, or recording physical properties of the gap tensioner 10 such as position, applied load, and/or tilt position.

FIGS. 22-26 illustrate an exemplary actuating instrument 500 for use with the gap tensioner 10. The actuating instrument 500 includes a barrel 502. The distal end of the barrel 502 includes an instrument coupler 504 defining a second interface 506 complementary to the first interface 24 of the gap tensioner 10. In the illustrated example, the second interface 506 is configured as external threads.

The proximate end of the barrel 502 is connected to an actuating assembly 508 including a handle 510, a lever 512, and actuating linkage 514, and a load setting mechanism 516.

The actuating instrument 500 is configured to be coupled to the gap tensioner 10 by joining their mutual couplers 22, 504, to receive the cable 42 as described above (not shown), and to apply an actuating load, that is a tensile load, to the cable 42, thus actuating the gap tensioner 10.

The actuating instrument 500 may include some means for measuring or indicating displacement of the gap tensioner 10. In the illustrated example, the handle 510 carries a movable pointer 518 which pivots relative to a scale 520. The pointer 518 is arranged to contact or otherwise be driven by the cable in operation, thus driving pointer movement. The scale 520 may be calibrated to directly indicate the "gap height" (i.e. the distance between the tibial and femoral surfaces 18, 26) of the gap tensioner 10.

The lever 512 is pivoted to the handle 510 and coupled to the actuating linkage 514 and the load setting mechanism 516. Operation of the lever 512 causes the linkage 514 to apply tensile force to the cable 42 (not shown). The actuating force is applied through a spring element 522 which is a portion of the load setting mechanism 516. Preload of the spring element 522 may be set using an adjuster 524 such as the illustrated threaded knob. Accordingly, there is a definite adjustable force-displacement characteristic of the actuating instrument 500. The actuating linkage 514 has predetermined kinematic properties, or stated another way, the ratio of displacement of the cable 42 to input displacement of the lever 512 is known and can be plotted a graph, for the entire range of motion. The kinematic properties of the actuating linkage 514 can be configured to have a predetermined relationship to the kinematic properties of the linkage 16 of the gap tensioner 10 described above. In one specific example the kinematic properties of the actuating linkage 514 may be configured to have an inverse relationship to the kinematic properties of the linkage 16. That is, the ratios of input to output displacement for the linkage 514 and the linkage 16 would be inverse to each other for each position in the range of movement. This would result in a 1:1 output/input displacement ratio for the entire mechanical system. This may be referred to as the actuating instrument 500 and the gap tensioner 10 having "inverse kinematics" relative to each other. With such a relationship, the actuating instrument 500 would provide in essence no mechanical advantage. This has the result that a unit deflection of the lever 512 results in a unit deflection of the top plate 14, and a unit force applied to the lever 512 results in an equal unit force being applied to the gap tensioner 10.

Figure 24:
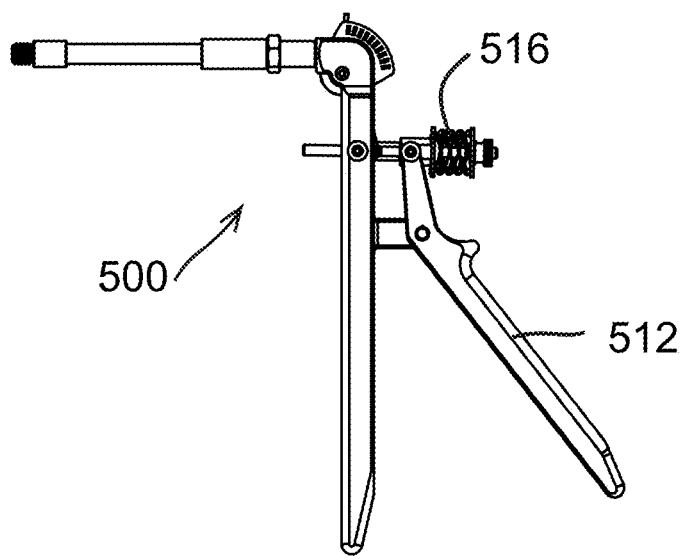
FIG. 24 is a side elevation view of the instrument of FIG. 22 in a retracted position.
Figure 25:
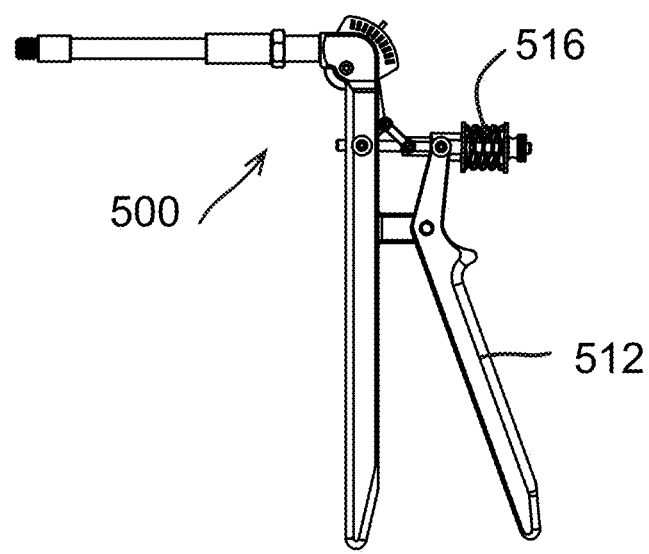
FIG. 25 is a side elevation view of the instrument of FIG. 22 in an extended, unloaded position.

Operation of the actuating instrument 500 is explained in more detail with reference to FIGS. 24-26. FIG. 24 shows the actuating instrument with the lever 512 in a released position. FIG. 25 shows the lever 512 in an intermediate position in which the cable is displaced and the gap tensioner 10 is partially extended, but no appreciable load is applied to the gap tensioner 10, other than overcoming friction and other minor forces. This corresponds generally to the vertical segment of the dotted line graph in FIG. 21.

Figure 26:
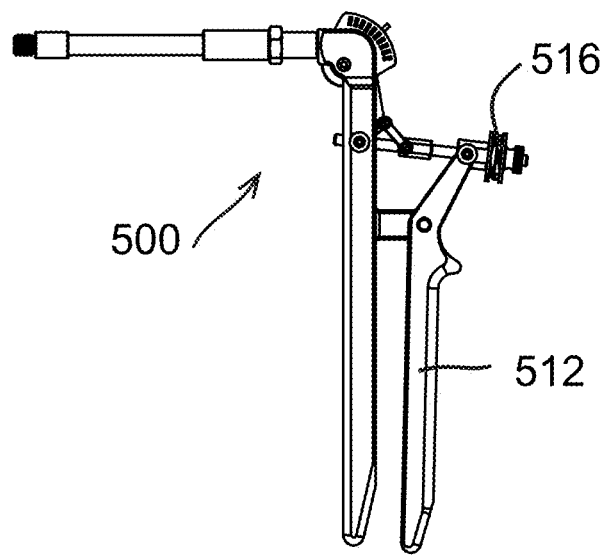
FIG. 26 is a side elevation view of the instrument in FIG. 22 in a tensioned position.
Figure 27:
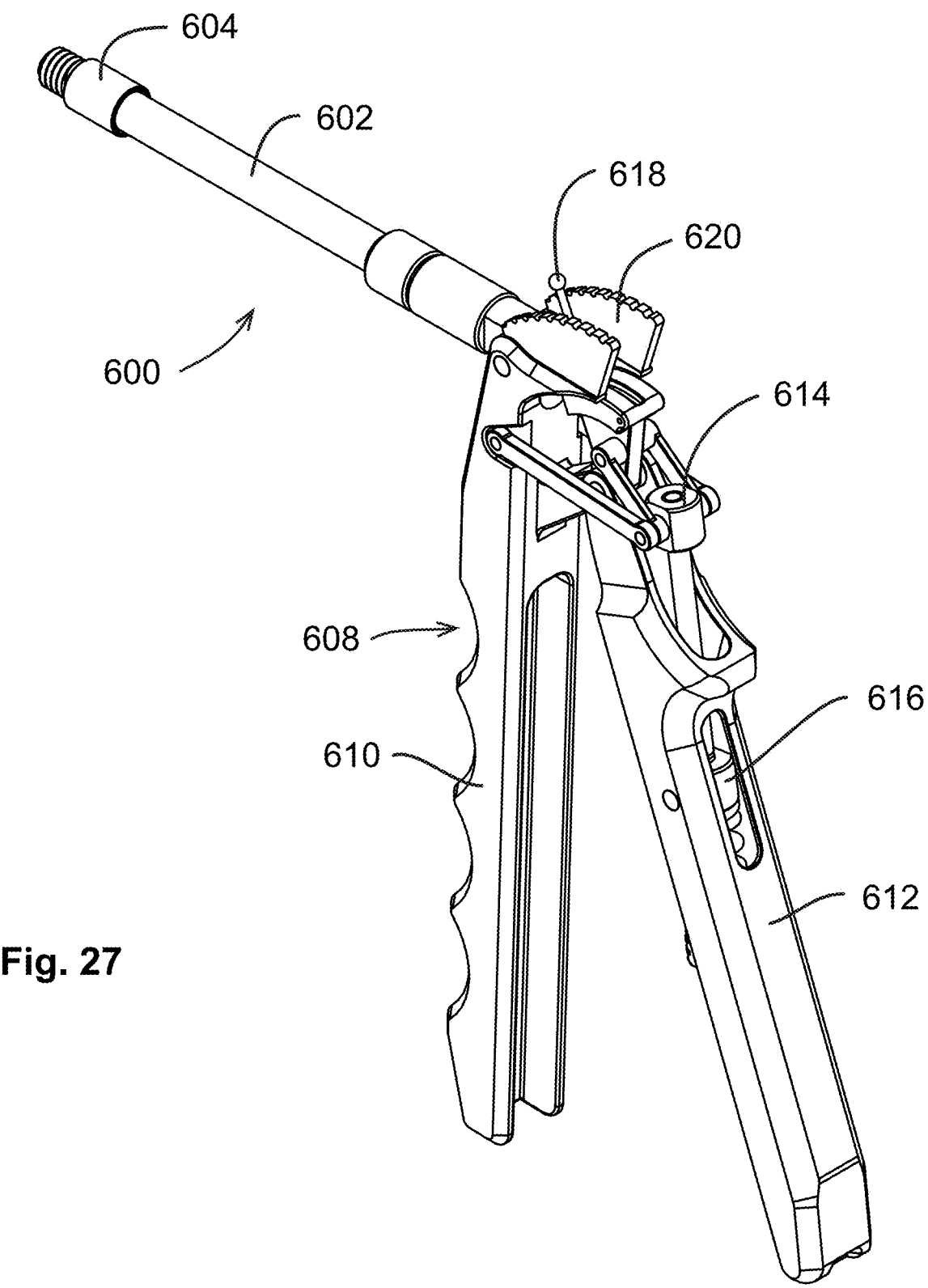
FIG. 27 is a perspective view of an exemplary actuating instrument.
Figure 28:
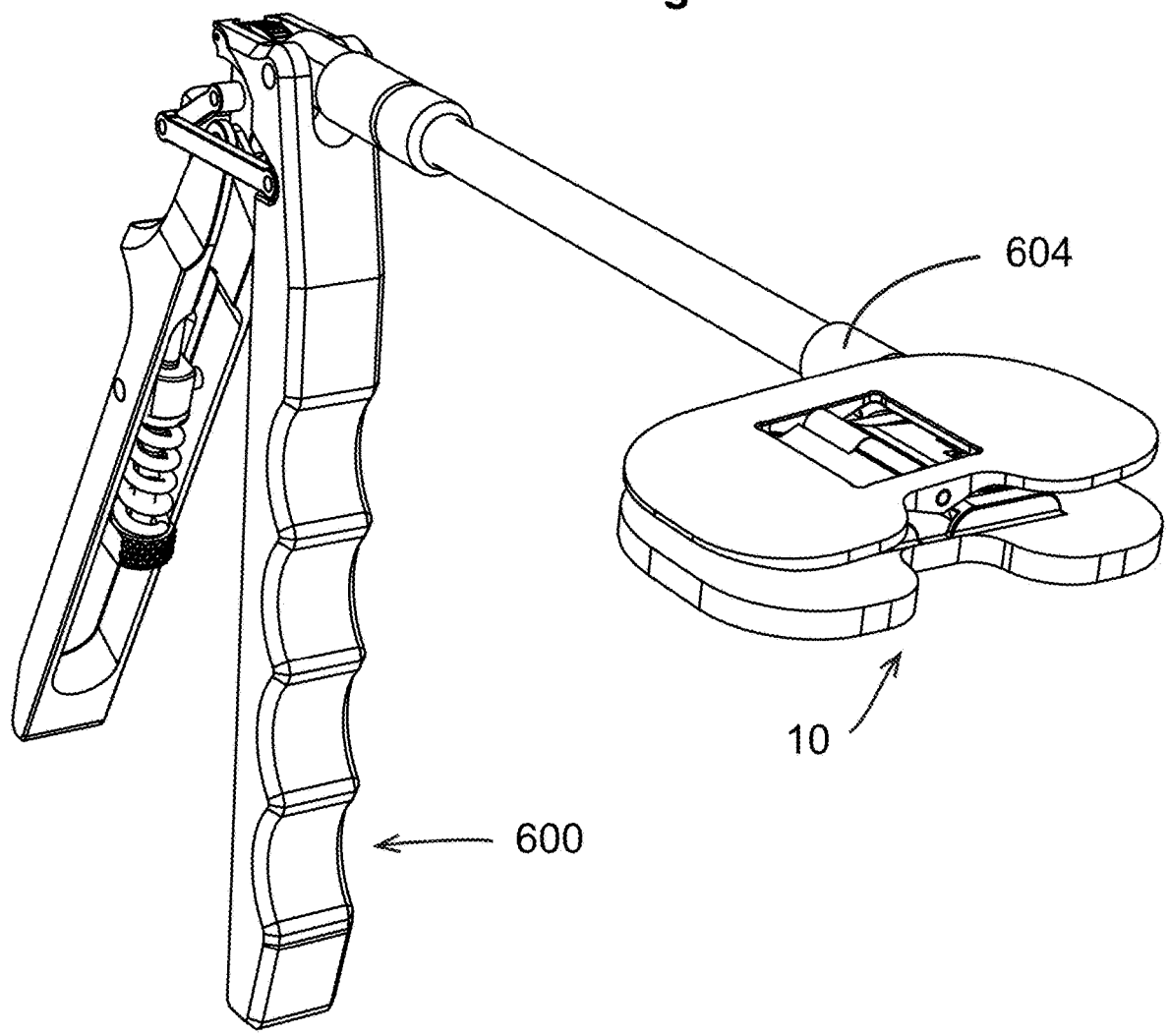
FIG. 28 is a perspective view of a gap tensioner coupled to the actuating instrument of FIG. 27.

FIG. 26 shows the lever 512 in a fully actuated position in which the cable is not displaced any further appreciable amount, but an actuating load (i.e. tension) is applied to the cable. It will be understood that the absolute position of the lever 512 relative to the body 510 when full preload is applied to the gap tensioner 10 will vary depending on the actual gap height. The load setting mechanism 516 allows the actuating load to be accurately displayed and/or controlled. For example, observation or measurement of the displacement of the spring element 522, with the spring rate being known, gives the force being applied. Alternatively, the adjuster 524 may be used to set the preload on the spring element 522 such that the desired actuating load is required to be applied in order to bring the spring element 522 to a known position, for example a fully compressed position.

FIGS. 27-31 illustrate another exemplary actuating instrument 600 for use with the gap tensioner 10. The actuating instrument 600 includes a barrel 602 with an instrument coupler 604 at its distal end. The proximate end of the barrel 602 is connected to an actuating assembly 608 including a handle 610, a lever 612, actuating linkage 614, and a load setting mechanism 616. The lever 612 carries a movable pointer 618 which pivots relative to a scale 620 in order to indicate displacement.

Figure 29:
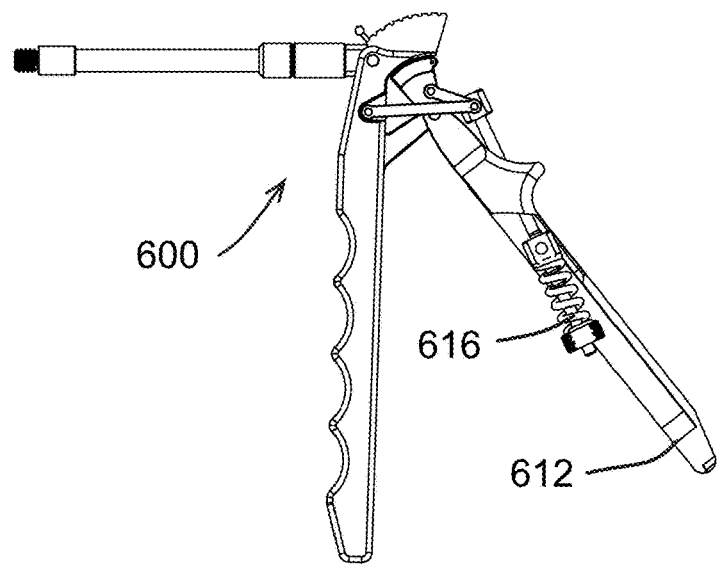
FIG. 29 is a side elevation view of the instrument of FIG. 27 in a retracted position.
Figure 30:
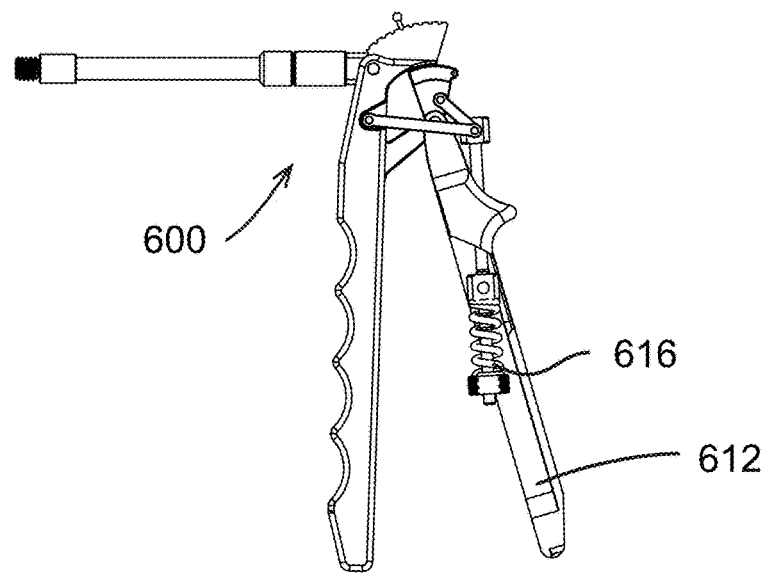
FIG. 30 is a side elevation view of the instrument of FIG. 27 in an extended, unloaded position.
Figure 31:
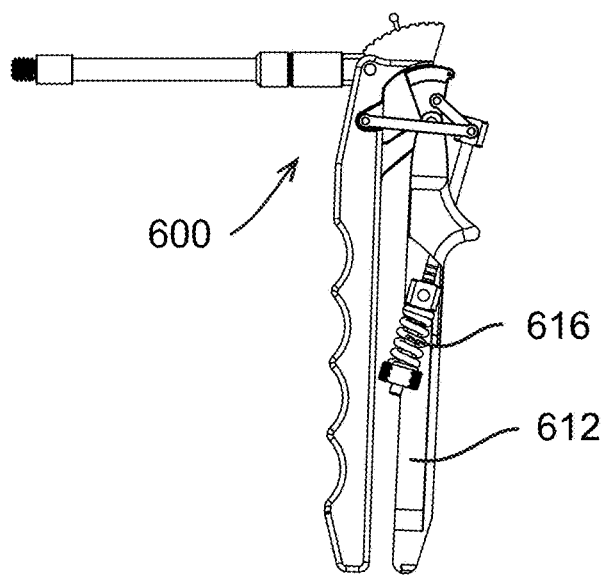
FIG. 31 is a side elevation view of the instrument in FIG. 27 in a tensioned position.
Figure 32:
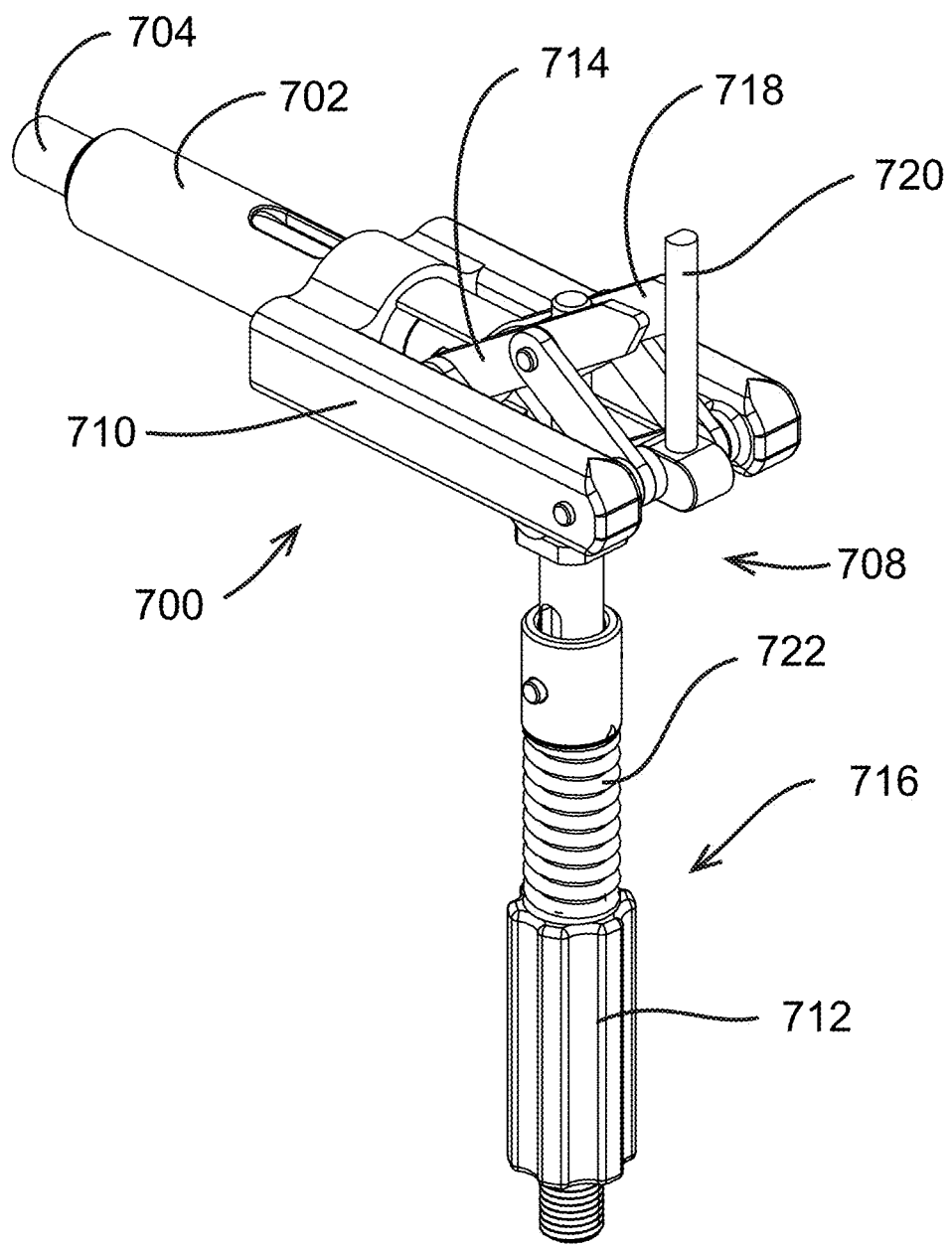
FIG. 32 is a perspective view of an exemplary actuating instrument.
Figure 33:
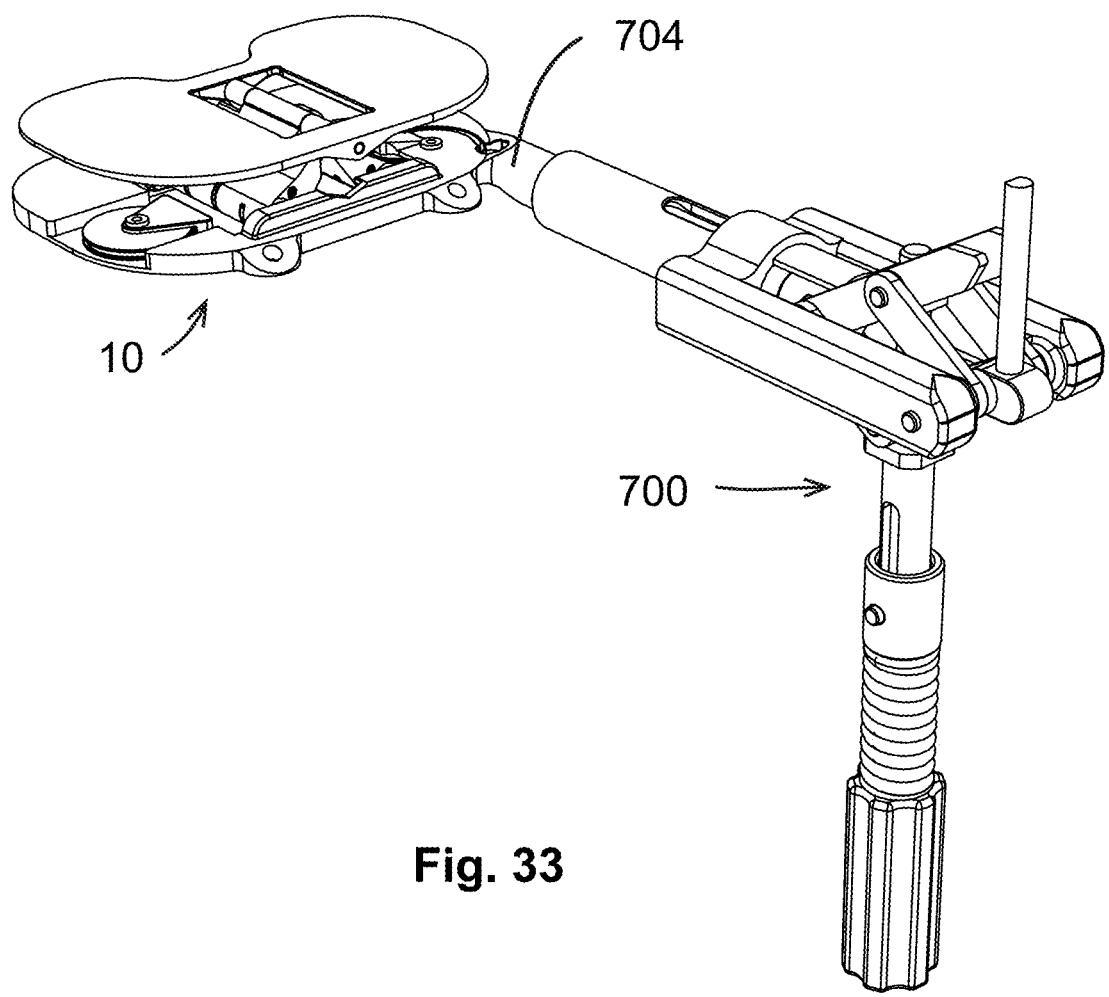
FIG. 33 is a perspective view of a gap tensioner coupled to the actuating instrument of FIG. 32.

Operation of the actuating instrument 600 is similar to that of the actuating instrument 500. As seen in FIGS. 29-31, the instrument 600 can be moved from a released position, through an extended but unloaded position, and finally to a fully actuated, loaded position as shown in FIG. 31.

FIGS. 32-36 illustrate another exemplary actuating instrument 700 for use with the gap tensioner 10. The actuating instrument 700 includes a barrel 702 with an instrument coupler 704 at its distal end. The proximate end of the barrel 702 is connected to an actuating assembly 708 including a body 710, a handle 712, actuating linkage 714, and a load setting mechanism 716. The device may include a movable indicator 718 which shows displacement against a scale 720. The linkage 714 is directly actuated by pressure of the load setting mechanism 716 which is set by the position of the handle 712. In this example, the handle 712 is a threaded member connected to a threaded rod.

Figure 34:
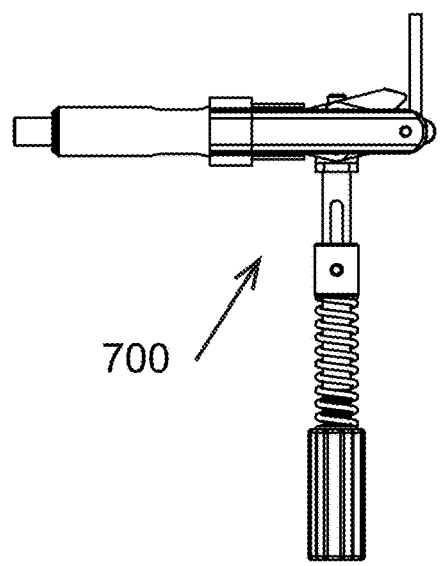
FIG. 34 is a side elevation view of the instrument of FIG. 32 in a retracted position.
Figure 35:
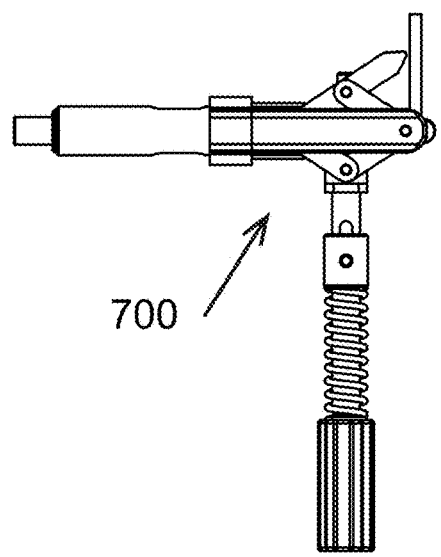
FIG. 35 is a side elevation view of the instrument of FIG. 32 in an extended, unloaded position.
Figure 36:
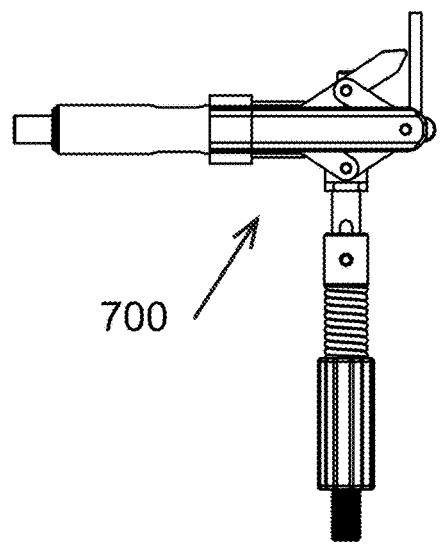
FIG. 36 is a side elevation view of the instrument in FIG. 32 in a tensioned position.

The actuating instrument 700 is operated by turning the handle 712, compressing the spring element 722 of the load setting mechanism 716, thus applying force to the linkage 714, which is translated to tension applied to the cable (not shown). Operation of the actuating instrument. As seen in FIGS. 34-36, the handle 712 can be rotated to vary compression of the spring element 722, moving the actuating instrument 700 from a released position, through an extended but unloaded position, and finally to a fully actuated, loaded position as shown in FIG. 36.

Figure 37:
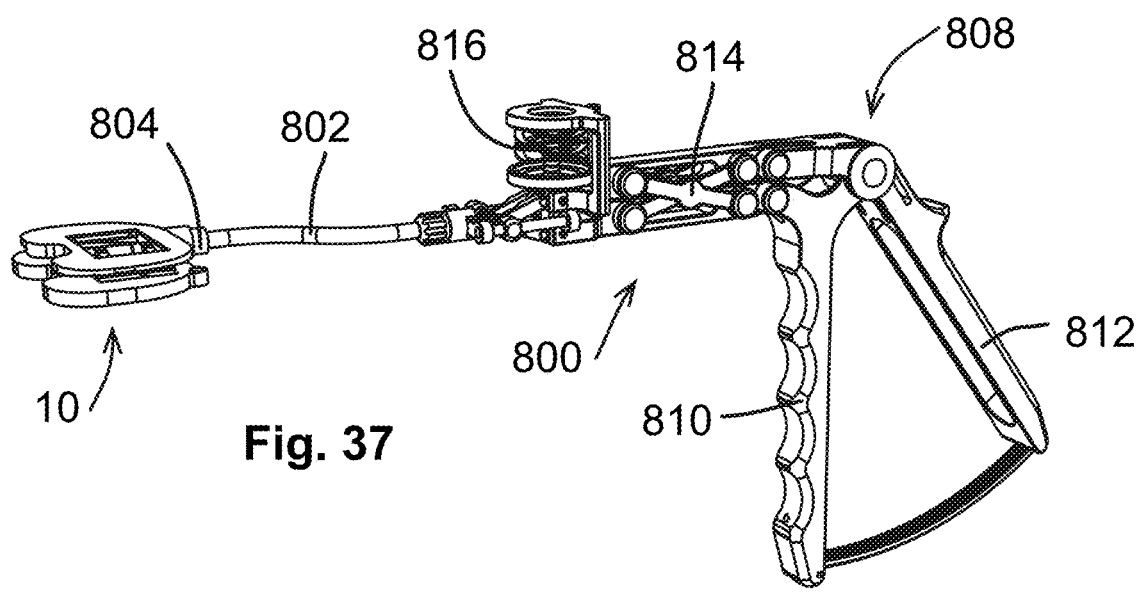
FIG. 37 is a perspective view of an exemplary actuating instrument in a retracted position.
Figure 38:
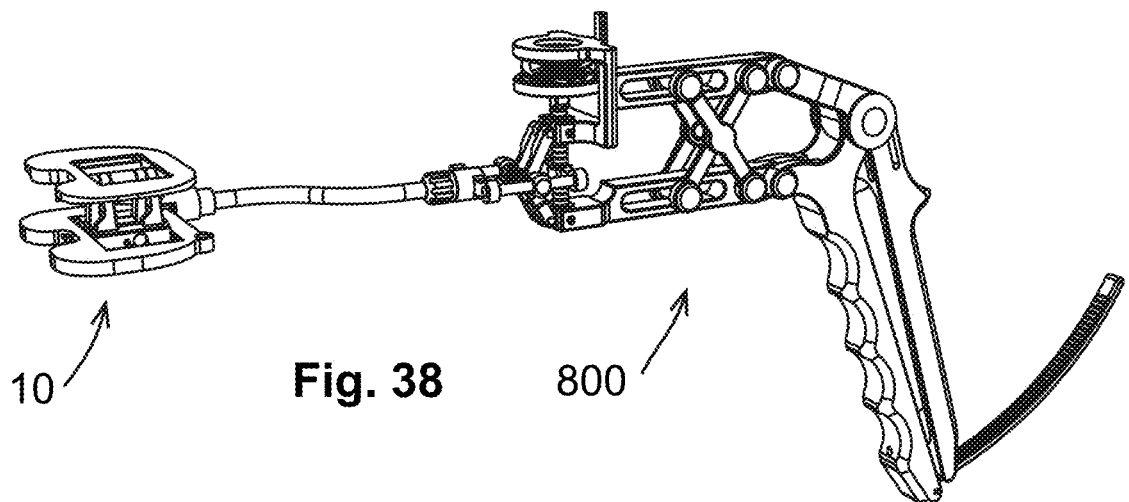
FIG. 38 is a perspective view of the actuating instrument of FIG. 37 in an extended position.
Figure 39:
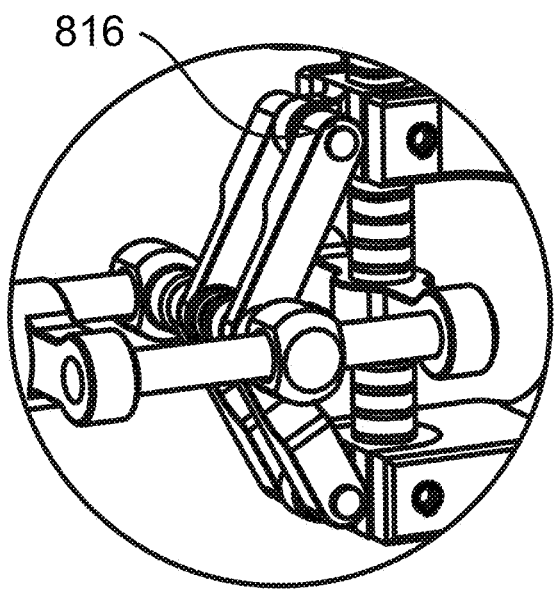
FIG. 39 is an enlarged view of a portion of FIG. 37.

FIGS. 37-39 illustrate another exemplary actuating instrument 800 for use with the gap tensioner 10. The actuating instrument 800 includes a barrel 802 with an instrument coupler 804 at its distal end. The proximate end of the barrel 802 is connected to an actuating assembly 808 including a handle 810, a lever 812, actuating linkage 814, and a load setting mechanism 816. Operation of the actuating instrument 800 is similar to that of the actuating instrument 500.

Figure 40:
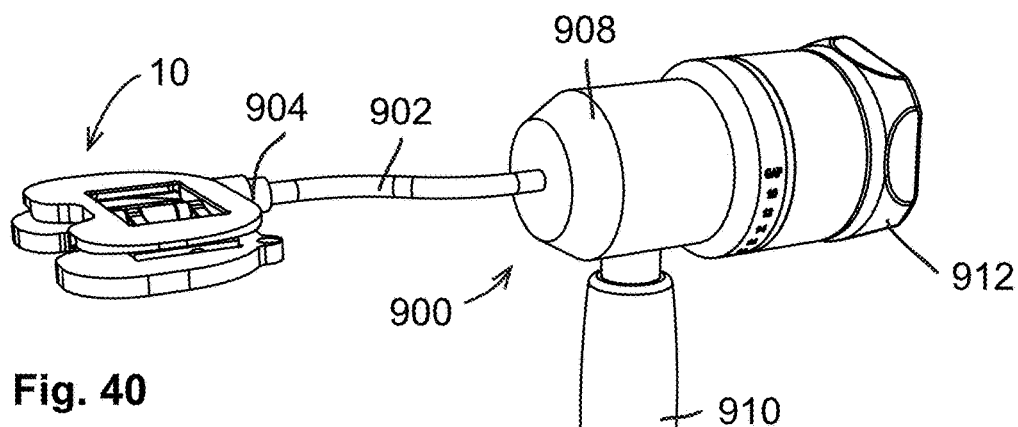
FIG. 40 is a perspective view of an exemplary actuating instrument coupled to a gap tensioner.
Figure 41:
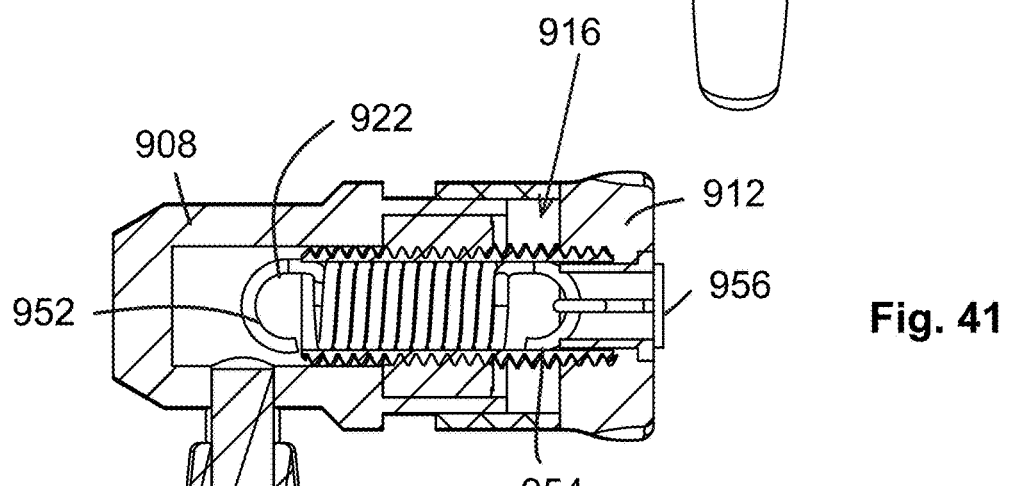
FIG. 41 is a cross-sectional view of the actuating instrument of FIG. 40.

FIGS. 40-41 illustrate another exemplary actuating instrument 900 for use with the gap tensioner 10. The actuating instrument 900 includes a barrel 902 with an instrument coupler 904 at its distal end. The proximate end of the barrel 902 is connected to a housing 908 including a handle 910, an operating knob 912, and a load setting mechanism 916.

Figure 42:
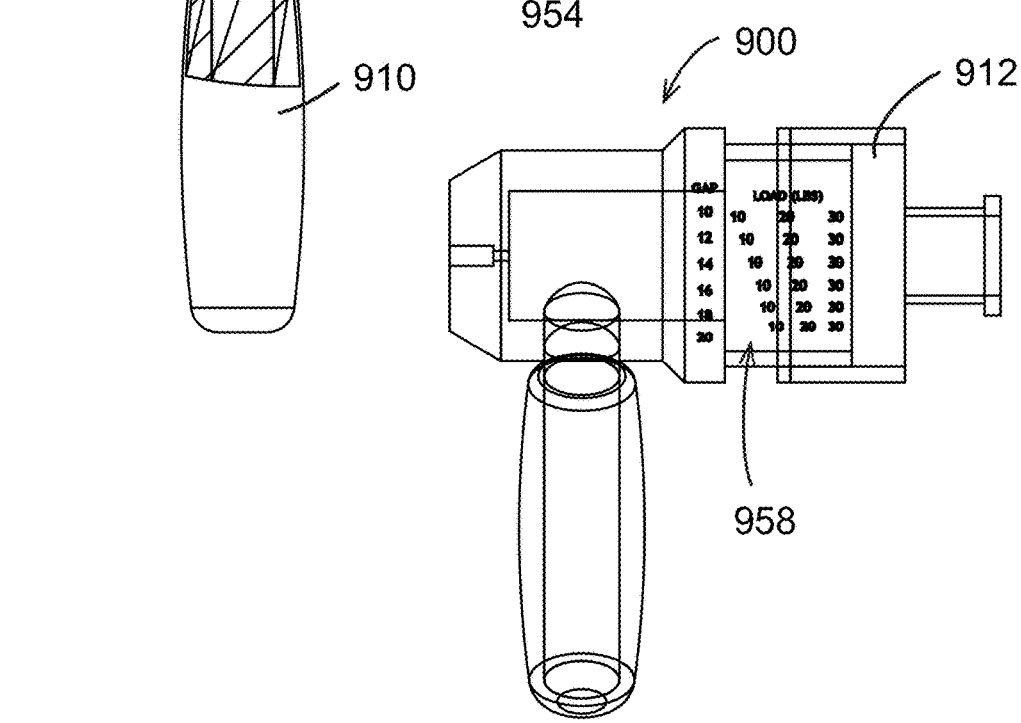
FIG. 42 is a side elevation view of the actuating instrument of FIG. 40.

The load setting mechanism 916 includes a spring element 922 having a first end 952 configured to be coupled to a cable (not shown) and a second end 954 connected to a threaded plug 956. The threaded plug 956 engages complementary threads of the operating knob 912. Rotation of the operating knob 912 causes a tensile load to be applied to the spring element 922. The tensile load is proportional to the displacement of the operating knob 912. As seen in FIG. 42, the housing 908 may be marked with a scale 958 which shows the applied actuating load for measured gap sizes.

Figure 43:
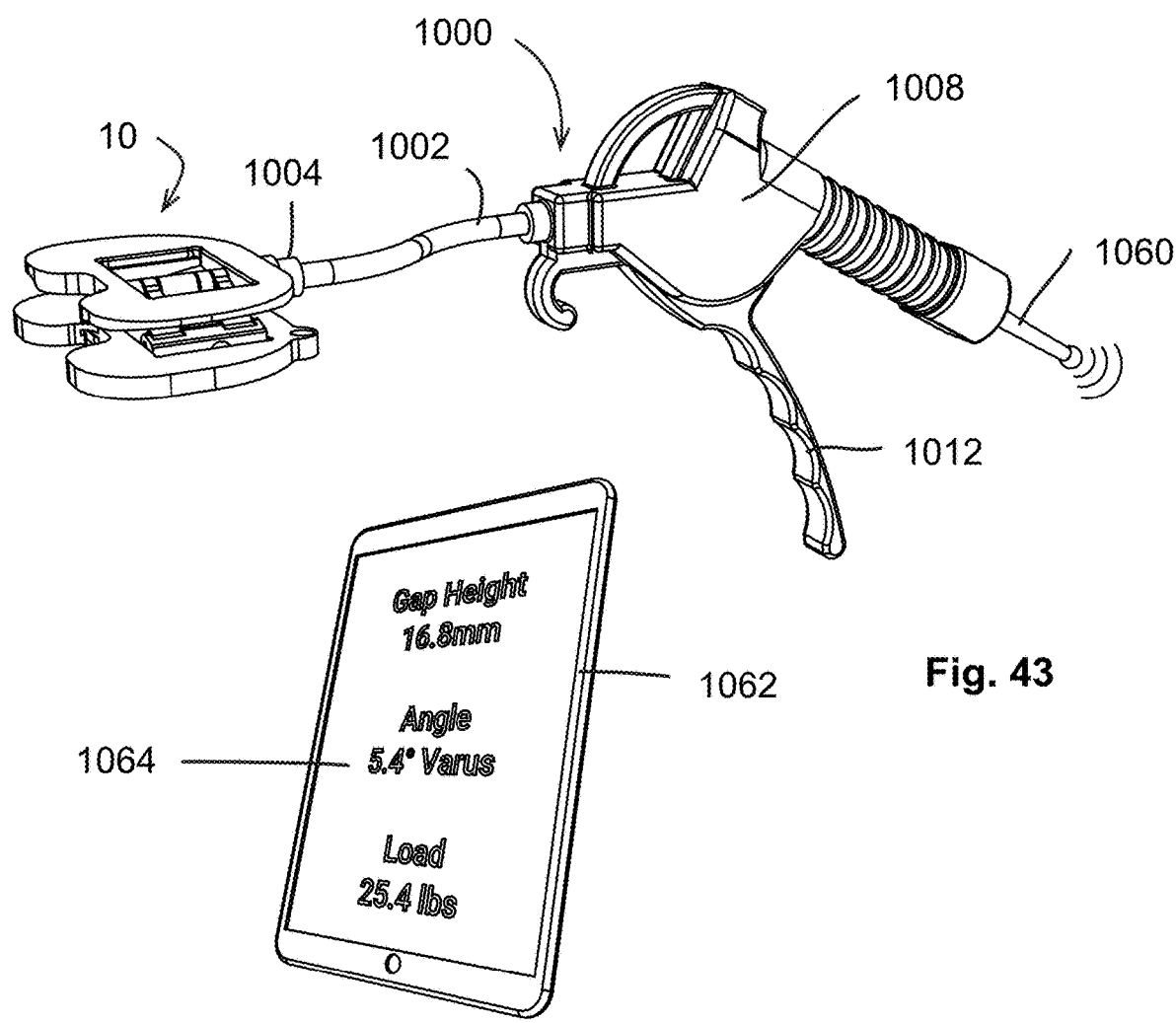
FIG. 43 is a perspective view of an exemplary actuating instrument coupled to a gap tensioner, in combination with a remote display.

FIG. 43 illustrates another exemplary actuating instrument 1000 for use with the gap tensioner 10. The actuating instrument 1000 includes a barrel 1002 with an instrument coupler 1004 at its distal end. The proximate end of the barrel 1002 is connected to an actuating assembly 1008 including a lever 1012. The interior of the actuating assembly 1008 includes an appropriate mechanism (not shown) such as an actuating linkage similar to those described above. The internal mechanism is operable to apply an actuating load to the gap tensioner 10 in response to movement of the lever 1012. The actuating instrument 1000 includes an electronic data transmitter, shown schematically at 1060. The transmitter 1060 may operate over a wired or wireless connection. The actuating instrument 1000 and/or the tensioner 10 are supplied with an appropriate combination of transducers (not shown) to detect physical properties such as force, tilt angle, and/or applied load and generate a signal representative thereof. For example, the tensioner 10 may be provided with sensors operable to detect the magnitude of extension (i.e. "gap height"), the angle of the top plate about the pivot axis (i.e. varus/valgus), and/or the applied force in the extension direction. Nonlimiting examples of suitable transducers include strain gages, load cells, linear variable differential transformers ("LVDT"), rotary variable differential transformers ("RVDT"), or linear or rotary encoders or resolvers. (Alternatively, the gap tensioner 10 may be provided with simple visual scales, not shown, for displacement/gap height and/or tilt angle, or may include a mechanical linkage, not shown, which can transmit movement representative of tilt angle to a mechanical or electronic actuating instrument). The transmitter 1060 is operable to transmit the signal. A remote display 1062 is configured to receive the signal and produce a display 1064 of the transducer data. As one example, the remote display 1062 may be embodied in a conventional portable electronic device such as a "smart phone" or electronic tablet with suitable software programming.

In use, the remote display 1062 permits the surgeon to observe the physical properties of the gap tensioner 10 in real time as the actuating instrument 1000 is used to operate the gap tensioner 10.

Figure 44:
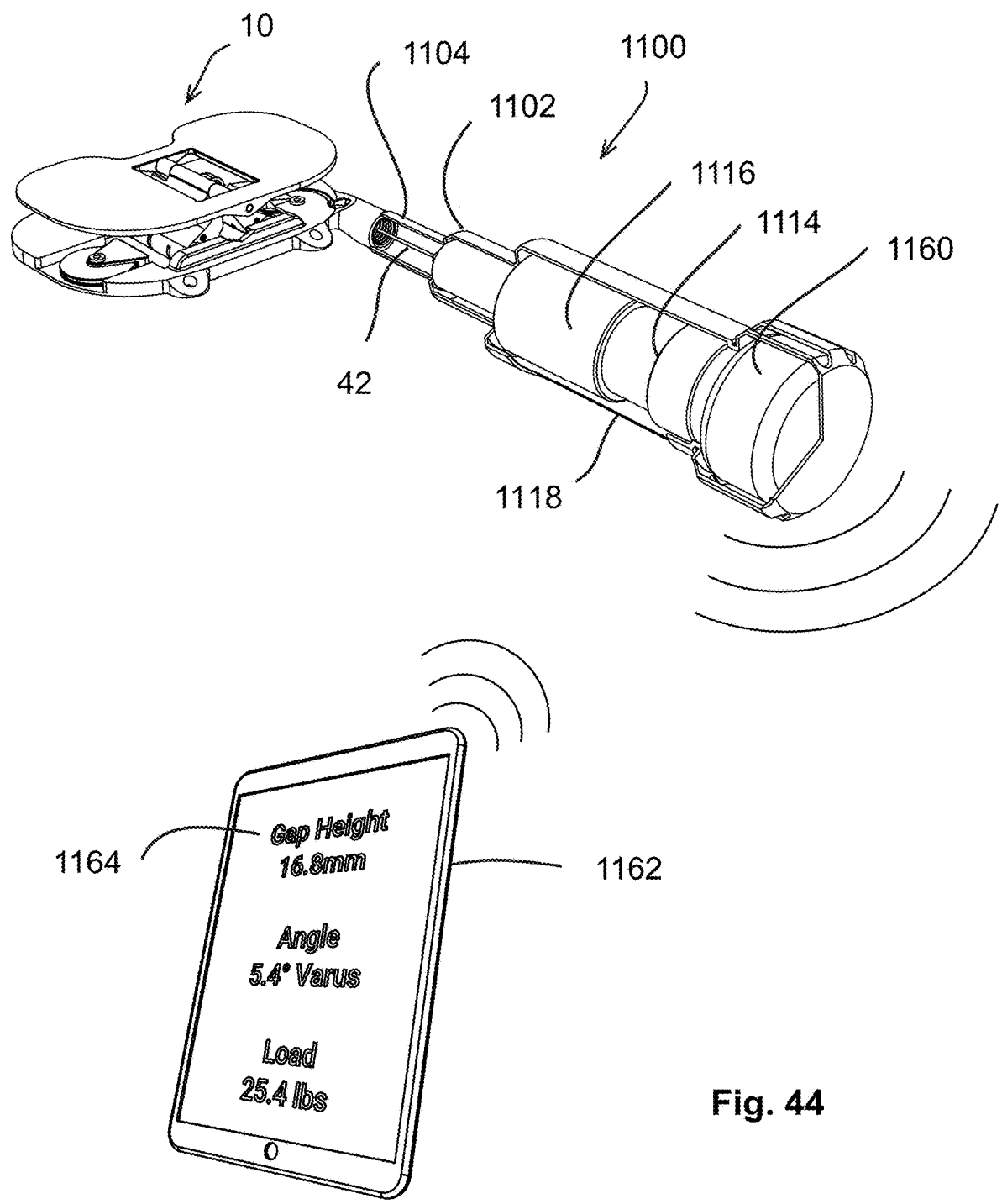
FIG. 44 is a perspective view of an exemplary actuating instrument coupled to a gap tensioner, in combination with a remote display.

FIG. 44 illustrates another exemplary actuating instrument 1100 for use with the gap tensioner 10. The actuating instrument 1100 includes a barrel 1102 with an instrument coupler 1104 at its distal end. The proximate end of the barrel 1102 is connected to an actuating assembly 1118. The interior of the actuating assembly 1118 includes an appropriate driving mechanism such as an electrically-powered linear actuator 1114. The driving mechanism 1114 is operable to apply an actuating load to the gap tensioner 10, through cable 42. The actuating instrument 1100 includes an electronic data transmitter, shown schematically at 1160, and may include an appropriate electrical power source such as a battery (not shown). The transmitter 1160 may operate over a wired or wireless connection. The actuating instrument 1110 and/or the gap tensioner 10 are supplied with an appropriate combination of transducers as described above with respect to actuating instrument 1000, such as force transducer 1116, to detect one or more physical properties of the gap tensioner 10 and generate a signal representative thereof. The transmitter 1160 is operable to transmit the sensor signal. A remote display 1162 is configured to receive the signal and produce a display 1164 of the transducer data. As one example, the remote display 1162 may be embodied in a conventional portable electronic device such as a "smart phone" or electronic tablet with suitable software programming.

In use, the remote display 1162 permits the surgeon to observe the physical properties of the gap tensioner 10 in real time as the actuating instrument 1100 is used to operate the gap tensioner 10 Optionally, the actuating instrument 1100 may incorporate a tracking marker 1162. It includes one or more tracking points (not individually illustrated) which may be configured as transmitting antennas, radiological markers, or other similar devices. Using an appropriate receiving device, described in more detail below, the position and orientation of the receiving device to the tracking marker 1162 may be determined by receipt and analysis at the receiving device of signals transmitted by the tracking marker 1602.

Figure 45:
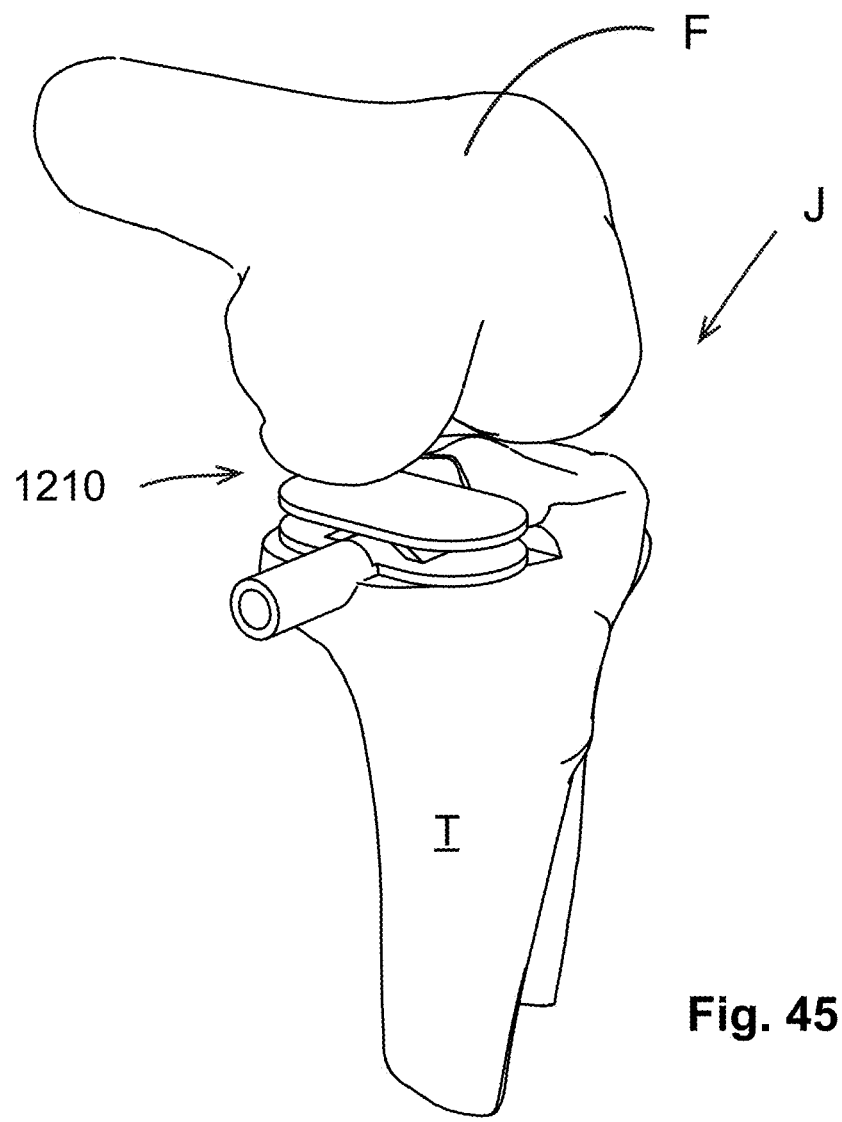
FIG. 45 is a perspective view of a human knee joint showing an alternative gap tensioner inserted therein.

In the example described above, the gap tensioner 10 is intended to be used for a total knee arthroscopy and is sized and shaped to be inserted into the human knee joint into span the entire gap across both condyles. Other configurations are possible. For example, FIG. 45 shows an alternative gap tensioner 1210 inserted between the tibia T and femur F of a human knee joint J. It can be seen that one condyle of the tibia has been cut away and that the gap tensioner is sized and configured to be inserted into the gap above the cutaway condyle, from the medial aspect of the joint.

Figure 46:
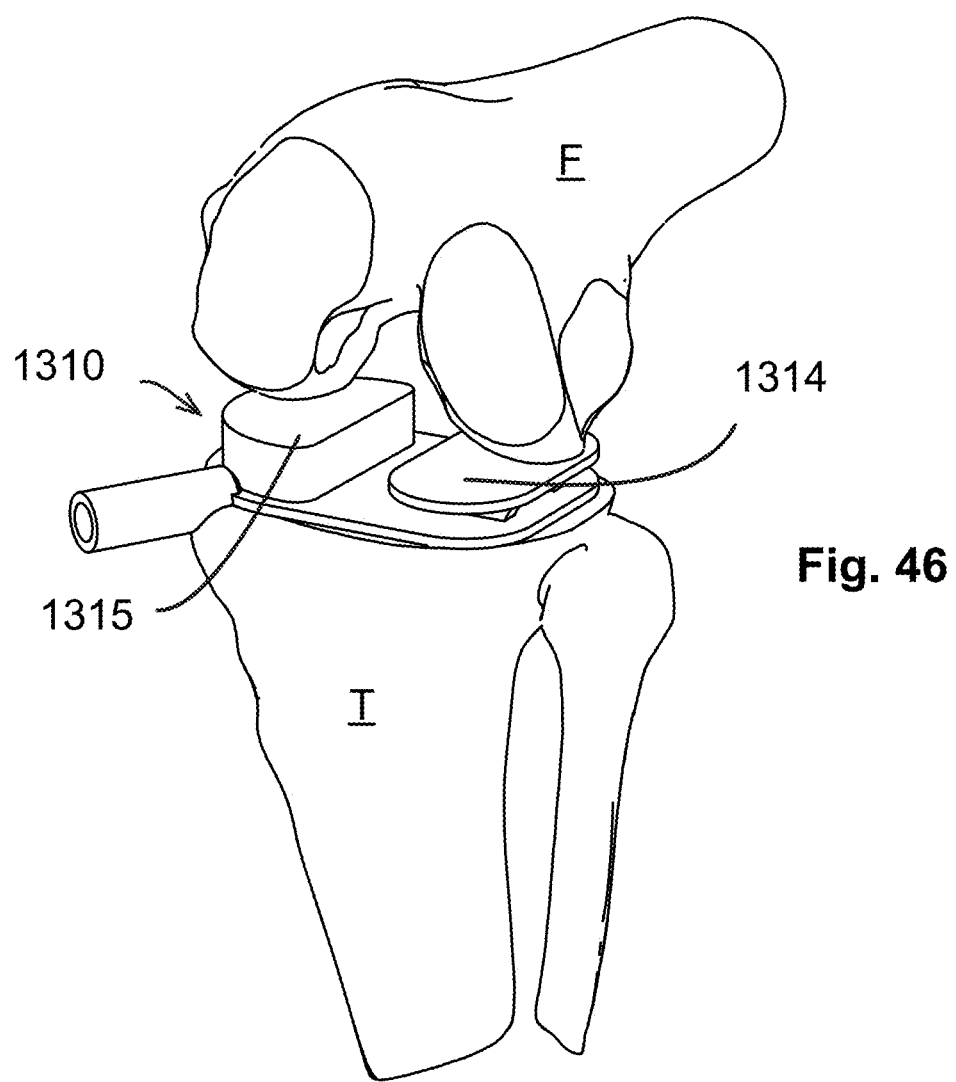
FIG. 46 is a perspective view of the human knee joint showing another alternative gap tensioner inserted therein.

FIG. 46 shows another alternative gap tensioner 1310 which has one movable top plate 1314 positioned under one condyle and one fixed block 1315 positioned under the other condyle.

Figure 47:
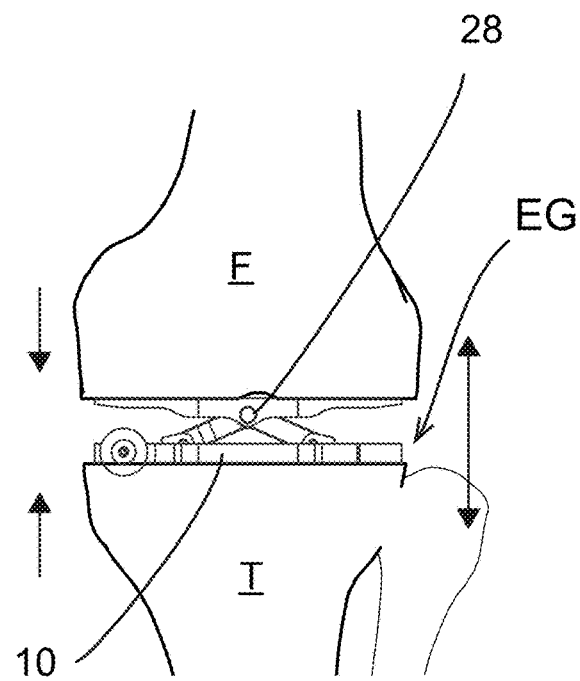
FIG. 47 is view of the interior aspect of the human knee joint having a gap tensioner inserted therein.
Figures 48, 49:
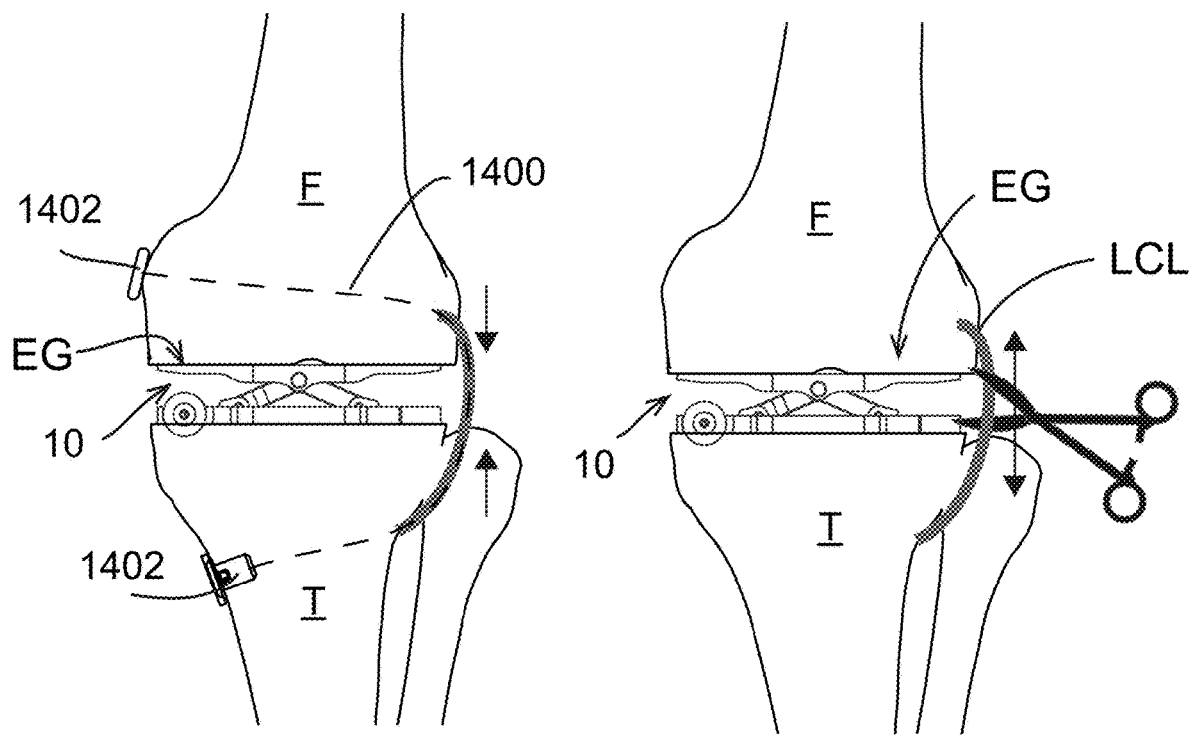
FIG. 48 is a view of the anterior aspect of a human knee joint illustrating the process of augmenting a ligament thereof.
FIG. 49 is a view of the anterior aspect of the human knee joint illustrating the process of releasing a ligament thereof.
Figure 76:
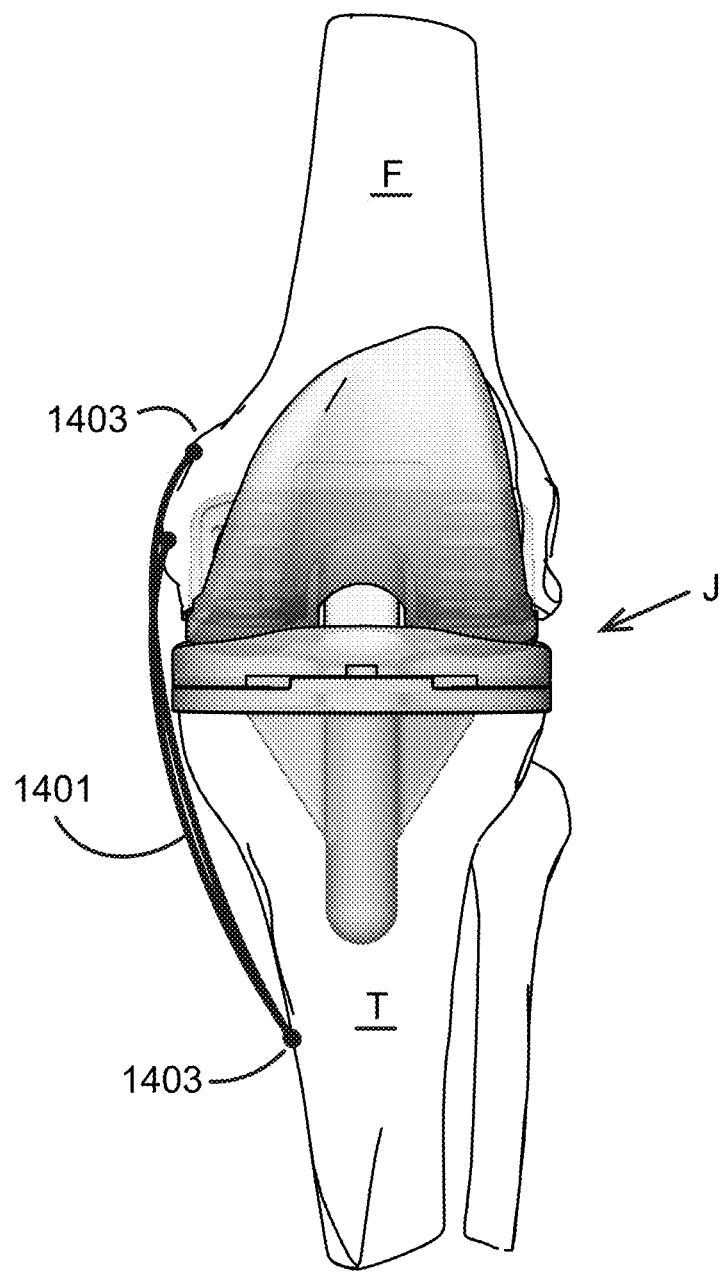
FIG. 76 is a view of the anterior aspect of a human knee joint illustrating an alternative process of augmenting a ligament thereof.
Figure 77:
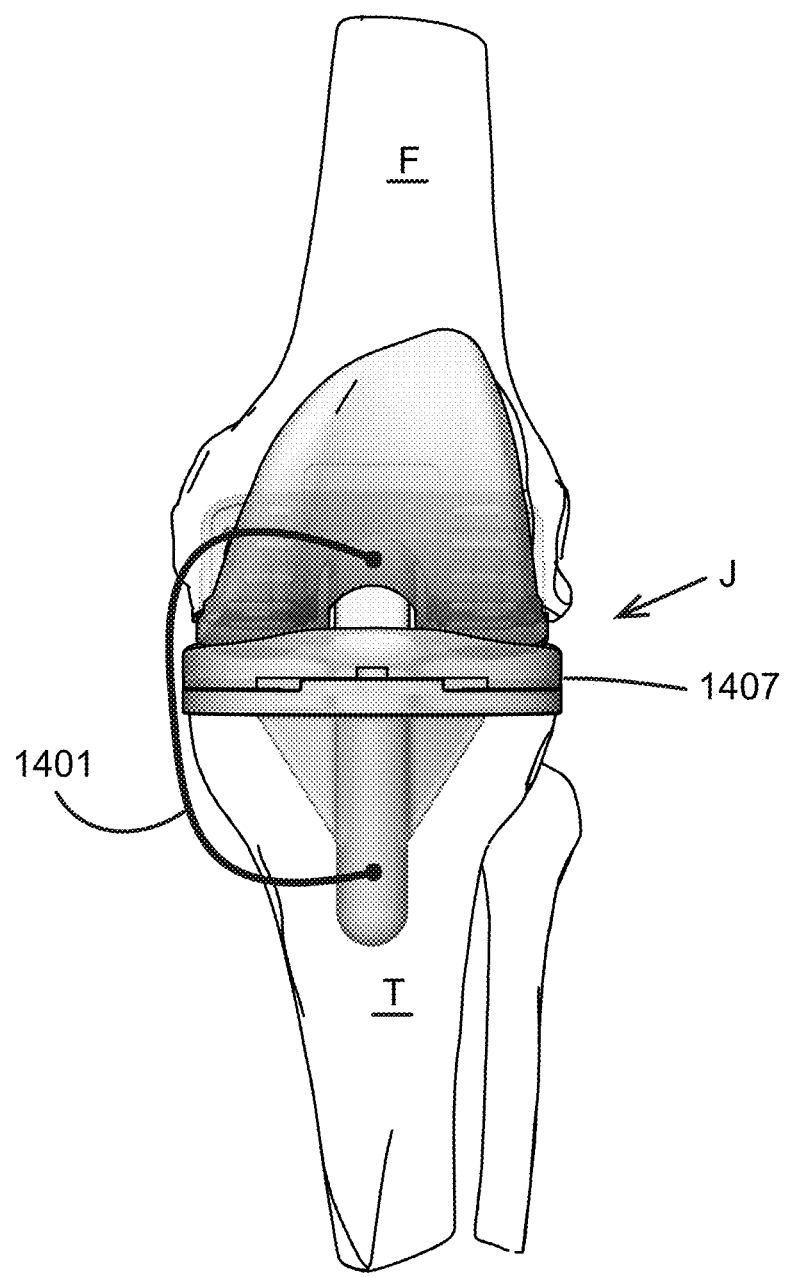
FIG. 77 is a view of the anterior aspect of a human knee joint illustrating an alternative process of augmenting a ligament thereof.
Figure 80:
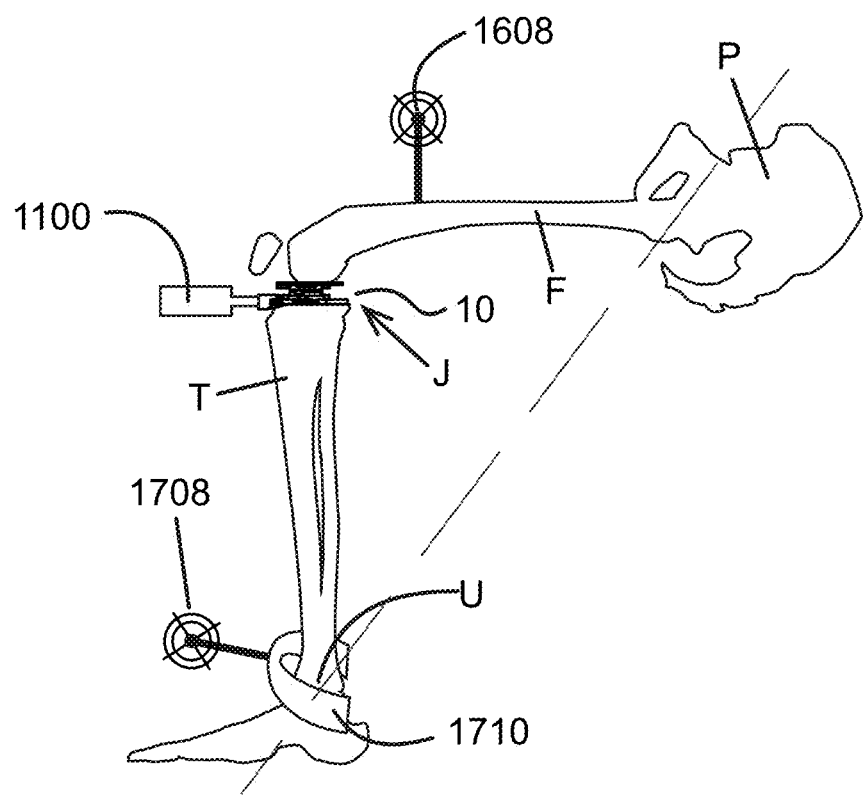
FIG. 80 is a view of a medial aspect of the human leg of FIG. 78 in flexion, with a gap tensioner inserted in the knee joint and tracking markers attached thereto.

The gap tensioner 10 is especially useful for adjusting the soft tissue lateral tension balance of a human knee joint. Referring to FIG. 47, a gap tensioner 10 is shown inserted in an extension gap EG between the femur F and the tibia T. The gap tensioner 10 pivots freely about pivot axis 28 as described above. The tilt angle of the top plate 14 may be manipulated by selective augmentation and/or release of the lateral collateral ligament or of the medial collateral ligament. FIG. 48 illustrates a process of augmentation in which an artificial tensile member 1400 secured with anchors 1402 is passed through the femur F and tibia T, spanning the lateral aspect of the extension gap. The term "anchor" as it relates to element 1402 refers to any device which is effective to secure a tensile member 1400 passing therethrough. Nonlimiting examples of anchors 1402 and include washers, screw plates, ferrules, and swage or crimp anchors. Properly tensioned, this tensile member 1400 replaces or augments tension provided by the natural lateral collateral ligament. The augmentation shown in FIG. 48 is transosseous, but other forms of augmentation are possible. For example, FIG. 76 illustrates a process of augmentation in which an artificial tensile member 1401 secured with anchors 1403 spans the lateral aspect of the knee joint J. The tensile member 1401 may have both ends anchored directly to the femur F and tibia T. Alternatively, as seen in FIG. 77, the tensile member 1401 may have its ends anchored to the components of a knee arthroplasty 1407, which components are in turn anchored to the femur F and tibia T. As yet another alternative (not shown), one end of a tensile member may be anchored directly to the femur F or tibia T, with the other end indirectly anchored, for example it may be anchored to an arthroplasty element which is in turn anchored directly to the opposite bone of the joint. As yet another alternative, a tensile member may be anchored directly or indirectly to the fibula. FIG. 49 illustrates a process of release in which a ligament (in this example the lateral collateral ligament LCL) is partially severed to release tension thereon. Either action, augmentation or release, would change the balance of tension acting on the joint J and thus change the tilt angle (varus or valgus).

Figure 50:
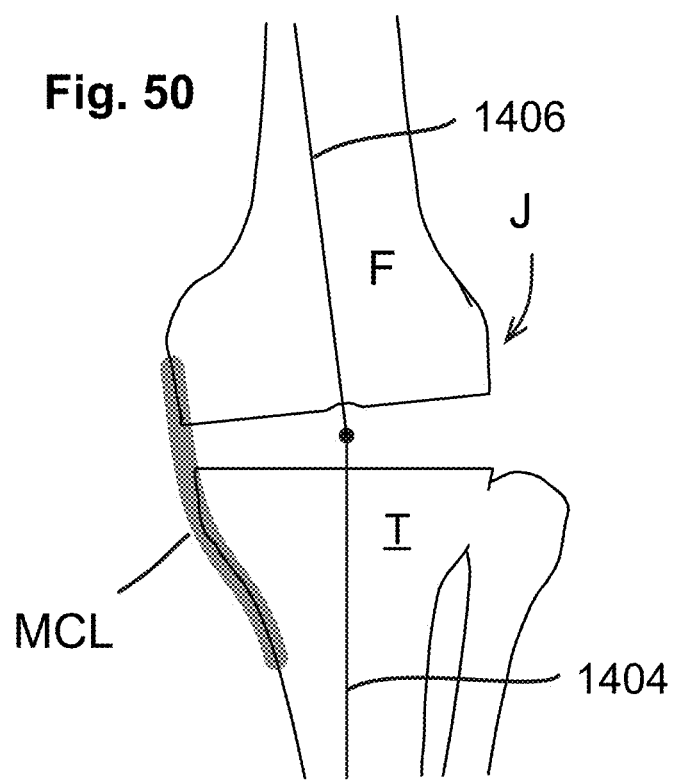
FIG. 50 is a view of the anterior aspect of the human knee joint having a varus angulation.
Figure 51:
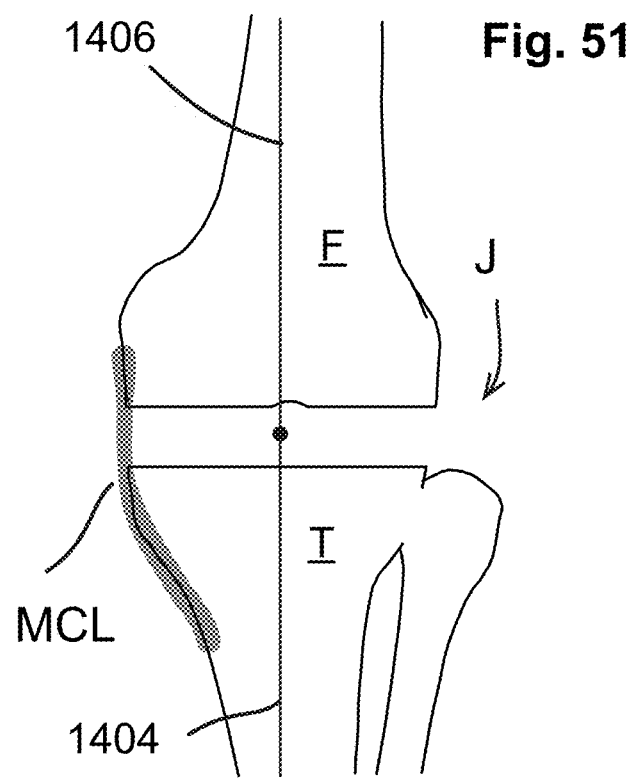
FIG. 51 is a view of the anterior aspect of the joint of FIG. 50, showing correction of the varus angulation through release of the medial collateral ligament.

FIGS. 50 and 51 illustrate how the tilt angle (varus or valgus) may be manipulated. FIG. 50 shows the joint J having a varus angulation. It can be seen that central axes 1404, 1406 of the tibia T and femur F, respectively are not coaxial, but define an oblique angle therebetween. FIG. 51 shows a result of releasing the MCL, i.e. effectively lengthening it and/or releasing its tension. It can be seen that the central axes 1404, 1406 are coaxial. This type of adjustment may use any combination of augmentation and/or release and may be used to correct varus or valgus angulation.

Various methods are known for augmentation of the soft tissues. As noted above, one method involves the use of an artificial tensile member such as a suture, cable, or filament, suitably anchored in tension. Examples of this type of device are illustrated in FIGS. 52-57.

Figures 52, 53, 54:
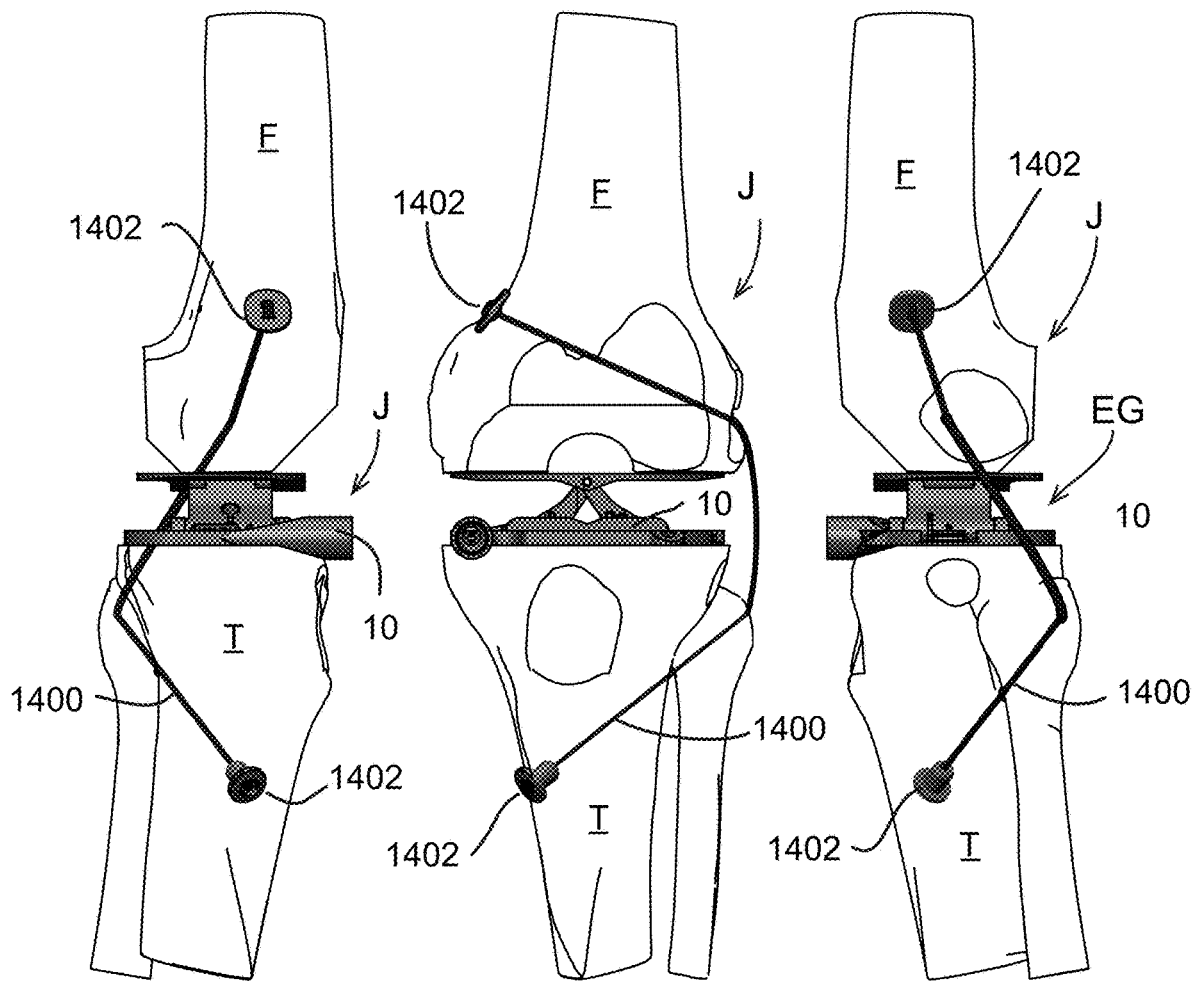
FIG. 52 is a view of the medial aspect of the human knee joint having a gap tensioner inserted therein, in combination with a tensile member used to augment or replace the lateral collateral ligament.
FIG. 53 is a view of the anterior aspect of the human knee joint shown in FIG. 52.
FIG. 54 is a view of the lateral aspect of the human knee joint of FIG. 52.

FIGS. 52-54 illustrate a tensile member 1400 fixed by anchors 1402 and routed through the human knee joint J across the lateral aspect of the extension gap e.g. in order to replace or augment the lateral collateral ligament (not shown).

Figures 55, 56, 57:
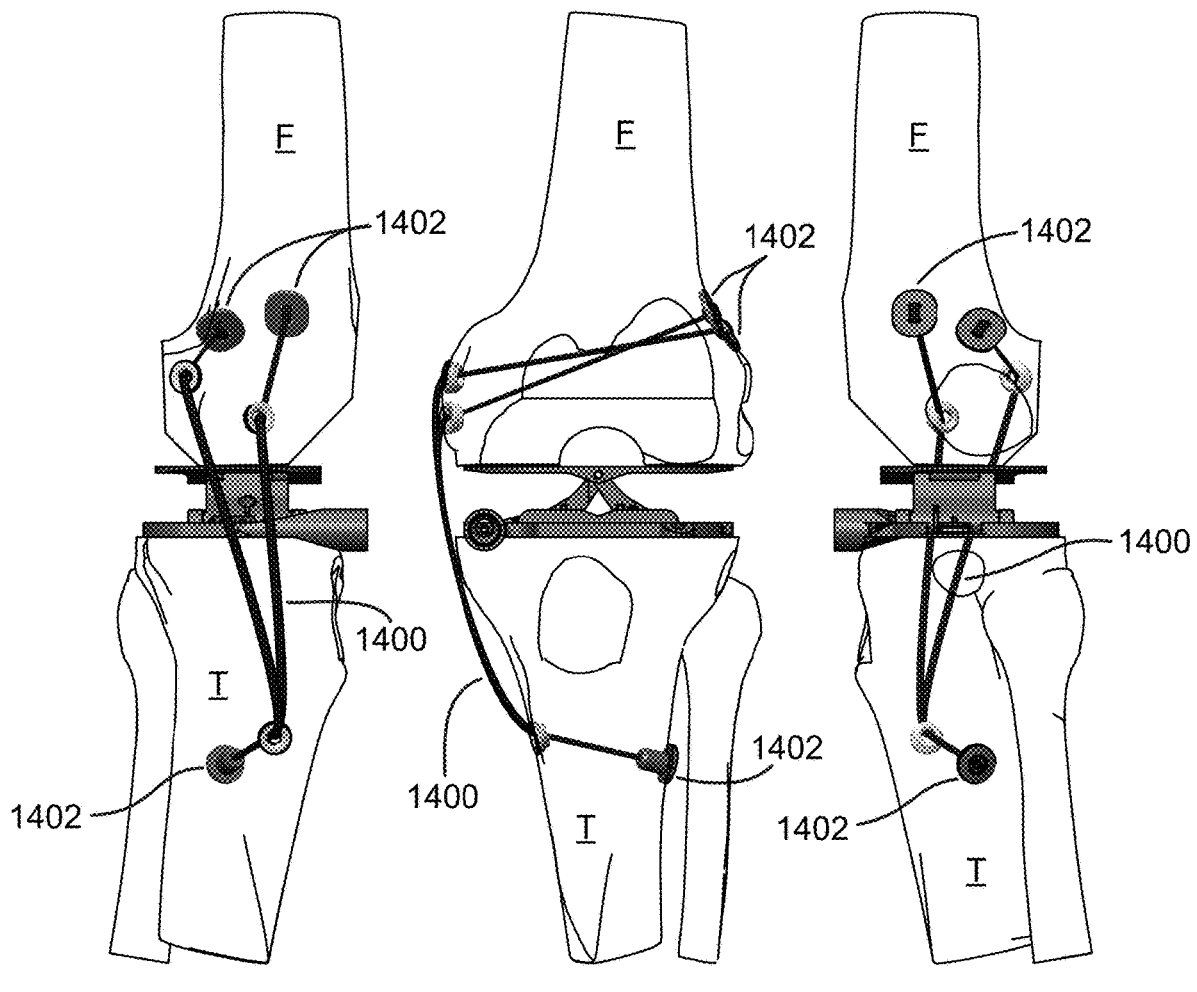
FIG. 55 is a view of the medial aspect of the human knee joint having a gap tensioner inserted therein, in combination with a tensile member used to augment or replace the medial collateral ligament.
FIG. 56 is a view of the anterior aspect of the human knee joint shown in FIG. 55.
FIG. 57 a view of the lateral aspect of the human knee joint of FIG. 55.

FIGS. 55-57 illustrate a tensile member 1400 fixed by anchors 1402 and routed through the human knee joint J across the medial aspect of the extension gap e.g. in order to replace or augment the medial collateral ligament (not shown).

Figure 58:
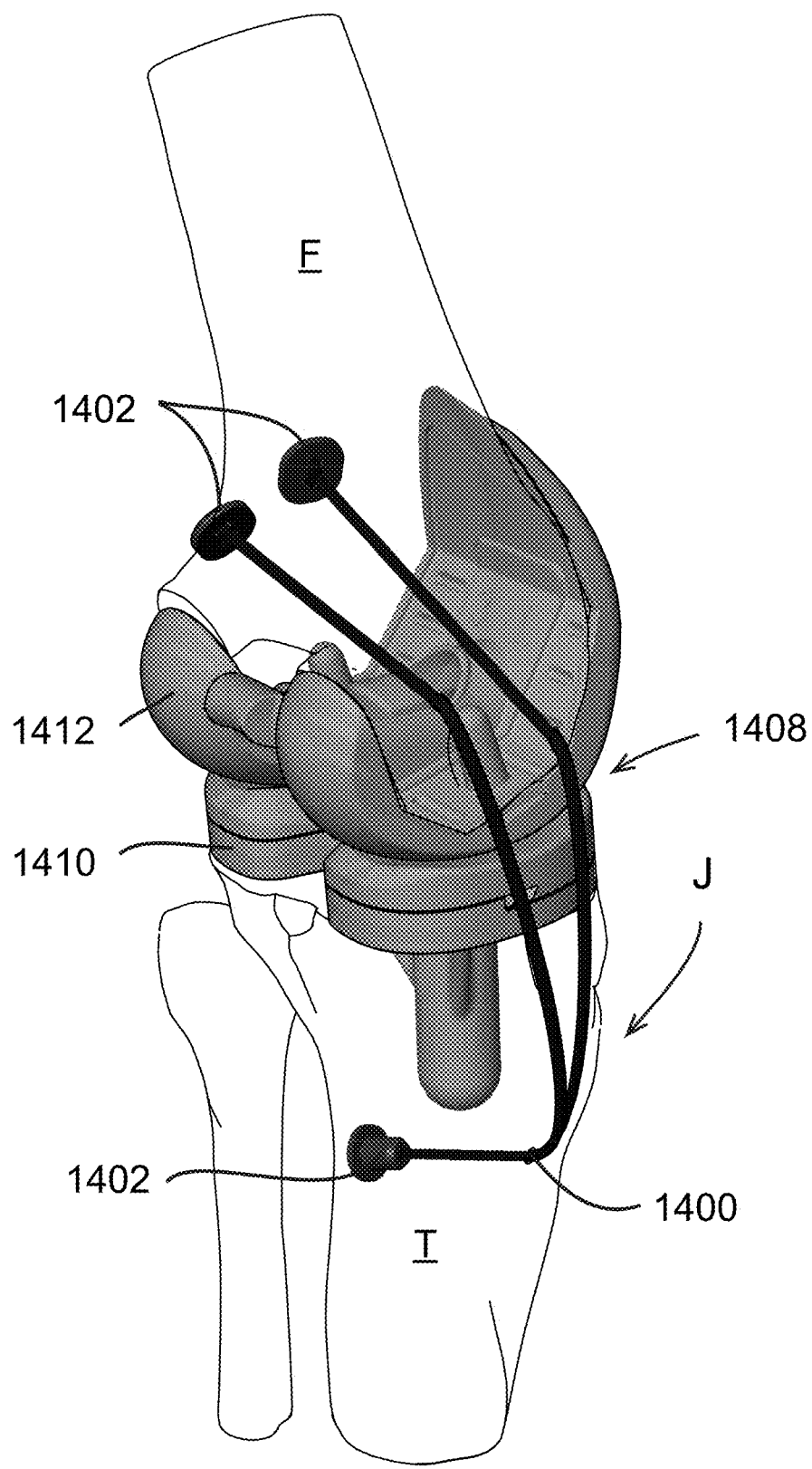
FIG. 58 is a perspective view of a human knee joint having a knee endoprosthetic implanted, in combination with a tensile member used to replace or augment the medial collateral ligament.

FIG. 58 illustrates a human knee joint J having an endoprosthetic 1408 of a known type implanted therein. The endoprosthetic 1408 includes a tibial component 1410 and the femoral component 1412. The joint J also includes a tensile member 1400 fixed by anchors 1402 and routed through the knee joint J across the medial aspect of the extension gap in order to replace or augment the medial collateral segment (not shown).

A method for using the gap tensioner an instrument will now be described with reference to FIGS. 59-73.

Figure 59:
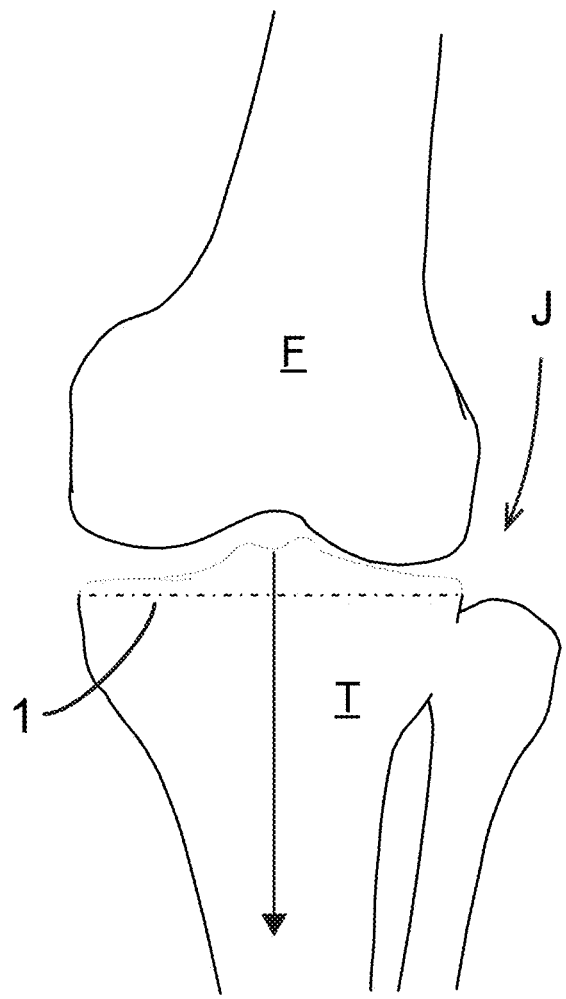
FIG. 59 is a view of the anterior aspect of the human knee joint, illustrating a first step in a total knee arthroscopy.
Figure 60:
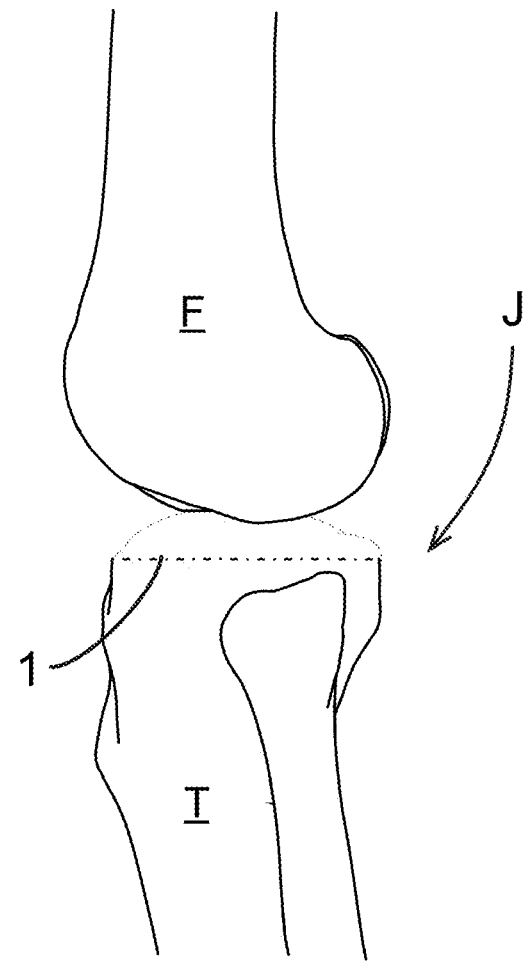
FIG. 60 is a view of the lateral aspect of the joint of FIG. 59.

Initially, FIGS. 59, 60, a tibial cut (cutting plane labeled 1) is made in the tibia T. This may be done using conventional techniques. Ideally, the tibial cut 1 makes a surface that is normal to vertical in the coronal plane and at a slight angle (e.g. 0° to 7°) to vertical in the sagittal plane.

Figures 61, 62:
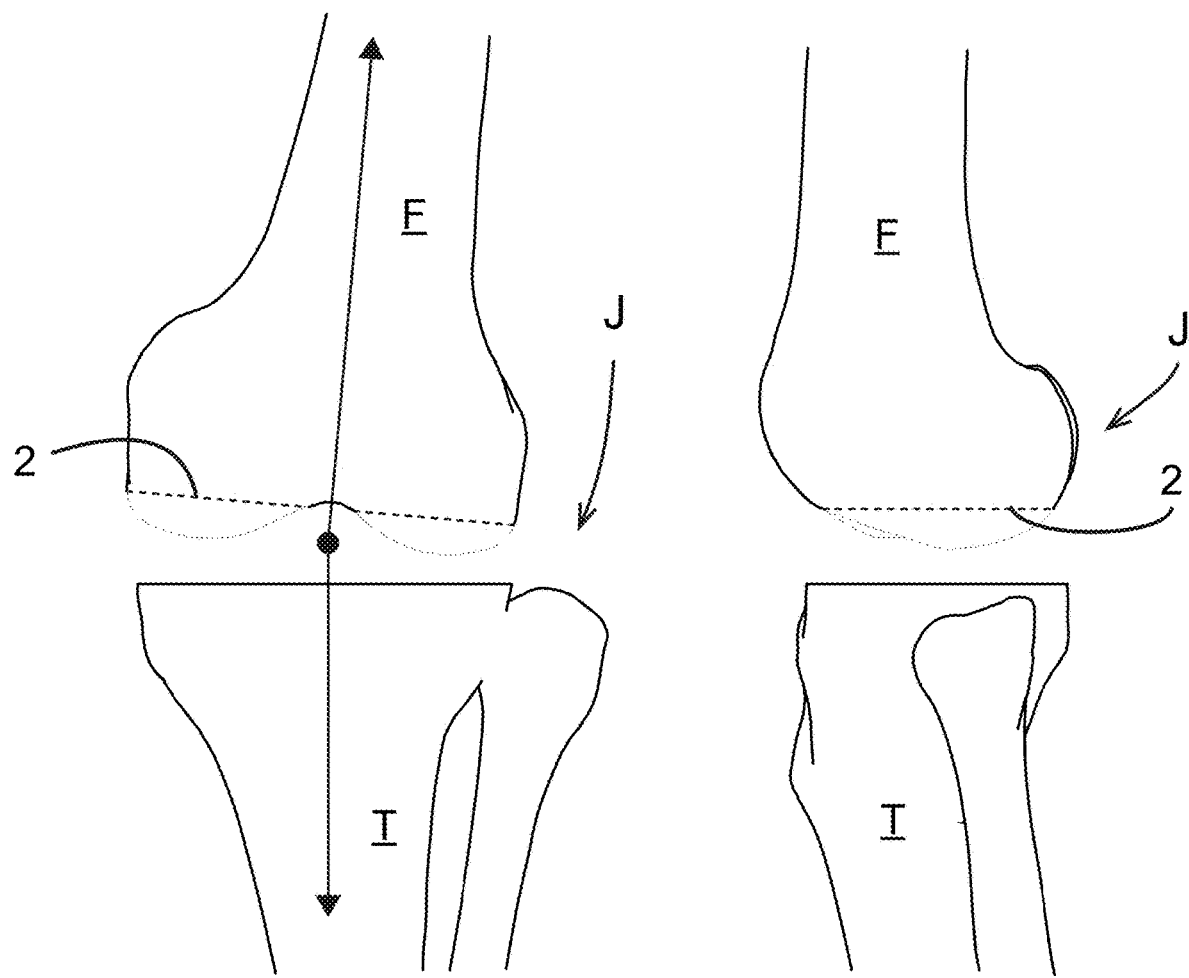
FIG. 61 is a view of the anterior aspect of the human knee joint of FIG. 59, illustrating a second step in a total knee arthroscopy.
FIG. 62 is a view of the lateral aspect of the joint of FIG. 61.

In a second step, FIGS. 61, 62 a distal femoral cut (cutting plane labeled 2) is made in the femur F. This may be done using conventional techniques. Ideally the distal femoral cut 2 makes a surface that is normal to a "perfect" anatomical mechanical axis between the center of the knee and the femoral head.

Figures 63, 64:
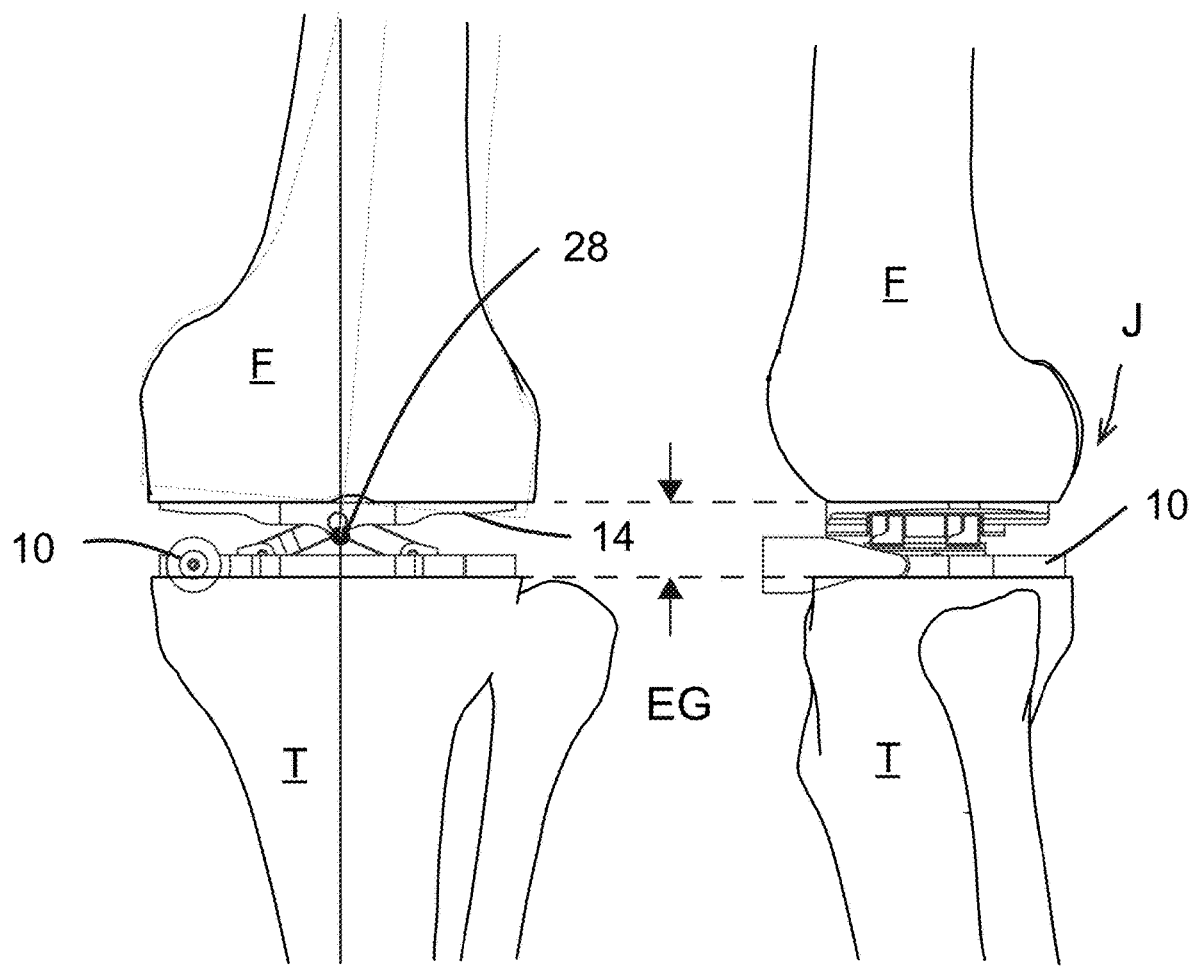
FIG. 63 is a view of the anterior aspect of the human knee joint of FIG. 59, illustrating a third step in a total knee arthroscopy, with a gap tensioner inserted.
FIG. 64 is a view of the lateral aspect of the joint FIG. 59.

In the third step, FIGS. 63, 64, the gap tensioner 10 is inserted between the femur F and the tibia T and used to conduct a soft-tissue balancing procedure. The gap tensioner 10 is moved towards an extended position which has the effect of driving the femur F and the tibia T apart from each other, defining the extension gap EG. The gap tensioner 10 is conformable to lateral angulation. That is, the free pivoting of the top plate 14 about the pivot axis 28 permits the knee joint J to take up whatever varus or valgus angulation naturally occurs.

The specific varus or valgus angulation will be governed by the relative lengths of the medial collateral ligament and the lateral collateral ligament. The extension of the gap tensioner drives both of these ligaments to their full extension. The preload of the tensioner 10 provides a margin to ensure full extension.

Once desired extension, for example full extension. of both ligaments is achieved, the lateral angulation (varus or valgus) can be observed, measured, and/or recorded. Measurement may be by various means. In one example, dimensions and angles may be measured directly using measuring instruments.

Once the lateral angulation is determined, the extension gap EG may be balanced. To balance extension gap, soft-tissue is augmented and/or soft-tissue is released, using the procedure described in detail above with reference to FIGS. 47-51. In the example shown in FIGS. 61 and 62, the knee joint J exhibits valgus angulation (knock-knee) when loaded by the gap tensioner 10. Correction may be performed by augmenting the medial collateral ligament and/or releasing the lateral collateral ligament. The balance procedure is done until the extension gap EG is uniform (i.e. no varus or valgus angulation).

Once the extension gap EG has been balanced, resulting in the condition shown in FIGS. 63 and 64, they gap tensioner 10 may be used to establish the flexion cuts.

Figures 65, 66:
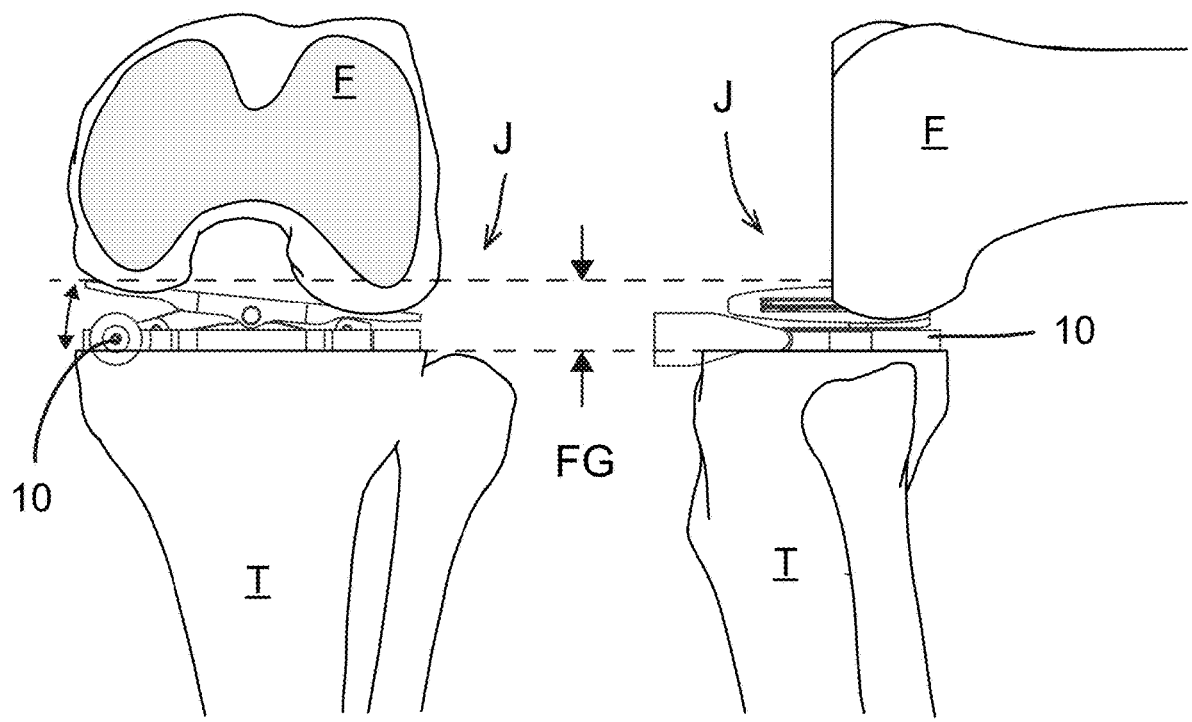
FIG. 65 is a view of the anterior aspect of the human knee joint of FIG. 52 in flexion, illustrating a fourth step in a total knee arthroscopy, with the gap tensioner inserted.
FIG. 66 is a view of the lateral aspect of the joint of FIG. 65.

Referring to FIGS. 65 and 66, the gap tensioner 10 is placed in the flexion gap FG and tensioned to the same load as used to establish the extension gap EG. This may be carried out with the patella and/or patellar tendon (not shown) in place (i.e., the patella is not required to be everted and may be in the normal anatomical position).

Once full extension of both ligaments is achieved, the characteristics of the flexion gap FG (magnitude and angulation) can be observed, measured, and/or recorded. The soft tissue is not altered in this step. It will be understood that the magnitude (height) and/or tilt of the flexion gap FG are likely to be different from the extension gap EG. It will be further understood that is desirable for the flexion gap FG to be parallel and equal to the extension gap EG. In the example shown in FIGS. 65 and 66, the knee joint J exhibits valgus angulation (knock-knee) when loaded by the gap tensioner 10. Furthermore, since the posterior cut has not yet been made, the flexion gap FG is smaller than the final required amount. It can be seen from FIG. 65 that in order to create a balanced flexion gap FG, the posterior cut must remove the different amounts of material from the two condyles of the femur F.

Figures 67, 68:
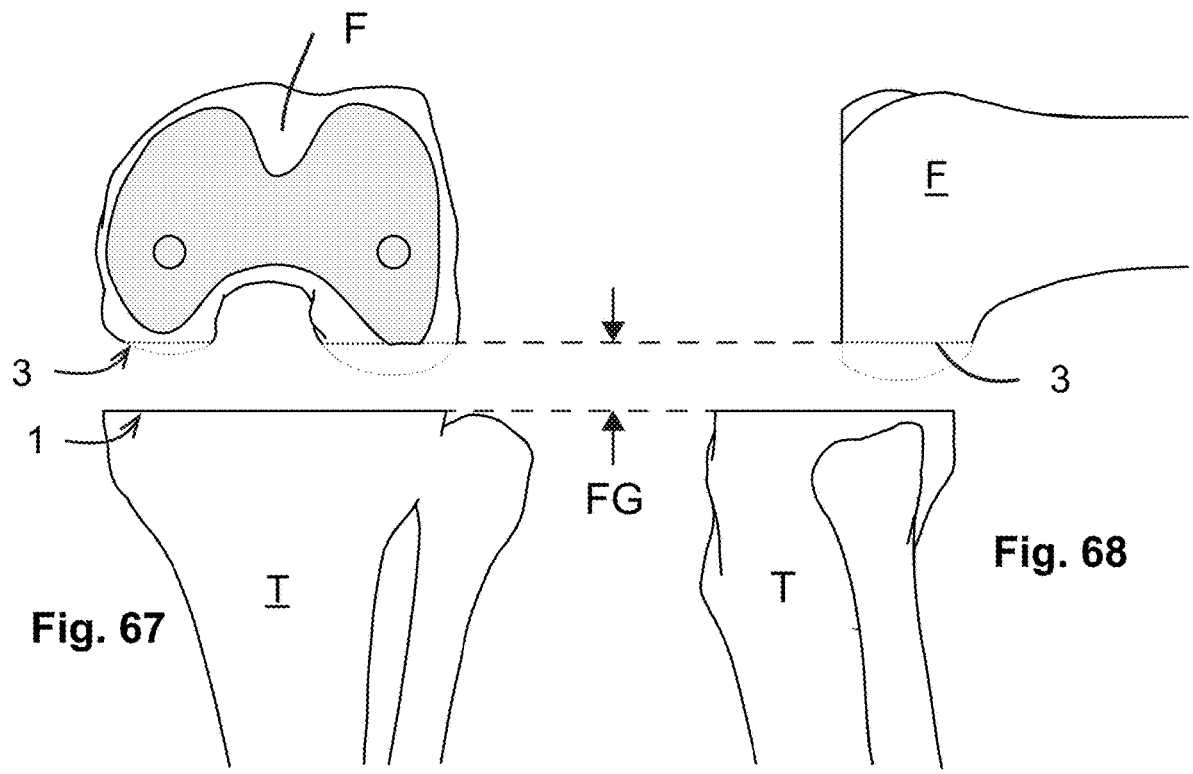
FIG. 67 is a view of the anterior aspect of the human knee joint of FIG. 59 in flexion, illustrating a fifth step in a total knee arthroscopy.
FIG. 68 is a view of the lateral aspect of the joint of FIG. 67.
Figure 69:
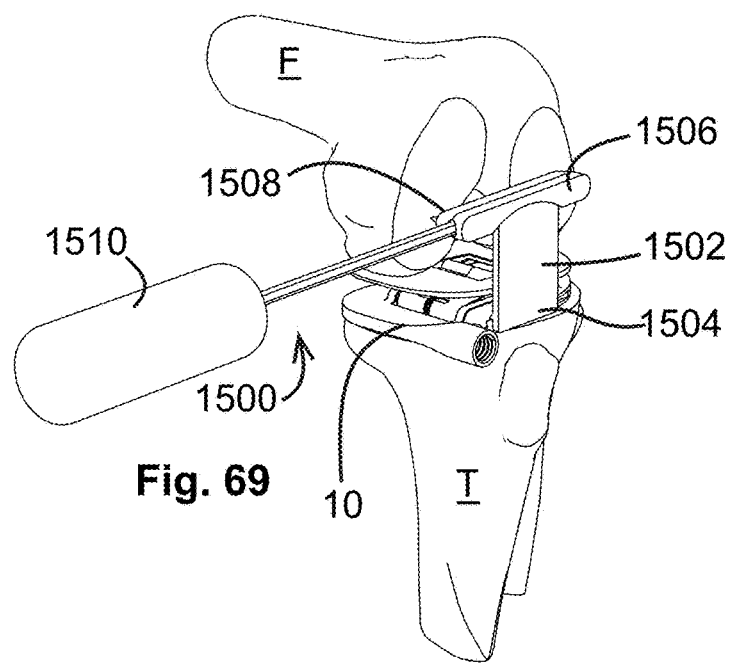
FIG. 69 is a perspective view of the human knee joint of FIG. 59, showing a marking device positioned within the joint.
Figure 70:
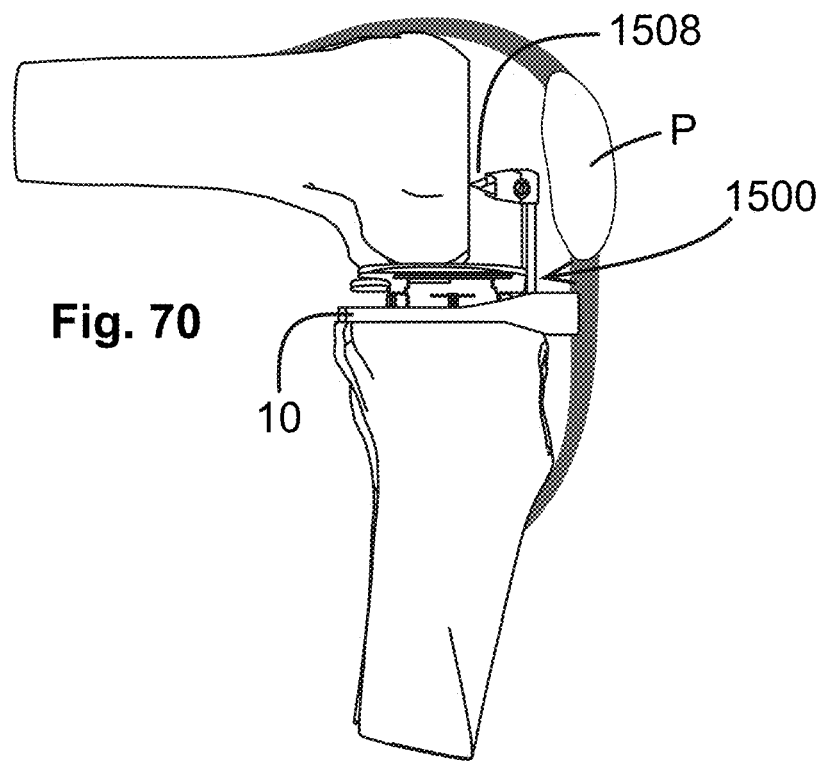
FIG. 70 is another view of the medial aspect of the joint in FIG. 69, showing the patella in place.
Figure 71:
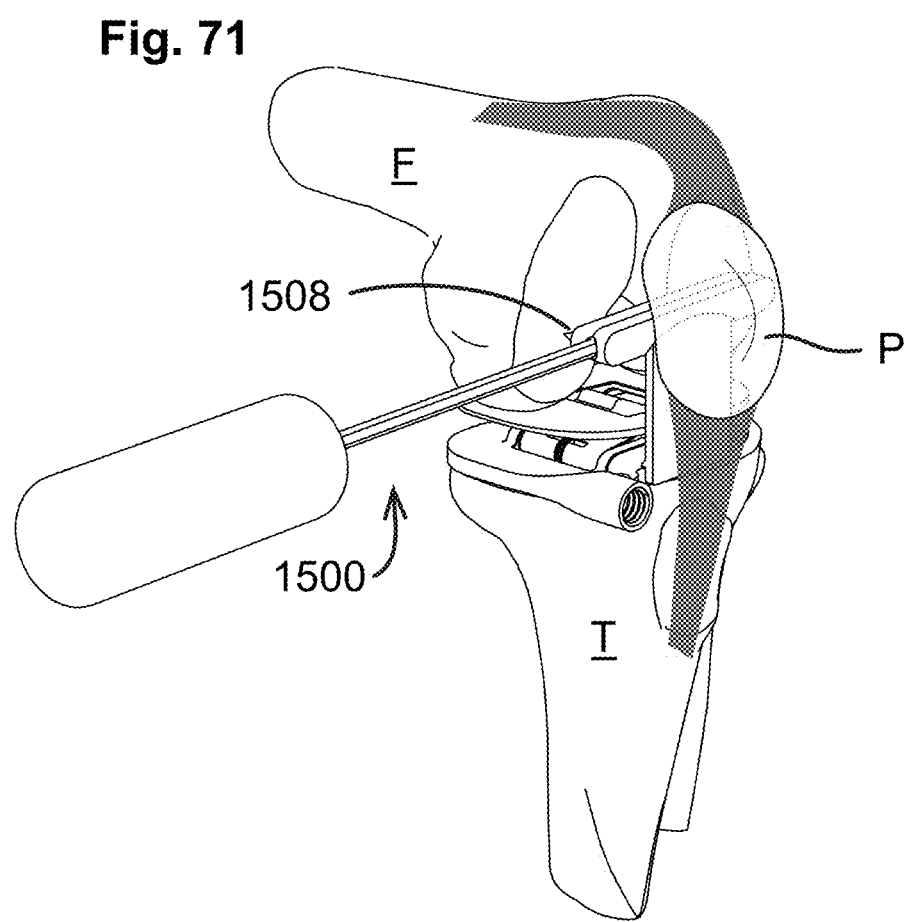
FIG. 71 is a perspective view of the joint in FIG. 69, showing the patella in place.

The posterior cut (cutting plane labeled 3) is then made so as to create the desired (balanced) flexion gap FG', as seen in FIGS. 66 and 67. The gap tensioner 10 may be utilized to accurately mark the desired cutting plane. Referring to FIGS. 69-71, the gap tensioner 10 is left inserted into the flexion gap FG, maintaining tension on the soft tissue while references are marked for the posterior cut.

In the example shown in FIGS. 69-71, a marking attachment 1500 is provided which includes a body 1502 of a predetermined height extending between first and second ends 1504, 1506. The first end 1504 is provided with means for attachment to the base plate 12 of the gap tensioner 10. For example, a dovetail joint (not shown) may be used. The second end 1506 is provided with suitable marking implement such as the illustrated two spaced-apart marking tips 1508 positioned along the line parallel to the tibial surface 18 of the base plate 12. The marking attachment 1500 may further include a handle 1510 to allow for surgical manipulation.

The marking attachment 1500 is used by attaching it to the baseplate 12 with the joint J in flexion and then using the marking tips 1508 to strike or impress two indentations which serve as a reference for mounting of a cutter guide block described below. This may be carried out with the patella "P" in place (not everted), as seen in FIGS. 70 and 71. It will be understood that the geometry of the marking attachment 1500 ensures that the two indentations lie on a line parallel to the tibial cut in the tibia T. Accordingly, this provides a basis for making a posterior cut which is automatically ensured to be parallel to the tibial cut.

Figure 72:
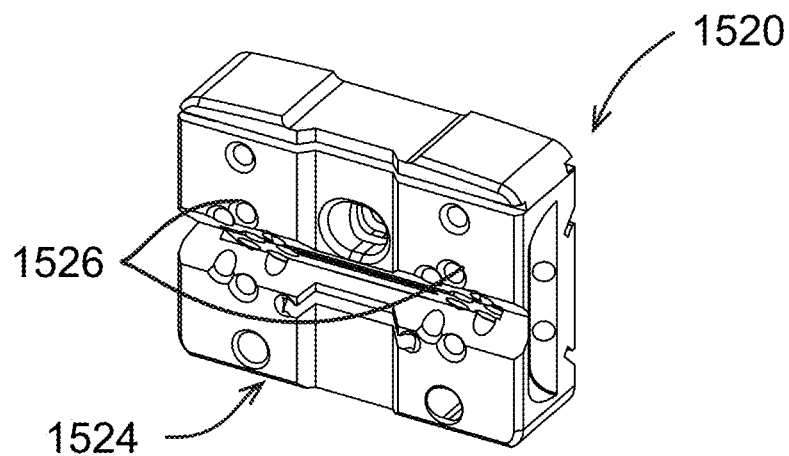
FIG. 72 is a perspective view of a cutter guide block.

FIG. 72 illustrates a suitable cutter guide block 1520 of a known type. The cutter guide block 1520 includes, among other features, a posterior cut guide surface 1524 and at least one pair of space-apart guide holes 1526. The guide holes 1526 are configured to receive guide pins or screws (not shown) which may be driven into bone to hold the cutter guide block 1520 in position while the posterior cut guide surface 1524 is used to guide the blade of a bone saw (not shown). Fundamentally, in order to produce the desired cut, the posterior cut guide surface 1524 is placed parallel to and coplanar with or slightly spaced away from the posterior cut plane 3.

Figure 73:
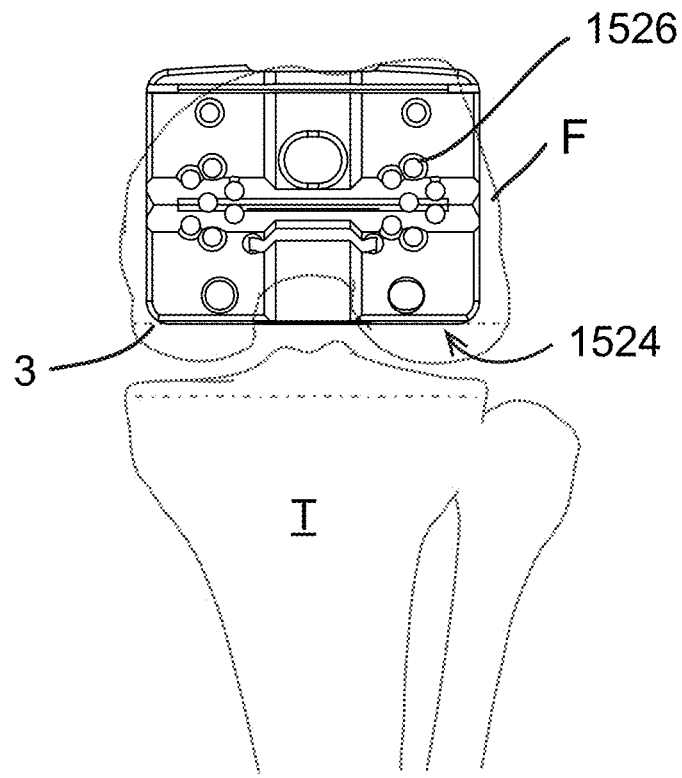
FIG. 73 is a view of an anterior aspect of the human knee joint in flexion, with the cutter guide block of FIG. 72 in place.

It will be understood that the guide holes 1526 lie along a line which is parallel to the posterior cut guide surface 1524, at a known distance from the posterior cut guide surface 1524. Accordingly, in order to accurately position the cutter guide block 1520, it is a straightforward matter to select the height of the marking attachment 1500, and thus the position of the marking tips 1508, taking into account the distance between the guide holes 1526 and the posterior cut guide surface 1524, and the desired final height of the flexion gap FG. FIG. 73 shows the cutter guide block 1520 in-place against the femur F, ready to make the posterior cut 3.

Once a posterior cut 3 is made, the knee joint J as a balanced flexion gap FG which matches the extension gap EG. Subsequently, conventional steps may be carried out to complete the total the arthroscopy, such as making chamfer cuts, trial fitting the endoprosthetic components, and cementing the endoprosthetic components.

Figure 74:
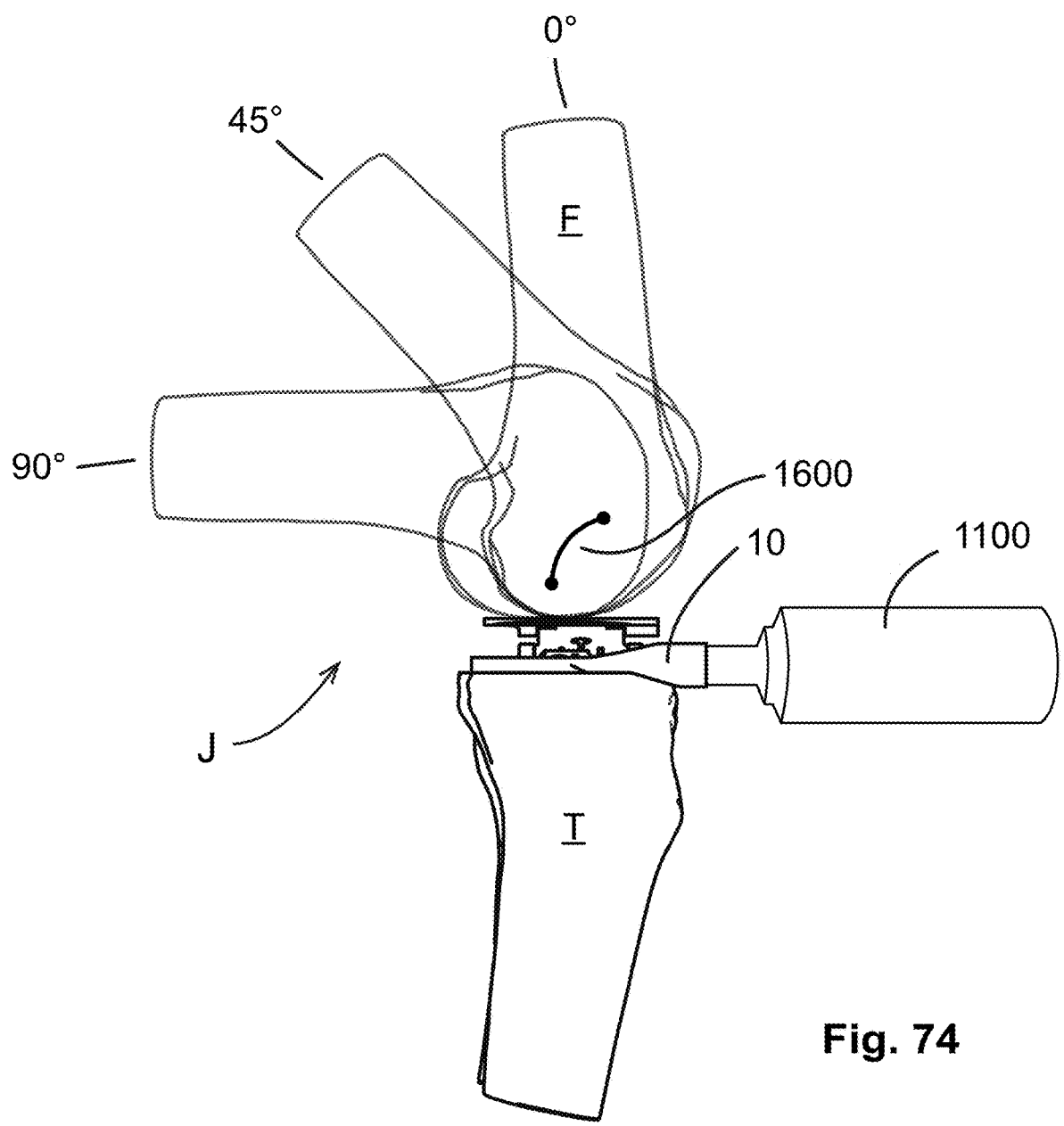
FIG. 74 is a view of the medial aspect of the human knee joint having a gap tensioner inserted therein.

The devices described above have additional usefulness in related surgical procedures, particularly in determining the proper bone entry points for artificial tensile members used to augment the natural ligaments. FIG. 74 is a view of the medial aspect of the human knee joint J having a gap tensioner 10 inserted therein. The view shows the joint with three different positions of the femur F superimposed—full extension labeled 0°, an intermediate position labeled 45°, and full flexion labeled 90°. Shown also on the femur F is a curve 1600 which represents the locus of the instantaneous axis of rotation ("IAOR") of the joint J for each position. The IAOR changes throughout the joint range of motion. This happens because during joint motion the femoral condyle translates in the anterior/posterior directions and the femoral condyle rides against the tibia in a cam motion.

For best surgical outcomes, it is preferable to route an artificial tensile member through a hole in the femur F passing through curve 1600. The exact location of this curve 1600 can be difficult to determine using prior art methods. The apparatus described herein can provide a method for accurately locating this curve to serve as a drilling target.

In one example, the location method may be carried out using the instrument 1100 described above. As noted above, the instrument 1100 may include appropriate sensors for determining the extension load, the varus/valgus tilt angle, and the gap height. In order to locate the curve 1600, the instrument 1100 would be coupled to a gap tensioner 10 inserted into the knee joint J between the tibia T and the femur F, after making the tibial cut but prior to making the distal femoral cut. In one option, a predetermined extension load would be applied by the instrument 1100. The joint J would then be moved through the range of full extension to full flexion, while using the sensors to determine the gap height and varus/valgus angle in each location within the range of motion. This data may be translated through empirical means to derive the location of the curve 1600.

Figure 82:
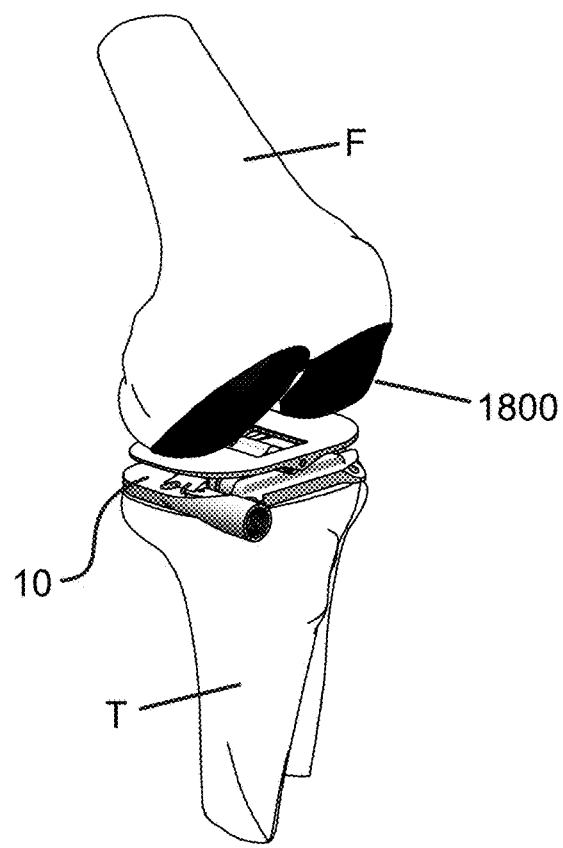
FIG. 82 is a schematic perspective view of a human knee joint having a gap tensioner and trial condyle element inserted therein.
Figure 83:
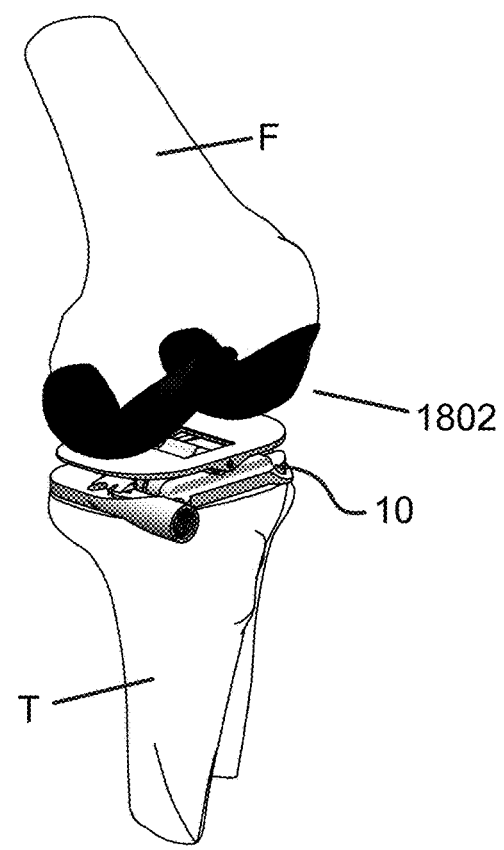
FIG. 83 is a schematic perspective view of a human knee joint having a gap tensioner and trial condyle element inserted therein.

Optionally, this method may be performed after the tibial and femoral cuts have been made, by providing a trail condyle element of an arthroplasty. For example, FIG. 82 illustrates a trial condyle element 1800 inserted between the femur F and the gap tensioner 10. This configuration permits a continuous range of joint motion after the distal femoral cut is made. As another example, FIG. 83 illustrates a trial condyle element 1802 inserted between the femur F and the gap tensioner 10. This configuration permits a continuous range of joint motion after the distal femoral and posterior formal cuts are made.

In another option, the instrument 1100 will be controlled so as to provide a fixed gap height. The joint J would then be moved to the range of full extension of full flexion, while using the sensors to determine the change in extension load and the varus/valgus angle in each location within the range of motion. This data may be translated through empirical means to derive the location of the curve 1600.

Figure 75:
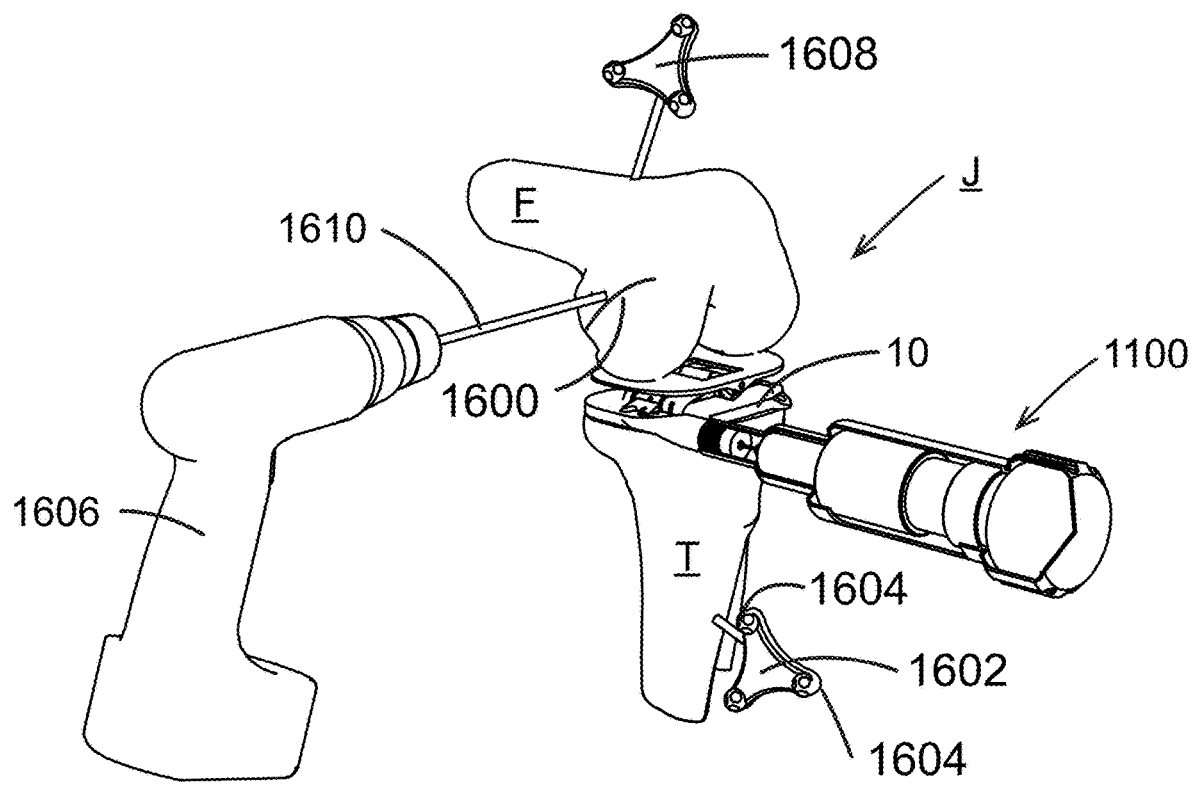
FIG. 75 is a perspective view of the human knee joint having a gap sensor inserted therein and tracking markers attached thereto.

In a related method, described with respect to FIG. 75, the instrument 1100 described above may be used with other apparatus not only to derive the location of the curve 1600 but to guide the surgeon to drill a hole in a proper location along the curve. The instrument 1100 would be coupled to the gap tensioner 10 inserted into the knee joint J between the tibia T in the femur F, after making the tibial cut prior to making the distal femoral cut. A tracking marker 1602 would be attached to the tibia T. The tracking marker 1602 is attached to the tibia T in such a way that it has a substantially fixed position and orientation relative to the tibia T. It includes one or more tracking points 1604 which may be configured as transmitting antennas, radiological markers, or other similar devices. Using an appropriate receiving device such as the illustrated instrumented, receiver-equipped cordless drill 1606, the position and orientation of the cordless drill 1606 relative to the tracking marker 1602 may be determined by receipt and analysis at the cordless drill 1606 of signals transmitted by the tracking marker 1602. Tracking marker 1602 and appropriate receivers are known within the state-of-the-art. Additionally, a second tracking marker 1608 would be attached to the femur F in such a way that as a substantially fixed position orientation relative to the femur F. Again, the position orientation of the cordless drill 1606 relative to the tracking marker 1608 may be determined.

Once the gap tensioner 10, actuating instrument 1100, and tracking markers 1602 and 1608 are implanted, the joint J would then be moved to the range of full extension of full flexion, while monitoring the position of tracking markers 1602 and 1608. The path swept out by the tracking marker 1602 and 1608 is representative of the movement of the condyle of the femur against the gap tensioner 10. The data representing the path may be translated using empirical means to determine the position of the curve 1600.

Once a position of the curve 1600 is determined, the tracking markers 1602 and 1608 may be used to guide the cordless drill 1606 to drill a hole passing through the curve 1600, with the drill bit 1610 extending an appropriate angle. This guidance is possible because intercommunication between the cordless drill 1606 and the tracking marker 1602 and 1608 will give the relative to position and orientation of the cordless drill 1606 to those markers. The drilling guidance may be provided in the form of information displayed on the remote display 1162 described above. For this purpose, 2-way data communications may be provided between and among the cordless drills 1606 (or other surgical instrument), the tracking markers 1602 and 1608, the actuating instrument 1100, and the remote display 1162.

This method is especially helpful in providing drilling guidance because it provides the benefits of a surgical navigation system, which is typically large, complex, and expensive, using simple inexpensive local relative position information. For example, the absolute position and orientation of the knee joint J is not required to perform the step of moving the joint J through the range of motion and then guiding the cordless drill 1606 to drill a hole at the appropriate location and orientation.

In another related method, described with respect to FIGS. 78-81, the instrument 1100 described above may be used in combination other apparatus to improve accuracy of alignment of the knee joint J. FIG. 78 illustrates the knee joint J between the femur F and tibia T, the talus joint "U" between the tibia T and the foot "0", and the acetabulofemoral joint "B" between the femoral condyle "C" and the pelvis "P". FIG. 78 also illustrates an axis 1405 passing through the femoral condyle C and the talus joint U. The ability to measure lateral position of the knee joint J relative to the axis 1405 is helpful in determining angulation (i.e. varus/valgus) of the knee joint J. For purposes of this measurement, the center of the knee joint J and the lateral sense is considered to be the midpoint between the medial and lateral condyles. For example, in general a nominal varus/valgus angulation occurs when the center of the knee joint J is coincident with the axis 1405. Different patients may exhibit variations in the nominal position. Furthermore, a surgically desirable varus/valgus angulation may be different from nominal this may be done, for example to correct a defect in the patient's anatomy.

Various methods are possible for establishing the location of the axis 1405. One method involves the use of an atomic old tracking markers or "navigation" systems. FIG. 76 illustrates schematically a first tracking marker 1700 disposed at the center of the femoral condyle C, a second tracking marker 1702 located at the center of the knee joint J, and a third tracking marker 1704 located at the center of the talus joint U. The tracking markers 1700, 1702, 1704 are representative of the position of the associated anatomical structures. In practice, the tracking markers may be physical or virtual. For example, surgical navigation systems are commercially available which have the capability of measuring the position of hardware tracking markers and/or generating virtual tracking markers through the use of medical imaging methods.

Once the tracking markers 1700, 1702, 1704 are established, the knee joint J may be placed in flexion as shown in FIG. 79. The complete leg may then be moved laterally to the left and the right alternatively, thus generating a position track for each of the tracking markers 1700, 1702, 1704. This movement will cause rotation of the leg about the axis 1405 which intersects the first tracking marker 1700 and the third tracking marker 1704. The axis 1405 may be analytically constructed, for example by observing that the first and third tracking marker 1700, 1704 exhibit little to no movement while the second tracking marker 1702 sweeps out an arc. Computation will show the center of this arc lies on the axis 1405.

Figure 81:
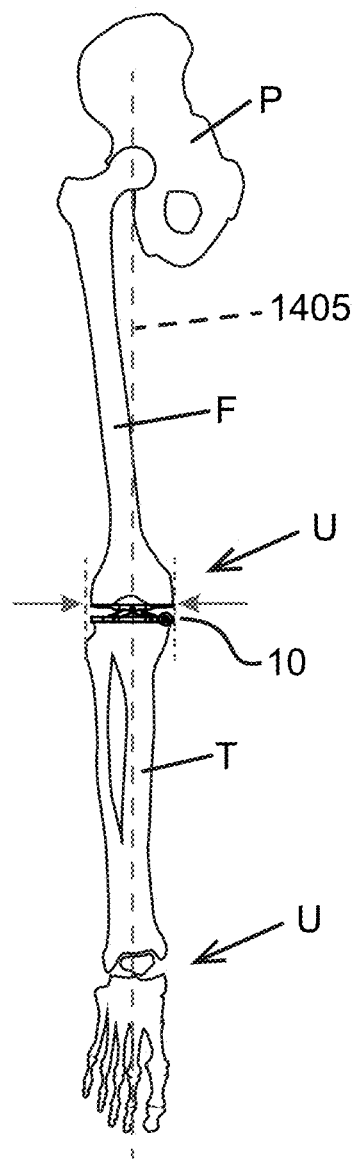
FIG. 81 is a view of an anterior aspect of the human leg of FIG. 80 in extension.

The function of the tracking markers 1700, 1702, 1704 may be replaced in whole or in part with local, relative navigation devices such as the tracking markers described above. This is shown in FIGS. 81 and 81. In this example configuration, a tracking marker 1608 (described above) is attached to the femur F in such a way that as a substantially fixed position orientation relative to the femur F.

Another tracking marker 1708 is coupled to the talus joint U in such a way that as a substantially fixed position orientation relative to the femur F. For example, it may be coupled t the talus joint U using a C-shaped ankle clip or ankle clamp 1710 which may be resilient, spring-loaded, etc.

Finally, the gap tensioner 10 is inserted into the knee joint J and coupled to the actuation instrument 1100 having a tracking marker 1162 as described above. Alternatively, the gap tensioner 10 may be provided with a built-in tracking marker (not shown).

A receiving device such as remote display 1062 is configured to receive the signals and or otherwise track the positions of the tracking markers 1162, 1608, and 1708 and to store, manipulate, and/or display the position data.

Once the gap tensioner 10, actuating instrument 1100, and tracking markers 1162, 1608, and 1708 are in place, the leg would then be moved to a flexion position. The complete leg may then be moved laterally to the left and the right alternatively, while monitoring the position of tracking markers 1162, 1608, and 1708, thus generating a position track for each of the tracking markers 1162, 1608, and 1708. The axis 1405 may be analytically constructed, for example by observing that the tracking markers 1162, 1608 exhibit little to no movement while the tracking marker 1708 sweeps out an arc. Computation will show the center of this arc lies on the axis 1405.

Once a position of the axis 1405 is determined, the leg can be placed back in extension and tracking markers 1602 and 1608 may be used to measure lateral position of the knee joint J relative to the axis 1405. As noted above, this information is helpful in determining angulation (i.e. varus/valgus) of the knee joint J.

The apparatus and method described herein have numerous advantages over prior art apparatus and techniques.

The gap tensioner enables patella-in-place gap balancing during total knee arthroplasty. By allowing the patella (and other soft tissue around the knee space) to remain in its anatomical position during the balancing procedure, a more accurate and anatomically relevant gap can be established.

Furthermore, due to its non-intrusive nature, the gap tensioner can enable in-situ gap balancing by means of soft tissue releases (to open one side of the gap relative to the other to make it more "rectangular" and less "trapezoidal") and tension ligament augmentation (to close one side of the gap by tightening or augmenting ligaments to make it more "rectangular" and less "trapezoidal").

The foregoing has described apparatus and methods for knee gap tensioning. All of the features disclosed in this specification, and/or all of the steps of any method or process so disclosed, may be combined in any combination, except combinations where at least some of such features and/or steps are mutually exclusive.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends, or to any novel one, or any novel combination, of the steps of any method or process so disclosed.

What is claimed is:

1. A method for balancing extension and flexion gaps between the tibia and the femur of a knee joint, comprising:
    making a tibial cut along the first cutting plane to cut away a proximal portion of the tibia, and making a distal femoral cut along a second cutting plane to cut away a distal portion of the femur, such that an extension gap is defined between the first and second cutting planes;
    positioning the knee joint in extension and inserting a gap tensioner into the extension gap, the gap tensioner including:
    a baseplate;
    a top plate;
    a linkage interconnecting the baseplate and the top plate and operable to move the gap tensioner between retracted and extended positions; and
    wherein the top plate is pivotally connected to the linkage so as to be able to freely pivot about a pivot axis;
    actuating the linkage to move the gap tensioner towards the extended position, so as to urge the tibia and the femur apart and apply tension to the medial and lateral collateral ligaments of the knee joint; and
    determining an adjustment required to bring the first and second cutting planes into a desired angular orientation relative to each other;
    positioning the knee joint in flexion, thereby defining a flexion gap between the femur and the tibia;
    positioning the gap tensioner into the flexion gap and actuating the linkage to move the gap tensioner towards the extended position, so as to urge the tibia and the femur apart and apply tension to the medial and lateral collateral ligaments of the knee joint; and
    determining a third cutting plane to be used for a posterior cut on the femur which will result in the first and third cutting planes being substantially parallel in at least one axis;
    removing the gap tensioner; and
    making the posterior cut along the third cutting plane.

2. The method of claim 1 further comprising selectively augmenting or releasing at least one of the medial and lateral collateral ligaments.

3. The method of claim 2 wherein the selective augmentation or release occurs prior to determining the third cutting plane.

4. The method of claim 1 further comprising using the gap tensioner to make real-time measurements of gap distance, angle, and separating force during ligament tension augmentation or reduction.

5. The method of claim 1 wherein the second cutting plane is altered by making at least one bone resection cut.

6. The method of claim 1 wherein the patella and patellar tendon of the knee joint are disposed in a normal anatomical position.

7. The method of 1 further comprising the addition of an implantable tensile member to augment a tensile force between the femur and tibia.

8. The method of claim 7 wherein the step of determining the third cutting plane is carried out by:
    connecting a marking attachment to the gap tensioner, the marking attachment including a marking implement positioned to define a line parallel to the first cutting plane; and
    using the marking implement to make one or more marks on the femur.

9. The method of claim 8 further comprising attaching a cutter guide block to the femur in a predetermined position relative to the marks made by the marking implement, wherein the cutter guide block includes a posterior cut guide surface having a predetermined angular alignment relative to the first cutting plane.

10. A method of measuring alignment of a human knee joint which includes a femur bone, a tibia bone, a patella bone, a patellar tendon, and ligaments, wherein the ligaments and patellar tendon are under anatomical tension to connect the femur and tibia together, creating a load-bearing articulating joint; the method comprising:
    providing a gap tensioning apparatus including:
    a gap tensioner including:
        a baseplate;
        a top plate;
        a linkage interconnecting the baseplate and the top plate and operable to move the gap tensioner between retracted and extended positions; and
        wherein the top plate is pivotally connected to the linkage so as to be able to freely pivot about a pivot axis;
    inserting the gap tensioner between the tibia and the femur, with the gap tensioner in the retracted position;
    actuating the linkage to move the gap tensioner towards the extended position, so as to urge the tibia and the femur apart and apply tension to the medial and lateral collateral ligaments of the knee joint;
    associating at least two tracking markers with the knee joint;
    providing an electronic receiving device, wherein the receiving device is operable in combination with the tracking markers to determine a position and orientation of each of the tracking markers relative to the electronic receiving device;
    moving the knee joint through at least a portion of its range of motion;
    while moving the knee joint, collecting position data from the tracking markers; and
    processing the collected position data to compute an origin of motion of the knee joint.

11. The method of claim 10 further comprising carrying out a surgical correction of the knee joint with reference to the computed origin of motion.

12. The method of claim 11 wherein the origin of motion is an instantaneous axis of rotation of the knee joint, and the surgical correction comprises implanting an end of a tensile member with reference to the computed origin of motion.

13. The method of claim 10 further comprising:
    moving the knee joint to flexion;
    moving the leg laterally so as to produce rotation thereof; and
    wherein the origin of motion is an axis passing through the talus joint and the femoral head.

14. The method of claim 13 wherein at least one of the tracking markers comprises a C-shaped clip coupled to a talus joint.

15. The method of claim 10 further comprising measuring a relative position of the tracking markers to determine a varus/valgus angle of the knee joint.

16. The method of claim 10 wherein one of the tracking markers is contained in the gap tensioner.

17. The method of claim 10 wherein one of the tracking marks is contained in an actuating instrument coupled to the gap tensioner.

\* \* \* \* \*